(12) United States Patent
Mingozzi et al.

(10) Patent No.: US 11,339,406 B2
(45) Date of Patent: May 24, 2022

(54) ACID-ALPHA GLUCOSIDASE VARIANTS AND USES THEREOF

(71) Applicants: GENETHON, Evry (FR); INSERM (INSTITUT NATIONAL DE LA SANTE ET DE LA RECHERCHE MEDICALE), Paris (FR); UNIVERSITE D'EVRY VAL D'ESSONNE, Evry (FR)

(72) Inventors: Federico Mingozzi, Paris (FR); Giuseppe Ronzitti, Paris (FR)

(73) Assignees: GENETHON, Evry (FR); INSERM (INSTITUT NATIONAL DE LA SANTE ET DE LA RECHERCHE MEDICALE), Paris (FR); UNIVERSITE D'EVRY VAL D'ESSONNE, Evry (FR)

( * ) Notice: Subject to any disclaimer, the term of this patent is extended or adjusted under 35 U.S.C. 154(b) by 0 days.

(21) Appl. No.: 16/332,379

(22) PCT Filed: Sep. 12, 2017

(86) PCT No.: PCT/EP2017/072944
§ 371 (c)(1),
(2) Date: Mar. 12, 2019

(87) PCT Pub. No.: WO2018/046774
PCT Pub. Date: Mar. 15, 2018

(65) Prior Publication Data
US 2019/0390225 A1  Dec. 26, 2019

(30) Foreign Application Priority Data

Sep. 12, 2016  (EP) ..................... 16306150
Sep. 16, 2016  (EP) ..................... 16306187

(51) Int. Cl.
| | |
|---|---|
| *C12N 9/24* | (2006.01) |
| *C12N 15/90* | (2006.01) |
| *C12N 15/87* | (2006.01) |
| *C12N 15/86* | (2006.01) |
| *A61K 35/34* | (2015.01) |
| *A61K 35/407* | (2015.01) |

(52) U.S. Cl.
CPC .............. *C12N 15/86* (2013.01); *A61K 35/34* (2013.01); *A61K 35/407* (2013.01); *C12N 2510/00* (2013.01); *C12N 2750/14143* (2013.01); *C12Y 302/0102* (2013.01)

(58) Field of Classification Search
CPC .. A61K 9/0019; A61K 38/47; A61K 47/6871; A61K 16/44; C12N 9/2408
See application file for complete search history.

(56) References Cited

U.S. PATENT DOCUMENTS

| | | | |
|---|---|---|---|
| 9,018,001 B2 * | 4/2015 | Hesketh ........... | C07K 14/43509 435/320.1 |
| 10,017,581 B2 * | 7/2018 | Armstrong ............. | C07K 16/44 |
| 2005/0281805 A1 | 12/2005 | LeBowitz et al. | |
| 2013/0316366 A1 | 11/2013 | Yu et al. | |
| 2014/0155473 A1 | 6/2014 | Bancel et al. | |
| 2019/0390184 A1 | 12/2019 | Mingozzi et al. | |
| 2021/0040503 A1 | 2/2021 | Mingozzi et al. | |

FOREIGN PATENT DOCUMENTS

| | | |
|---|---|---|
| EP | 2 471 929 | 7/2012 |
| WO | WO 2004/064750 | 8/2004 |
| WO | WO 2005/078077 | 8/2005 |
| WO | WO 2012/085622 | 6/2012 |
| WO | WO 2013/013017 | 1/2013 |
| WO | WO 2013/192317 | 12/2013 |
| WO | WO 2015/192092 | 12/2015 |
| WO | WO 2016/065319 | 4/2016 |
| WO | WO 2018/046772 | 3/2018 |
| WO | WO 2018/046775 | 3/2018 |

OTHER PUBLICATIONS

Database Geneseq [Online] Accession No. BAT55892, Nov. 7, 2013, p. 1.
Database Geneseq [Online] Accession No. BCC60420, Sep. 10, 2015, p. 1.
Database Geneseq [Online] Accession No. BCC60459, Sep. 10, 2015, p. 1.
Database Geneseq [Online] Accession No. AZX33968, Aug. 16, 2012, p. 1.
Database Geneseq [Online] Accession No. BBM52043, Oct. 23, 2014, p. 1.
Database Geneseq [Online] Accession No. BCK01721, Feb. 25, 2016, p. 1.
Doerfler, P. A. et al. "Copackaging of Multiple Adeno-Associated Viral Vectors in a Single Production Step" *Human Gene Therapy Methods*, Oct. 2014, pp. 269-276, vol. 25, No. 5.
Sun, B. et al. "Enhanced Efficacy of an AAV Vector Encoding Chimeric, Highly Secreted Acid α-Glucosidase in Glycogen Storage Disease Type II" *Molecular Therapy*, Dec. 2006, pp. 822-830, vol. 14, No. 6.
Written Opinion in International Application No. PCT/EP2017/072944, dated Dec. 4, 2017, pp. 1-7.
Corti, M. et al. "Evaluation of Readministration of a Recombinant Adeno-Associated Virus Vector Expressing Acid Alpha-Glucosidase in Pompe Disease: Preclinical to Clinical Planning" *Human Gene Therapy Clinical Development*, Sep. 2015, pp. 185-193, vol. 26, No. 3.

(Continued)

*Primary Examiner* — Maryam Monshipouri
(74) *Attorney, Agent, or Firm* — Saliwanchik, Lloyd & Eisenschenk

(57) ABSTRACT

The present invention relates to variants of acid-alpha glucosidase and uses thereof.

Figure 1:
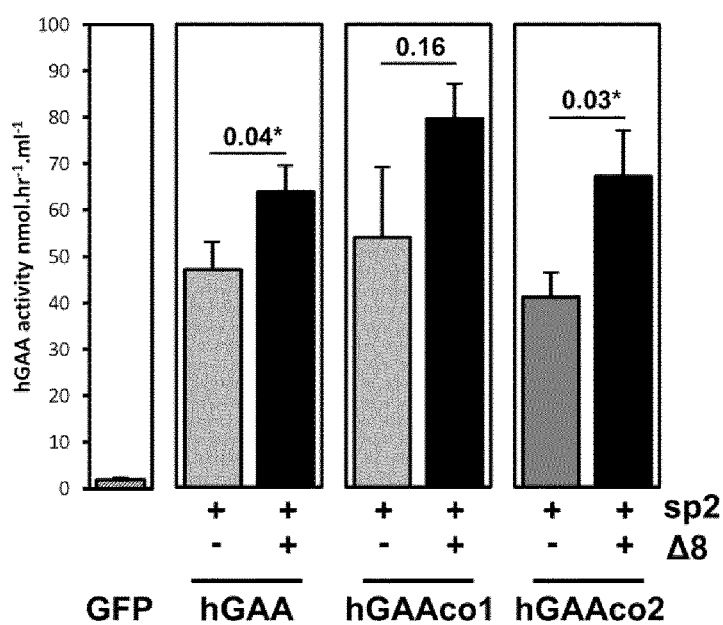
Figure 1:
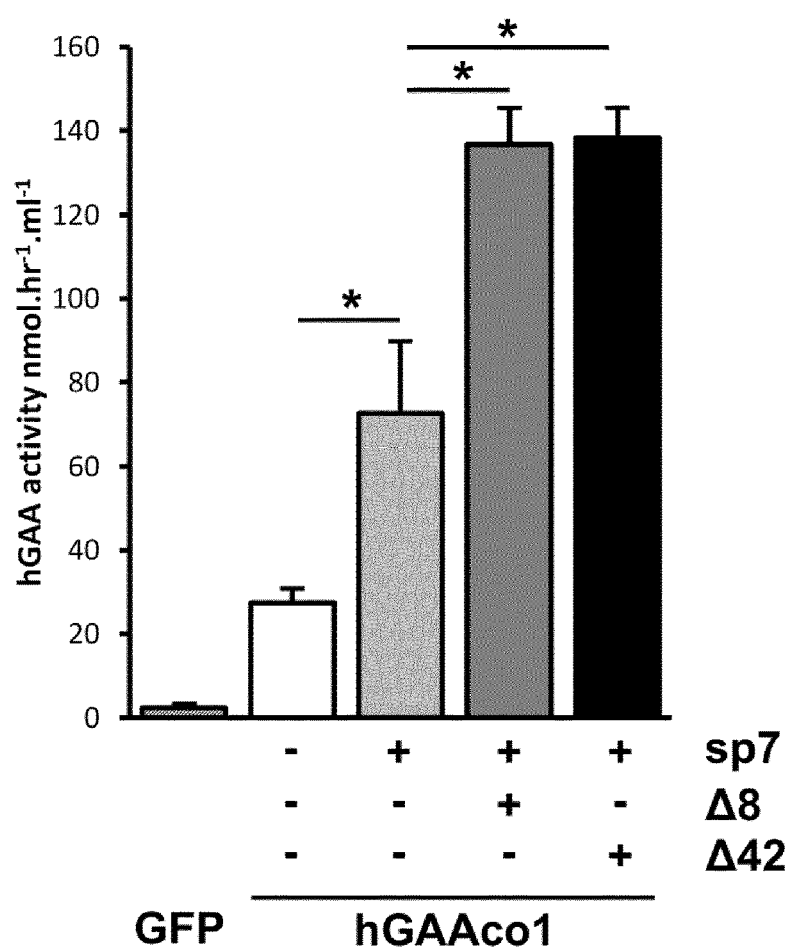

20 Claims, 10 Drawing Sheets
Specification includes a Sequence Listing.

(56) References Cited

OTHER PUBLICATIONS

Doerfler, P.A. et al. "Copackaged AAV9 Vectors Promote Simultaneous Immune Tolerance and Phenotypic Correction of Pompe Disease" *Human Gene Therapy*, Jan. 2016, pp. 43-59, vol. 27, No. 1.
Lu, J.Z. et al. "Genetic Engineering of a Bifunctional IgG Fusion Protein with Iduronate-2-Sulfatase" *Bioconjugate Chem.*, 2010, pp. 151-156, vol. 21, No. 1.
Database Accession No. BAW43522, Dec. 5, 2013, XP-002767220, pp. 1-3.

\* cited by examiner

SEQUENCE LISTING

```
<160> NUMBER OF SEQ ID NOS: 53

<210> SEQ ID NO 1
<211> LENGTH: 925
<212> TYPE: PRT
<213> ORGANISM: artificial
<220> FEATURE:
<223> OTHER INFORMATION: hGAAwt w/o sp

<400> SEQUENCE: 1

Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
    50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                85                  90                  95

Gln Pro Trp Cys Phe Phe Pro Pro Ser Tyr Pro Ser Tyr Lys Leu Glu
            100                 105                 110

Asn Leu Ser Ser Ser Glu Met Gly Tyr Thr Ala Thr Leu Thr Arg Thr
        115                 120                 125

Thr Pro Thr Phe Phe Pro Lys Asp Ile Leu Thr Leu Arg Leu Asp Val
    130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro His Val His Ser Arg
                165                 170                 175

Ala Pro Ser Pro Leu Tyr Ser Val Glu Phe Ser Glu Glu Pro Phe Gly
```

```
                180                 185                 190
Val Ile Val Arg Arg Gln Leu Asp Gly Arg Val Leu Leu Asn Thr Thr
            195                 200                 205
Val Ala Pro Leu Phe Phe Ala Asp Gln Phe Leu Gln Leu Ser Thr Ser
            210                 215                 220
Leu Pro Ser Gln Tyr Ile Thr Gly Leu Ala Glu His Leu Ser Pro Leu
225                 230                 235                 240
Met Leu Ser Thr Ser Trp Thr Arg Ile Thr Leu Trp Asn Arg Asp Leu
                245                 250                 255
Ala Pro Thr Pro Gly Ala Asn Leu Tyr Gly Ser His Pro Phe Tyr Leu
            260                 265                 270
Ala Leu Glu Asp Gly Gly Ser Ala His Gly Val Phe Leu Leu Asn Ser
            275                 280                 285
Asn Ala Met Asp Val Val Leu Gln Pro Ser Pro Ala Leu Ser Trp Arg
            290                 295                 300
Ser Thr Gly Gly Ile Leu Asp Val Tyr Ile Phe Leu Gly Pro Glu Pro
305                 310                 315                 320
Lys Ser Val Val Gln Gln Tyr Leu Asp Val Val Gly Tyr Pro Phe Met
                325                 330                 335
Pro Pro Tyr Trp Gly Leu Gly Phe His Leu Cys Arg Trp Gly Tyr Ser
                340                 345                 350
Ser Thr Ala Ile Thr Arg Gln Val Val Glu Asn Met Thr Arg Ala His
            355                 360                 365
Phe Pro Leu Asp Val Gln Trp Asn Asp Leu Asp Tyr Met Asp Ser Arg
            370                 375                 380
Arg Asp Phe Thr Phe Asn Lys Asp Gly Phe Arg Asp Phe Pro Ala Met
385                 390                 395                 400
Val Gln Glu Leu His Gln Gly Gly Arg Arg Tyr Met Met Ile Val Asp
                405                 410                 415
Pro Ala Ile Ser Ser Ser Gly Pro Ala Gly Ser Tyr Arg Pro Tyr Asp
                420                 425                 430
Glu Gly Leu Arg Arg Gly Val Phe Ile Thr Asn Glu Thr Gly Gln Pro
            435                 440                 445
Leu Ile Gly Lys Val Trp Pro Gly Ser Thr Ala Phe Pro Asp Phe Thr
450                 455                 460
Asn Pro Thr Ala Leu Ala Trp Trp Glu Asp Met Val Ala Glu Phe His
465                 470                 475                 480
Asp Gln Val Pro Phe Asp Gly Met Trp Ile Asp Met Asn Glu Pro Ser
                485                 490                 495
Asn Phe Ile Arg Gly Ser Glu Asp Gly Cys Pro Asn Asn Glu Leu Glu
                500                 505                 510
Asn Pro Pro Tyr Val Pro Gly Val Val Gly Gly Thr Leu Gln Ala Ala
            515                 520                 525
Thr Ile Cys Ala Ser Ser His Gln Phe Leu Ser Thr His Tyr Asn Leu
530                 535                 540
His Asn Leu Tyr Gly Leu Thr Glu Ala Ile Ala Ser His Arg Ala Leu
545                 550                 555                 560
Val Lys Ala Arg Gly Thr Arg Pro Phe Val Ile Ser Arg Ser Thr Phe
                565                 570                 575
Ala Gly His Gly Arg Tyr Ala Gly His Trp Thr Gly Asp Val Trp Ser
                580                 585                 590
Ser Trp Glu Gln Leu Ala Ser Ser Val Pro Glu Ile Leu Gln Phe Asn
                595                 600                 605
```

Leu Leu Gly Val Pro Leu Val Gly Ala Asp Val Cys Gly Phe Leu Gly
610                 615                 620

Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
                645                 650                 655

Pro Tyr Ser Phe Ser Glu Pro Ala Gln Gln Ala Met Arg Lys Ala Leu
                660                 665                 670

Thr Leu Arg Tyr Ala Leu Leu Pro His Leu Tyr Thr Leu Phe His Gln
            675                 680                 685

Ala His Val Ala Gly Glu Thr Val Ala Arg Pro Leu Phe Leu Glu Phe
690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
                725                 730                 735

Thr Gly Tyr Phe Pro Leu Gly Thr Trp Tyr Asp Leu Gln Thr Val Pro
                740                 745                 750

Val Glu Ala Leu Gly Ser Leu Pro Pro Pro Ala Ala Pro Arg Glu
            755                 760                 765

Pro Ala Ile His Ser Glu Gly Gln Trp Val Thr Leu Pro Ala Pro Leu
770                 775                 780

Asp Thr Ile Asn Val His Leu Arg Ala Gly Tyr Ile Ile Pro Leu Gln
785                 790                 795                 800

Gly Pro Gly Leu Thr Thr Thr Glu Ser Arg Gln Gln Pro Met Ala Leu
                805                 810                 815

Ala Val Ala Leu Thr Lys Gly Gly Glu Ala Arg Gly Glu Leu Phe Trp
                820                 825                 830

Asp Asp Gly Glu Ser Leu Glu Val Leu Glu Arg Gly Ala Tyr Thr Gln
            835                 840                 845

Val Ile Phe Leu Ala Arg Asn Asn Thr Ile Val Asn Glu Leu Val Arg
850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
                885                 890                 895

Ser Asn Phe Thr Tyr Ser Pro Asp Thr Lys Val Leu Asp Ile Cys Val
                900                 905                 910

Ser Leu Leu Met Gly Glu Gln Phe Leu Val Ser Trp Cys
915                 920                 925

<210> SEQ ID NO 2
<211> LENGTH: 952
<212> TYPE: PRT
<213> ORGANISM: homo sapiens

<400> SEQUENCE: 2

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly

-continued

```
                50                  55                  60
Pro Arg Asp Ala Gln Ala His Pro Gly Arg Pro Arg Ala Val Pro Thr
 65                  70                  75                  80

Gln Cys Asp Val Pro Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480
```

```
Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895
```

```
Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 3
<211> LENGTH: 18
<212> TYPE: PRT
<213> ORGANISM: artificial
<220> FEATURE:
<223> OTHER INFORMATION: sp7

<400> SEQUENCE: 3

Met Ala Phe Leu Trp Leu Leu Ser Cys Trp Ala Leu Leu Gly Thr Thr
1               5                   10                  15

Phe Gly

<210> SEQ ID NO 4
<211> LENGTH: 27
<212> TYPE: PRT
<213> ORGANISM: artificial
<220> FEATURE:
<223> OTHER INFORMATION: sp1

<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu
            20                  25

<210> SEQ ID NO 5
<211> LENGTH: 24
<212> TYPE: PRT
<213> ORGANISM: artificial
<220> FEATURE:
<223> OTHER INFORMATION: sp2

<400> SEQUENCE: 5

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 6
<211> LENGTH: 25
<212> TYPE: PRT
<213> ORGANISM: artificial
<220> FEATURE:
<223> OTHER INFORMATION: sp6

<400> SEQUENCE: 6

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 7
<211> LENGTH: 22
<212> TYPE: PRT
```

```
<213> ORGANISM: artificial
<220> FEATURE:
<223> OTHER INFORMATION: sp8

<400> SEQUENCE: 7

Met Ala Ser Arg Leu Thr Leu Leu Thr Leu Leu Leu Leu Leu Leu Ala
1               5                   10                  15

Gly Asp Arg Ala Ser Ser
            20

<210> SEQ ID NO 8
<211> LENGTH: 2859
<212> TYPE: DNA
<213> ORGANISM: homo sapiens

<400> SEQUENCE: 8
```

| | | | | | |
|---|---|---|---|---|---|
| atgggagtga | ggcacccgcc | ctgctcccac | cggctcctgg | ccgtctgcgc | cctcgtgtcc | 60 |
| ttggcaaccg | cagcgctcct | ggggcacatc | ctactccatg | atttcctgct | ggttccccga | 120 |
| gagctgagtg | gctcctcccc | agtcctggag | gagactcacc | cagctcacca | gcagggagcc | 180 |
| agcagaccag | gccccgggga | tgcccaggca | caccccgggc | ggccgcgagc | agtgcccaca | 240 |
| cagtgcgacg | tccccccaa | cagccgcttc | gattgcgccc | ctgacaaggc | catcacccag | 300 |
| gaacagtgcg | aggcccgcgg | ctgttgctac | atccctgcaa | gcaggggct | gcaggagcc | 360 |
| cagatggggc | agccctggtg | cttcttccca | cccagctacc | ccagctacaa | gctggagaac | 420 |
| ctgagctcct | ctgaaatggg | ctacacggcc | accctgaccc | gtaccacccc | caccttcttc | 480 |
| cccaaggaca | tcctgacccct | gcggctggac | gtgatgatgg | agactgagaa | ccgcctccac | 540 |
| ttcacgatca | aagatccagc | taacaggcgc | tacgaggtgc | ccttggagac | ccgcatgtc | 600 |
| cacagccggg | caccgtcccc | actctacagc | gtggagttct | ccgaggagcc | cttcggggtg | 660 |
| atcgtgcgcc | ggcagctgga | cggccgcgtg | ctgctgaaca | cgacggtggc | gccctgttc | 720 |
| tttgcggacc | agttccttca | gctgtccacc | tcgctgcct | cgcagtatat | cacaggcctc | 780 |
| gccgagcacc | tcagtcccct | gatgctcagc | accagctgga | ccaggatcac | cctgtggaac | 840 |
| cgggaccttg | cgcccacgcc | cggtgcgaac | ctctacgggt | ctcacccttt | ctacctggcg | 900 |
| ctggaggacg | gcgggtcggc | acacggggtg | ttcctgctaa | acagcaatgc | catggatgtg | 960 |
| gtcctgcagc | cgagccctgc | ccttagctgg | aggtcgacag | gtgggatcct | ggatgtctac | 1020 |
| atcttcctgg | gccagagcc | caagagcgtg | gtgcagcagt | acctggacgt | tgtgggatac | 1080 |
| ccgttcatgc | cgccatactg | gggcctgggc | ttccacctgt | gccgctgggg | ctactcctcc | 1140 |
| accgctatca | cccgccaggt | ggtggagaac | atgaccaggg | cccacttccc | cctggacgtc | 1200 |
| cagtggaacg | acctggacta | catggactcc | cggagggact | tcacgttcaa | caaggatggc | 1260 |
| ttccgggact | tccggccat | ggtgcaggag | ctgcaccagg | gcggccggcg | ctacatgatg | 1320 |
| atcgtggatc | ctgccatcag | cagctcgggc | cctgccggga | gctacaggcc | ctacgacgag | 1380 |
| ggtctgcgga | gggggttttt | catcaccaac | gagaccggcc | agccgctgat | gggaaggta | 1440 |
| tggcccgggt | ccactgcctt | ccccgacttc | accaaccca | cagccctggc | ctggtgggag | 1500 |
| gacatggtgg | ctgagttcca | tgaccaggtg | ccctttcgacg | gcatgtggat | tgacatgaac | 1560 |
| gagccttcca | acttcatcag | gggctctgag | gacggctgcc | ccaacaatga | gctggagaac | 1620 |
| ccaccctacg | tgcctgggt | ggttgggggg | accctccagg | cggccaccat | ctgtgcctcc | 1680 |
| agccaccagt | ttctctccac | acactacaac | ctgcacaacc | tctacggcct | gaccgaagcc | 1740 |
| atcgcctccc | acagggcgct | ggtgaaggct | cgggggacac | gcccatttgt | gatctcccgc | 1800 |

-continued

| | |
|---|---|
| tcgaccttttg ctggccacgg ccgatacgcc ggccactgga cggggggacgt gtggagctcc | 1860 |
| tgggagcagc tcgcctcctc cgtgccagaa atcctgcagt ttaacctgct gggggtgcct | 1920 |
| ctggtcgggg ccgacgtctg cggcttcctg ggcaacacct cagaggagct gtgtgtgcgc | 1980 |
| tggacccagc tgggggcctt ctaccccttc atgcggaacc acaacagcct gctcagtctg | 2040 |
| ccccaggagc cgtacagctt cagcgagccg gcccagcagg ccatgaggaa ggccctcacc | 2100 |
| ctgcgctacg cactcctccc ccacctctac acactgttcc accaggccca cgtcgcgggg | 2160 |
| gagaccgtgg cccggcccct cttcctggag ttccccaagg actctagcac ctggactgtg | 2220 |
| gaccaccagc tcctgtgggg ggaggccctg ctcatcaccc cagtgctcca ggccgggaag | 2280 |
| gccgaagtga ctggctactt ccccttgggc acatggtacg acctgcagac ggtgccagta | 2340 |
| gaggcccttg gcagcctccc accccacct gcagctcccc gtgagccagc catccacagc | 2400 |
| gaggggcagt gggtgacgct gccggccccc ctggacacca tcaacgtcca cctccgggct | 2460 |
| gggtacatca tccccctgca gggccctggc ctcacaacca cagagtcccg ccagcagccc | 2520 |
| atggccctgg ctgtggccct gaccaagggt ggggaggccc gagggagct gttctgggac | 2580 |
| gatggagaga gcctggaagt gctggagcga ggggcctaca cacaggtcat cttcctggcc | 2640 |
| aggaataaca cgatcgtgaa tgagctggta cgtgtgacca gtgagggagc tggcctgcag | 2700 |
| ctgcagaagg tgactgtcct gggcgtggcc acggcgcccc agcaggtcct ctccaacggt | 2760 |
| gtccctgtct ccaacttcac ctacagcccc gacaccaagg tcctggacat ctgtgtctcg | 2820 |
| ctgttgatgg gagagcagtt tctcgtcagc tggtgttag | 2859 |

<210> SEQ ID NO 9
<211> LENGTH: 2778
<212> TYPE: DNA
<213> ORGANISM: artificial
<220> FEATURE:
<223> OTHER INFORMATION: hGAAwt w/o sp

<400> SEQUENCE: 9

| | |
|---|---|
| gggcacatcc tactccatga tttcctgctg gttccccgag agctgagtgg ctcctcccca | 60 |
| gtcctggagg agactcaccc agctcaccag cagggagcca gcagaccagg gccccgggat | 120 |
| gcccaggcac accccgggcg gccgcgagca gtgcccacac agtgcgacgt ccccccccaac | 180 |
| agccgcttcg attgcgcccc tgacaaggcc atcacccagg aacagtgcga ggcccgcggc | 240 |
| tgttgctaca tccctgcaaa gcaggggctg cagggagccc agatggggca gccctggtgc | 300 |
| ttcttcccac ccagctaccc cagctacaag ctggagaacc tgagctcctc tgaaatgggc | 360 |
| tacacggcca ccctgacccg taccaccccc accttcttcc ccaaggacat cctgacccctg | 420 |
| cggctgacag tgatgatgga gactgagaac cgcctccact tcacgatcaa agatccagct | 480 |
| aacaggcgct acgaggtgcc cttggagacc ccgcatgtcc acagccgggc accgtcccca | 540 |
| ctctacagcg tggagttctc cgaggagccc ttcggggtga tcgtgcgccg gcagctggac | 600 |
| ggccgcgtgc tgctgaacac gacggtggcg cccctgttct ttgcggacca gttccttcag | 660 |
| ctgtccacct cgctgccctc gcagtatatc acaggcctcg ccgagcacct cagtcccctg | 720 |
| atgctcagca ccagctggac caggatcacc ctgtggaacc gggaccttgc gcccacgccc | 780 |
| ggtgcgaacc tctacgggtc tcacccttc tacctggcgc tggaggacgg cgggtcggca | 840 |
| cacgggggtgt tcctgctaaa cagcaatgcc atggatgtgg tcctgcagcc gagccctgcc | 900 |
| cttagctgga gagtcgacag tgggatcctg gatgtctaca tcttcctggg cccagagccc | 960 |

```
aagagcgtgg tgcagcagta cctggacgtt gtgggatacc cgttcatgcc gccatactgg    1020
ggcctgggct tccacctgtg ccgctggggc tactcctcca ccgctatcac ccgccaggtg    1080
gtggagaaca tgaccagggc ccacttcccc ctggacgtcc agtggaacga cctggactac    1140
atggactccc ggagggactt cacgttcaac aaggatggct ccggggactt cccggccatg    1200
gtgcaggagc tgcaccaggg cggccggcgc tacatgatga tcgtggatcc tgccatcagc    1260
agctcgggcc ctgccgggag ctacaggccc tacgacgagg tctgcggag ggggttttc     1320 atcaccaacg agaccggcca gccgctgatt gggaaggtat ggcccgggtc cactgccttc    1380
cccgacttca ccaaccccac agccctggcc tggtgggagg acatggtggc tgagttccat    1440
gaccaggtgc ccttcgacgg catgtggatt gacatgaacg agccttccaa cttcatcagg    1500
ggctctgagg acggctgccc caacaatgag ctggagaacc caccctacgt gcctggggtg    1560
gttgggggga ccctccaggc ggccaccatc tgtgcctcca gccaccagtt tctctccaca    1620
cactacaacc tgcacaacct ctacggcctg accgaagcca tcgcctccca cagggcgctg    1680
gtgaaggctc gggggacacg cccatttgtg atctcccgct cgacctttgc tggccacggc    1740
cgatacgccg gccactggac ggggacgtg tggagctcct gggagcagct cgcctcctcc    1800
gtgccagaaa tcctgcagtt taacctgctg ggggtgcctc tggtcgggc cgacgtctgc    1860 ggcttcctgg gcaacacctc agaggagctg tgtgtgcgct ggaccagct ggggccttc    1920 taccccttca tgcggaacca aacagcctg ctcagtctgc cccaggagcc gtacagcttc    1980
agcgagccgg cccagcaggc catgaggaag ccctcaccc tgcgctacgc actcctcccc    2040
cacctctaca cactgttcca ccaggcccac gtcgcgggg agaccgtggc ccggcccctc    2100
ttcctggagt tccccaagga ctctagcacc tggactgtgg accaccagct cctgtggggg    2160
gaggccctgc tcatcacccc agtgctccag gccgggaagg ccgaagtgac tggctacttc    2220
cccttgggca catggtacga cctgcagacg gtgccagtag aggcccttgg cagcctccca    2280
cccccacctg cagctccccg tgagccagcc atccacagcg aggggcagtg ggtgacgctg    2340
ccggcccccc tggacaccat caacgtccac ctccgggctg gtacatcat ccccctgcag    2400 ggccctggcc tcacaaccac agagtcccgc cagcagccca tggccctggc tgtggccctg    2460
accaagggtg gggaggcccg aggggagctg ttctgggacg atggagagag cctggaagtg    2520
ctggagcgag gggcctacac acaggtcatc ttcctggcca ggaataacac gatcgtgaat    2580
gagctggtac gtgtgaccag tgagggagct ggcctgcagc tgcagaaggt gactgtcctg    2640
ggcgtggcca cggcgcccca gcaggtcctc tccaacggtg tccctgtctc caacttcacc    2700
tacagccccg acaccaaggt cctggacatc tgtgtctcgc tgttgatggg agagcagttt    2760
ctcgtcagct ggtgttag                                                 2778

<210> SEQ ID NO 10
<211> LENGTH: 2778
<212> TYPE: DNA
<213> ORGANISM: artificial
<220> FEATURE:
<223> OTHER INFORMATION: hGAAco1 w/o sp

<400> SEQUENCE: 10
ggccatatcc tgctgcacga ctttctacta gtgcccagag agctgagcgg cagctctccc      60
gtgctggaag aaacacaccc tgcccatcag cagggcgcct ctagacctgg acctagagat     120
gcccaggccc accccggcag acctagagct gtgcctaccg agtgtgacgt gccccccaac     180
agcagattcg actgcgcccc tgacaaggcc atcacccagg aacagtgcga ggccagaggc     240
```

```
tgctgctaca tccctgccaa gcagggactg cagggcgctc agatgggaca gccctggtgc    300
ttcttcccac cctcctaccc cagctacaag ctggaaaacc tgagcagcag cgagatgggc    360
tacaccgcca ccctgaccag aaccacccc acattcttcc caaaggacat cctgaccctg     420
cggctggacg tgatgatgga aaccgagaac cggctgcact tcaccatcaa ggaccccgcc    480
aatcggagat acgaggtgcc cctggaaacc ccccacgtgc actctagagc ccccagccct    540
ctgtacagcg tggaattcag cgaggaaccc ttcggcgtga tcgtgcggag acagctggat    600
ggcagagtgc tgctgaacac caccgtggcc cctctgttct cgccgacca gttcctgcag     660 ctgagcacca gcctgcccag ccagtacatc acaggactgg ccgagcacct gagcccctg     720 atgctgagca tcctggac ccggatcacc ctgtggaaca gggatctggc ccctacccct      780
ggcgccaatc tgtacggcag ccacccttc tacctggccc tggaagatgg cggatctgcc    840
cacggagtgt ttctgctgaa ctccaacgcc atggacgtgg tgctgcagcc tagccctgcc    900
ctgtcttgga aagcacagg cggcatcctg gatgtgtaca ctttctggg ccccgagccc     960 aagagcgtgg tgcagcagta tctggatgtc gtgggctacc ccttcatgcc cccttactgg    1020
ggcctgggat ccacctgtg cagatggggc tactccagca ccgccatcac cagacaggtg    1080
gtggaaaaca tgaccagagc ccacttccca ctggatgtgc agtggaacga cctggactac    1140
atggacagca acgggacttt caccttcaac aaggacggct ccgggacttt ccccgccatg    1200
gtgcaggaac tgcatcaggg cggcagacgg tacatgatga tcgtggatcc cgccatcagc    1260
tcctctggcc ctgccggctc ttacagaccc tacgacgagg cctgcggag aggcgtgttc    1320 atcaccaacg agacaggcca gccctgatc ggcaaagtgt ggcctggcag cacagccttc    1380
cccgacttca ccaatcctac cgccctggct tggtgggagg acatggtggc cgagttccac    1440
gaccaggtgc ccttcgacgg catgtggatc gacatgaacg agcccagcaa cttcatccgg    1500
ggcagcgagg atggctgccc caacaacgaa ctggaaaatc cccttacgt gcccggcgtc    1560 gtgggcggaa cactgcaggc cgctacaatc tgtgccagca gccaccagtt tctgagcacc    1620
cactacaacc tgcacaacct gtacggcctg accgaggcca ttgccagcca ccgcgctctc    1680
gtgaaagcca gaggcacacg gcccttcgtg atcagcagaa gcacctttgc cggccacggc    1740
agatacgccg acattggac tggcgacgtg tggtcctctt gggagcagct ggcctctagc    1800
gtgcccgaga tcctgcagtt caatctgctg gcgtgccac tcgtgggcgc cgatgtgtgt    1860
ggcttcctgg gcaacacctc cgaggaactg tgtgtgcggt ggacacagct gggcgccttc    1920 tacccttca tgagaaaacca aacagcctg ctgagcctgc cccaggaacc ctacagcttt     1980
agcgagcctg cacagcaggc catgcggaag gccctgacac tgagatacgc tctgctgccc    2040
cacctgtaca ccctgtttca ccaggccat gtggccggcg agacagtggc cagacctctg    2100
tttctggaat cccccaagga cagcagcacc tggaccgtgg accatcagct gctgtgggga    2160
gaggctctgc tgattacccc agtgctgcag gcaggcaagg ccgaagtgac cggctacttt    2220
cccctgggca cttggtacga cctgcagacc gtgcctgtgg aagccctggg atctctgcct    2280
ccacctcctg ccgctcctag agagcctgcc attcactctg agggccagtg ggtcacactg    2340 cctgccccc tggataccat caacgtgcac ctgagggccg gctacatcat accactgcag    2400
ggacctggcc tgaccaccac cgagtctaga cagcagccaa tggccctggc cgtggccctg    2460
accaaaggcg agaagctag ggcgagctg ttctgggacg atggcgagag cctggaagtg     2520
ctggaaagag gcgcctatac ccaagtgatc ttcctggccc ggaacaacac catcgtgaac    2580
```

| | |
|---|---|
| gagctggtgc gcgtgacctc tgaaggcgct ggactgcagc tgcagaaagt gaccgtgctg | 2640 |
| ggagtggcca cagcccctca gcaggtgctg tctaatggcg tgcccgtgtc caacttcacc | 2700 |
| tacagccccg acaccaaggt gctggacatc tgcgtgtcac tgctgatggg agagcagttt | 2760 |
| ctggtgtcct ggtgctga | 2778 |

```
<210> SEQ ID NO 11
<211> LENGTH: 2778
<212> TYPE: DNA
<213> ORGANISM: artificial
<220> FEATURE:
<223> OTHER INFORMATION: hGAAco2 w/o sp

<400> SEQUENCE: 11
```

| | |
|---|---|
| ggacacatcc tgctgcacga cttcctgttg gtgcctagag agctgagcgg atcatcccca | 60 |
| gtgctggagg agactcatcc tgctcaccaa cagggagctt ccagaccagg accgagagac | 120 |
| gcccaagccc atcctggtag accaagagct gtgcctaccc aatgcgacgt gccacccaac | 180 |
| tcccgattcg actgcgcgcc agataaggct attacccaag agcagtgtga agccagaggt | 240 |
| tgctgctaca tcccagcgaa gcaaggattg caaggcgccc aaatgggaca accttggtgt | 300 |
| ttcttcccccc cttcgtaccc atcatataaa ctcgaaaacc tgtcctcttc ggaaatgggt | 360 |
| tatactgcca ccctcaccag aactactcct actttcttcc cgaaagacat cttgaccttg | 420 |
| aggctggacg tgatgatgga gactgaaaac cggctgcatt tcactatcaa agatcctgcc | 480 |
| aatcggcgat acgaggtccc tctggaaacc cctcacgtgc actcacgggc tccttctccg | 540 |
| ctttactccg tcgaattctc tgaggaaccc ttcggagtga tcgttagacg ccagctggat | 600 |
| ggtagagtgc tgttgaacac tactgtggcc ccactttttct tcgctgacca gtttctgcaa | 660 |
| ctgtccactt ccctgccatc ccagtacatt actggactcg ccgaacacct gtcgccactg | 720 |
| atgctctcga cctcttggac tagaatcact ttgtggaaca gagacttggc ccctactccg | 780 |
| ggagcaaatc tgtacggaag ccacccttt tacctggcgc tcgaagatgg cggatccgct | 840 |
| cacggagtgt tcctgctgaa tagcaacgca atggacgtgg tgctgcaacc ttcccctgca | 900 |
| ctcagttgga gaagtaccgg gggtattctg gacgtgtaca tcttcctcgg accagaaccc | 960 |
| aagagcgtgg tgcagcaata tctggacgtg gtcggatacc ctttatgcc tccttactgg | 1020 |
| ggactgggat ccaccttttg ccgttggggc tactcatcca ccgccattac agacaggtg | 1080 |
| gtggagaata tgaccagagc ccacttccct ctcgacgtgc agtggaacga tctggactat | 1140 |
| atggactccc ggagagattt caccttcaac aaggacgggt ccgcgatt tcccgcgatg | 1200 |
| gttcaagagc tccaccaggg tggtcgaaga tatatgatga tcgtcgaccc agccatttcg | 1260 |
| agcagcggac ccgctggatc ttatagacct tacgacgaag ccttaggag aggagtgttc | 1320 |
| atcacaaacg agactggaca gcctttgatc ggtaaagtgt ggcctggatc aaccgccttt | 1380 |
| cctgactta ccaatcccac tgccttggct tggtgggagg acatggtggc cgaattccac | 1440 |
| gaccaagtcc cctttgatgg aatgtggatc gatatgaacg aaccaagcaa ttttatcaga | 1500 |
| ggttccgaag acggttgccc caacaacgaa ctggaaaacc ctccttatgt gcccggagtc | 1560 |
| gtgggcggaa cattacaggc cgcgactatt gcgccagca gccaccaatt cctgtccact | 1620 |
| cactacaacc tccacaacct ttatggatta accgaagcta ttgcaagtca cagggctctg | 1680 |
| gtgaaggcta gagggactag gcccttgtg atctcccgat ccacctttgc cggacacggg | 1740 |
| agatacgccg tcactggac tggtgacgtg tggagctcat gggaacaact ggcctcctcc | 1800 |
| gtgccggaaa tcttacagtt caaccttctg ggtgtccctc ttgtcggagc agacgtgtgt | 1860 |

-continued

```
gggtttcttg gtaacacctc cgaggaactg tgtgtgcgct ggactcaact gggtgcattc    1920
tacccattca tgagaaacca caactccttg ctgtccctgc acaagagcc  ctactcgttc    1980 agcgagcctg cacaacaggc tatgcggaag gcactgaccc tgagatacgc cctgcttcca    2040
cacttataca ctctcttcca tcaagcgcat gtggcaggag aaaccgttgc aaggcctctt    2100
ttccttgaat tccccaagga ttcctcgact tggacggtgg atcatcagct gctgtgggga    2160
gaagctctgc tgattactcc agtgttgcaa gccggaaaag ctgaggtgac cggatacttt    2220
ccgctgggaa cctggtacga cctccagact gtccctgttg aagcccttgg atcactgcct    2280
ccgcctccgg cagctccacg cgaaccagct atacattccg agggacagtg ggttacatta    2340
ccagctcctc tggacacaat caacgtccac ttaagagctg gctacattat ccctctgcaa    2400
ggaccaggac tgactacgac cgagagcaga cagcagccaa tggcactggc tgtggctctg    2460
accaagggag gggaagctag aggagaactc ttctgggatg atggggagtc ccttgaagtg    2520
ctggaaagag gcgcttacac tcaagtcatt ttccttgcac ggaacaacac cattgtgaac    2580
gaattggtgc gagtgaccag cgaaggagct ggacttcaac tgcagaaggt cactgtgctc    2640
ggagtggcta ccgctcctca gcaagtgctg tcgaatggag tccccgtgtc aaactttacc    2700
tactcccctg acactaaggt gctcgacatt tgcgtgtccc cctgatgggg agagcagttc    2760
cttgtgtcct ggtgttga                                                 2778

<210> SEQ ID NO 12
<211> LENGTH: 2754
<212> TYPE: DNA
<213> ORGANISM: artificial
<220> FEATURE:
<223> OTHER INFORMATION: hGAAco1-delta-8 w/o sp

<400> SEQUENCE: 12
ctactagtgc ccagagagct gagcggcagc tctcccgtgc tggaagaaac acaccctgcc      60
catcagcagg gcgcctctag acctggacct agagatgccc aggcccaccc cggcagacct     120
agagctgtgc ctacccagtg tgacgtgccc cccaacagca gattcgactg cgcccctgac     180
aaggccatca cccaggaaca gtgcgaggcc agaggctgct gctacatccc tgccaagcag     240
ggactgcagg gcgctcagat gggacagccc tggtgcttct tcccaccctc ctacccagc     300 tacaagctgg aaaacctgag cagcagcgag atgggctaca ccgccaccct gaccagaacc     360 accccccacat tcttcccaaa ggacatcctg accctgcggc tggacgtgat gatggaaacc     420
gagaaccggc tgcacttcac catcaaggac cccgccaatc ggagatacga ggtgcccctg     480
gaaacccccc acgtgcactc tagagccccc agccctctgt acagcgtgga attcagcgag     540 gaaccttcg  cgcgtgatcgt gcggagacag ctggatggca gagtgctgct gaacaccacc     600
gtggcccctc tgttcttcgc cgaccagttc ctgcagctga gcaccagcct gcccagccag     660
tacatcacag gactggccga gcacctgagc cccctgatgc tgagcacatc ctggacccgg     720
atcaccctgt ggaacaggga tctggccccct accctggcg  ccaatctgta cggcagccac     780
cctttctacc tggccctgga agatggcgga tctgcccacg gagtgttct  gctgaactcc     840 aacgccatgg acgtggtgct gcagcctagc cctgccctgt cttggagaag cacaggcggc     900
atcctggatg tgtacatctt tctgggcccc gagcccaaga gcgtggtgca gcagtatctg     960
gatgtcgtgg gctaccccct tcatgccccct tactggggcc tgggattcca cctgtgcaga    1020
tggggctact ccagcaccgc catcaccaga caggtggtgg aaaacatgac cagagcccac    1080
```

```
ttcccactgg atgtgcagtg gaacgacctg gactacatgg acagcagacg ggacttcacc    1140
ttcaacaagg acggcttccg ggacttcccc gccatggtgc aggaactgca tcagggcggc    1200
agacggtaca tgatgatcgt ggatcccgcc atcagctcct ctggccctgc cggctcttac    1260
agaccctacg acgagggcct gcggagaggc gtgttcatca ccaacgagac aggccagccc    1320
ctgatcggca aagtgtggcc tggcagcaca gccttccccg acttcaccaa tcctaccgcc    1380
ctggcttggt gggaggacat ggtggccgag ttccacgacc aggtgccctt cgacggcatg    1440
tggatcgaca tgaacgagcc cagcaacttc atccggggca gcgaggatgg ctgccccaac    1500
aacgaactgg aaaatccccc ttacgtgccc ggcgtcgtgg gcggaacact gcaggccgct    1560
acaatctgtg ccagcagcca ccagtttctg agcacccact acaacctgca aacctgtac     1620
ggcctgaccg aggccattgc cagccaccgc gctctcgtga agccagagg cacacggccc      1680
ttcgtgatca gcagaagcac ctttgccggc acggcagat acgccggaca ttggactggc     1740
gacgtgtggt cctcttggga gcagctggcc tctagcgtgc ccagatcct gcagttcaat     1800
ctgctgggcg tgccactcgt gggcgccgat gtgtgtggct tcctgggcaa cacctccgag    1860
gaactgtgtg tgcggtggac acagctgggc gccttctacc ctttcatgag aaaccacaac    1920
agcctgctga gctgcccca ggaaccctac agctttagcg agcctgcaca gcaggccatg     1980
cggaaggccc tgacactgag atacgctctg ctgccccacc tgtacaccct gtttcaccag    2040
gcccatgtgg ccggcgagac agtggccaga cctctgtttc tggaattccc caaggacagc    2100
agcacctgga ccgtggacca tcagctgctg tggggagagg ctctgctgat taccccagtg    2160
ctgcaggcag gcaaggccga agtgaccggc tactttcccc tgggcacttg gtacgacctg    2220
cagaccgtgc ctgtggaagc cctgggatct ctgcctccac ctcctgccgc tcctagagag    2280
cctgccattc actctgaggg ccagtgggtc acactgctg cccccctgga taccatcaac    2340
gtgcacctga ggccggcta catcataca ctgcagggac ctggcctgac caccaccgag     2400
tctagacagc agccaatggc cctggccgtg ccctgacca aaggcggaga agctagggc     2460
gagctgttct gggacgatgg cgagagcctg gaagtgctgg aaagaggcgc ctatacccaa    2520
gtgatcttcc tggcccggaa caacaccatc gtgaacgagc tggtgcgcgt gacctctgaa    2580
ggcgctggac tgcagctgca gaaagtgacc gtgctgggag tggccacagc ccctcagcag    2640
gtgctgtcta tggcgtgcc cgtgtccaac ttcacctaca gccccgacac caaggtgctg    2700
gacatctgcg tgtcactgct gatgggagag cagtttctgg tgtcctggtg ctga          2754

<210> SEQ ID NO 13
<211> LENGTH: 2754
<212> TYPE: DNA
<213> ORGANISM: artificial
<220> FEATURE:
<223> OTHER INFORMATION: hGAAco2-delta8 w/o sp

<400> SEQUENCE: 13
ctgttggtgc ctagagagct gagcggatca tcccagtgc tggaggagac tcatcctgct      60
caccaacagg gagcttccag accaggaccg agagacgccc aagcccatcc tggtagacca    120
agagctgtgc ctaccaatg cgacgtgcca cccaactccc gattcgactg cgcgccagat    180
aaggctatta cccaagagca gtgtgaagcc agaggttgct gctacatccc agcgaagcaa    240
ggattgcaag cgcccaaat gggacaacct tggtgtttct tccccccttc gtacccatca    300
tataaactcg aaaacctgtc ctcttccgaa atgggttata ctgccaccct caccagaact    360
actcctactt tcttcccgaa agacatcttg accttgaggc tggacgtgat gatggagact    420
```

```
gaaaaccggc tgcatttcac tatcaaagat cctgccaatc ggcgatacga ggtccctctg      480
gaaacccctc acgtgcactc acgggctcct tctccgcttt actccgtcga attctctgag      540
gaacccttcg gagtgatcgt tagacgccag ctggatggta gagtgctgtt gaacactact      600 gtggcccac ttttcttcgc tgaccagttt ctgcaactgt ccacttccct gccatcccag       660
tacattactg gactcgccga acacctgtcg ccactgatgc tctcgacctc ttggactaga      720
atcactttgt ggaacagaga cttggcccct actccgggag caaatctgta cggaagccac      780 ccttttacc tggcgctcga agatggcgga tccgctcacg gagtgttcct gctgaatagc      840
aacgcaatgg acgtggtgct gcaaccttcc cctgcactca gttggagaag taccgggggt      900
attctggacg tgtacatctt cctcggacca gaacccaaga gcgtggtgca gcaatatctg      960
gacgtggtcg gataccctt tatgcctcct tactggggac tgggattcca cctttgccgt      1020
tggggctact catccaccgc cattaccaga caggtggtgg agaatatgac cagagcccac      1080
ttccctctcg acgtgcagtg gaacgatctg gactatatgg actcccggag agatttcacc      1140
ttcaacaagg acgggttccg cgattttccc gcgatggttc aagagctcca ccagggtggt      1200
cgaagatata tgatgatcgt cgacccagcc atttcgagca gcggacccgc tggatcttat      1260
agaccttacg acgaaggcct taggagagga gtgttcatca caaacgagac tggacagcct      1320
ttgatcggta aagtgtggcc tggatcaacc gcctttcctg actttaccaa tcccactgcc      1380
ttggcttggt gggaggacat ggtggccgaa ttccacgacc aagtccccctt tgatggaatg      1440 tggatcgata tgaacgaacc aagcaattt atcagaggtt ccgaagacgg ttgccccaac      1500
aacgaactgg aaaccctcc ttatgtgccc ggagtcgtgg gcggaacatt acaggccgcg      1560
actatttgcg ccagcagcca ccaattcctg tccactcact acaacctcca caacctttat      1620
ggattaaccg aagctattgc aagtcacagg gctctggtga aggctagagg gactaggccc      1680
tttgtgatct cccgatccac cttttgccgga cacgggagat acgccggtca ctggactggt      1740
gacgtgtgga gctcatggga acaactggcc tcctccgtgc cggaaatctt acagttcaac      1800
cttctgggtg tccctcttgt cggagcagac gtgtgtgggt ttcttggtaa cacctccgag      1860
gaactgtgtg tgcgctggac tcaactgggt gcattctacc cattcatgag aaaccacaac      1920
tccttgctgt ccctgccaca agagcctac tcgttcagcg agcctgcaca acaggctatg      1980
cggaaggcac tgaccctgag atacgccctg cttccacact atacactct cttccatcaa      2040 gcgcatgtgg caggagaaac cgttgcaagg cctctttttcc ttgaattccc caaggattcc      2100
tcgacttgga cggtggatca tcagctgctg tggggagaag ctctgctgat tactccagtg      2160
ttgcaagccg gaaaagctga ggtgaccgga tactttccgc tgggaacctg gtacgacctc      2220
cagactgtcc ctgttgaagc ccttggatca ctgcctccgc ctccggcagc tccacgcgaa      2280
ccagctatac attccgaggg acagtgggtt acattaccag ctcctctgga cacaatcaac      2340
gtccacttaa gagctggcta cattatccct ctgcaaggac caggactgac tacgaccgag      2400
agcagacagc agccaatggc actggctgtg gctctgacca agggaggggga agctagagga      2460 gaactcttct gggatgatgg ggagtccctt gaagtgctgg aaagaggcgc ttacactcaa      2520
gtcattttcc ttgcacggaa caacaccatt gtgaacgaat tggtgcgagt gaccagcgaa      2580
ggagctggac ttcaactgca gaaggtcact gtgctcggag tggctaccgc tcctcagcaa      2640
gtgctgtcga atggagtccc cgtgtcaaac tttaccctact cccctgacac taaggtgctc      2700
gacatttgcg tgtccctcct gatgggagag cagttccttg tgtcctggtg ttga            2754
```

<210> SEQ ID NO 14
<211> LENGTH: 397
<212> TYPE: DNA
<213> ORGANISM: artificial
<220> FEATURE:
<223> OTHER INFORMATION: hAAT promoter

<400> SEQUENCE: 14

```
gatcttgcta ccagtggaac agccactaag gattctgcag tgagagcaga gggccagcta      60
agtggtactc tcccagagac tgtctgactc acgccacccc ctccaccttg dacacaggac     120
gctgtggttt ctgagccagg tacaatgact cctttcggta agtgcagtgg aagctgtaca     180
ctgcccaggc aaagcgtccg ggcagcgtag gcgggcgact cagatcccag ccagtggact     240
tagcccctgt ttgctcctcc gataactggg gtgaccttgg ttaatattca ccagcagcct     300
cccccgttgc ccctctggat ccactgctta aatacgacg aggacagggc cctgtctcct     360
cagcttcagg caccaccact gacctgggac agtgaat                              397
```

<210> SEQ ID NO 15
<211> LENGTH: 321
<212> TYPE: DNA
<213> ORGANISM: artificial
<220> FEATURE:
<223> OTHER INFORMATION: ApoE control region

<400> SEQUENCE: 15

```
aggctcagag gcacacagga gtttctgggc tcaccctgcc cccttccaac ccctcagttc      60
ccatcctcca gcagctgttt gtgtgctgcc tctgaagtcc acactgaaca aacttcagcc     120
tactcatgtc cctaaaatgg gcaaacattg caagcagcaa acagcaaaca cacagccctc     180
cctgcctgct gaccttggag ctggggcaga ggtcagagac ctctctgggc ccatgccacc     240
tccaacatcc actcgacccc ttggaatttc ggtggagagg agcagaggtt gtcctggcgt     300
ggtttaggta gtgtgagagg g                                                321
```

<210> SEQ ID NO 16
<211> LENGTH: 441
<212> TYPE: DNA
<213> ORGANISM: artificial
<220> FEATURE:
<223> OTHER INFORMATION: HBB2 intron

<400> SEQUENCE: 16

```
gtacacatat tgaccaaatc agggtaattt tgcatttgta attttaaaaa atgctttctt      60
cttttaatat actttttgt ttatcttatt tctaatactt tccctaatct ctttctttca     120
gggcaataat gatacaatgt atcatgcctc tttgcaccat tctaaagaat aacagtgata     180
atttctgggt taaggcaata gcaatatttc tgcatataaa tatttctgca tataaattgt     240
aactgatgta agaggtttca tattgctaat agcagctaca atccagctac cattctgctt     300
ttattttatg gttgggataa ggctggatta ttctgagtcc aagctaggcc cttttgctaa     360
tcatgttcat acctcttatc ttcctcccac agctcctggg caacgtgctg gtctgtgtgc     420
tggcccatca ctttggcaaa g                                                441
```

<210> SEQ ID NO 17
<211> LENGTH: 441
<212> TYPE: DNA
<213> ORGANISM: artificial
<220> FEATURE:
<223> OTHER INFORMATION: modified HBB2 intron

<400> SEQUENCE: 17

```
gtacacatat tgaccaaatc agggtaattt tgcatttgta attttaaaaa atgctttctt      60
cttttaatat acttttttgt ttatcttatt tctaatactt tccctaatct ctttctttca     120
gggcaataat gatacaatgt atcatgcctc tttgcaccat tctaaagaat aacagtgata     180
atttctgggt taaggcaata gcaatatttc tgcatataaa tatttctgca tataaattgt     240
aactgatgta agaggtttca tattgctaat agcagctaca atccagctac cattctgctt     300
ttattttctg gttgggataa ggctggatta ttctgagtcc aagctaggcc ttttgctaa      360
tcttgttcat acctcttatc ttcctcccac agctcctggg caacctgctg gtctctctgc     420
tggcccatca ctttggcaaa g                                               441
```

<210> SEQ ID NO 18
<211> LENGTH: 1438
<212> TYPE: DNA
<213> ORGANISM: artificial
<220> FEATURE:
<223> OTHER INFORMATION: FIX intron

<400> SEQUENCE: 18

```
ggtttgtttc cttttttaaa atacattgag tatgcttgcc ttttagatat agaaatatct      60
gatgctgtct tcttcactaa attttgatta catgatttga cagcaatatt gaagagtcta     120
acagccagca cgcaggttgg taagtactgg ttctttgtta gctaggtttt cttcttcttc     180
attttaaaa ctaaatagat cgacaatgct tatgatgcat ttatgtttaa taaacactgt      240
tcagttcatg atttggtcat gtaattcctg ttagaaaaca ttcatctcct tggtttaaaa     300
aaattaaaag tgggaaaaca agaaatagc agaatatagt gaaaaaaaat aaccacatta      360
tttttgtttg gacttaccac tttgaaatca aatgggaaa caaaagcaca aacaatggcc      420
ttatttacac aaaaagtctg attttaagat atatgacatt tcaaggtttc agaagtatgt     480
aatgaggtgt gtctctaatt ttttaaatta tatatcttca atttaaagtt ttagttaaaa     540
cataaagatt aaccttttcat tagcaagctg ttagttatca ccaacgcttt tcatggatta    600
ggaaaaaatc attttgtctc tatgtcaaac atcttggagt tgatatttgg ggaaacacaa     660
tactcagttg agttccctag gggagaaaag cacgcttaag aattgacata agagtagga      720
agttagctaa tgcaacatat atcactttgt tttttcacaa ctacagtgac tttatgtatt     780
tcccagagga aggcatacag ggaagaaatt atcccatttg acaaacagc atgttctcac      840
aggaagcatt tatcacactt acttgtcaac tttctagaat caaatctagt agctgacagt     900
accaggatca ggggtgccaa ccctaagcac ccccagaaag ctgactggcc ctgtggttcc     960
cactccagac atgatgtcag ctgtgaaatc gacgtcgctg gaccataatt aggcttctgt    1020
tcttcaggag acatttgttc aaagtcattt gggcaaccat attctgaaaa cagcccagcc    1080
agggtgatgg atcactttgc aaagatcctc aatgagctat tttcaagtga tgacaaagtg    1140
tgaagttaac cgctcatttg agaactttct ttttcatcca aagtaaattc aaatatgatt    1200
agaaatctga ccttttatta ctggaattct cttgactaaa agtaaaattg aattttaatt    1260
cctaaatctc catgtgtata cagtactgtg gaacatcac agattttggc tccatgccct    1320
aaagagaaat tggctttcag attatttgga ttaaaaacaa agactttctt aagagatgta    1380
aaattttcat gatgttttct tttttgctaa aactaaagaa ttattctttt acatttca     1438
```

<210> SEQ ID NO 19

<211> LENGTH: 1438
<212> TYPE: DNA
<213> ORGANISM: artificial
<220> FEATURE:
<223> OTHER INFORMATION: modified FIX intron

<400> SEQUENCE: 19

```
ggtttgtttc ctttttaaa atacattgag tatgcttgcc ttttagatat agaaatatct      60
gatgctgtct tcttcactaa attttgatta catgatttga cagcaatatt gaagagtcta    120
acagccagca cgcaggttgg taagtactgg ttctttgtta gctaggtttt cttcttcttc    180
attttaaaaa ctaaatagat cgacattgct tttgttgcat ttatgtttaa taaacactgt    240
tcagttcatg atttggtcat gtaattcctg ttagaaaaca ttcatctcct tggtttaaaa    300
aaattaaaag tgggaaaaca agaaatagc agaatatagt gaaaaaaaat aaccacatta     360
ttttgtttg gacttaccac tttgaaatca aattgggaaa caaaagcaca aacaatggcc     420
ttatttacac aaaaagtctg attttaagat atatgacatt tcaaggtttc agaagtatgt    480
aatgaggtgt gtctctaatt ttttaaatta tatatcttca atttaaagtt ttagttaaaa    540
cataaagatt aacctttcat tagcaagctg ttagttatca ccaacgcttt tcatggatta    600
ggaaaaaatc attttgtctc tttgtcaaac atcttggagt tgatatttgg ggaaacacaa    660
tactcagttg agttccctag gggagaaaag cacgcttaag aattgacata agagtagga     720
agttagctat tgcaacatat atcactttgt ttttcacaa ctacagtgac ttttgtatt     780
tcccagagga aggcatacag ggaagaaatt atcccatttg acaaacagc ttgttctcac     840
aggaagcatt tatcacactt acttgtcaac tttctagaat caaatctagt agctgacagt    900
accaggatca ggggtgccaa ccctaagcac ccccagaaag ctgactggcc ctgtggttcc    960
cactccagac atgatgtcag ctgtgaaatc gacgtcgctg gaccataatt aggcttctgt   1020
tcttcaggag acatttgttc aaagtcattt gggcaaccat attctgaaaa cagcccagcc   1080
agggtgttgg atcactttgc aaagatcctc attgagctat tttcaagtgt tgacaaagtg   1140
tgaagttaac cgctcatttg agaactttct ttttcatcca agtaaattc aaatatgatt    1200
agaaatctga ccttttatta ctggaattct cttgactaaa agtaaaattg aatttttaatt  1260
cctaaatctc catgtgtata cagtactgtg ggaacatcac agattttggc tccatgccct  1320
aaagagaaat tggctttcag attatttgga ttaaaaacaa agactttctt aagagatgta  1380
aaattttctt gttgttttct tttttgctaa aactaaagaa ttattctttt acatttca    1438
```

<210> SEQ ID NO 20
<211> LENGTH: 881
<212> TYPE: DNA
<213> ORGANISM: artificial
<220> FEATURE:
<223> OTHER INFORMATION: chicken beta-globin intron

<400> SEQUENCE: 20

```
gcgggagtcg ctgcgttgcc ttcgccccgt gccccgctcc gccgccgcct cgcgccgccc     60
gccccggctc tgactgaccg cgttactccc acaggtgagc gggcgggacg gcccttctcc   120
tccgggctgt aattagcgct tggtttaatg acggcttgtt tcttttctgt ggctgcgtga   180
aagccttgag gggctccggg agggcccttt gtgcgggggg agcggctcgg gggtgcgtg    240
cgtgtgtgtg tgcgtgggga gcgccgcgtg cggctccgcg ctgcccgcg gctgtgagcg   300
ctgcgggcgc ggcgcgggc tttgtgcgct ccgcagtgtg cgcgagggga gcgcggccgg   360
gggcggtgcc ccgcggtgcg gggggggctg cgaggggaac aaaggctgcg tgcggggtgt   420
```

```
gtgcgtgggg gggtgagcag ggggtgtggg cgcgtcggtc gggctgcaac ccccctgca    480 ccccctccc  cgagttgctg agcacggccc ggcttcgggt gcggggctcc gtacggggcg    540
tggcgcgggg ctcgccgtgc cgggcggggg gtggcggcag gtgggggtgc cgggcggggc    600
ggggccgcct cgggccgggg agggctcggg ggaggggcgc ggcggccccc ggagcgccgg    660
cggctgtcga ggcgcggcga gccgcagcca ttgccttttta tggtaatcgt gcgagagggc    720
gcagggactt cctttgtccc aaatctgtgc ggagccgaaa tctggaggc gccgccgcac    780 cccctctagc gggcgcgggg cgaagcggtg cggcgccggc aggaaggaaa tgggcgggga    840
gggccttcgt gcgtcgccgc gccgccgtcc ccttctccct c                        881
```

<210> SEQ ID NO 21
<211> LENGTH: 881
<212> TYPE: DNA
<213> ORGANISM: artificial
<220> FEATURE:
<223> OTHER INFORMATION: modified chicken beta-globin intron

<400> SEQUENCE: 21

```
gcgggagtcg ctgcgttgcc ttcgcccgt  gccccgctcc gccgccgcct cgcgccgccc     60
gccccggctc tgactgaccg cgttactccc acaggtgagc gggcgggacg gcccttctcc    120
tccgggctgt aattagcgct tggtttaatg acggcttgtt tcttttctgt ggctgcgtga    180
aagccttgag gggctccggg agggcccttt gtgcgggggg agcggctcgg ggggtgcgtg    240
cgtgtgtgtg tgcgtgggga gcgccgcgtg cggctccgcg ctgcccggcg gctgtgagcg    300
ctgcgggcgc ggcgcggggc tttgtgcgct ccgcagtgtg cgcgagggga gcgcggccgg    360
gggcggtgcc ccgcggtgcg gggggggctg cgaggggaac aaaggctgcg tgcgggtgt    420 gtgcgtgggg gggtgagcag ggggtgtggg cgcgtcggtc gggctgcaac ccccctgca    480 ccccctccc  cgagttgctg agcacggccc ggcttcgggt gcggggctcc gtacggggcg    540
tggcgcgggg ctcgccgtgc cgggcggggg gtggcggcag gtgggggtgc cgggcggggc    600
ggggccgcct cgggccgggg agggctcggg ggaggggcgc ggcggccccc ggagcgccgg    660
cggctgtcga ggcgcggcga gccgcagcca ttgcctttt  tggtaatcgt gcgagagggc    720
gcagggactt cctttgtccc aaatctgtgc ggagccgaaa tctggaggc gccgccgcac    780 cccctctagc gggcgcgggg cgaagcggtg cggcgccggc aggaaggaat tgggcgggga    840
gggccttcgt gcgtcgccgc gccgccgtcc ccttctccct c                        881
```

<210> SEQ ID NO 22
<211> LENGTH: 4318
<212> TYPE: DNA
<213> ORGANISM: artificial
<220> FEATURE:
<223> OTHER INFORMATION: construct: sp2+hGAAwt-delta-8

<400> SEQUENCE: 22

```
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtacccggg gatcttgcta ccagtggaac agccactaag    360
```

```
gattctgcag tgagagcaga gggccagcta agtggtactc tcccagagac tgtctgactc    420
acgccacccc ctccaccttg gacacaggac gctgtggttt ctgagccagg tacaatgact    480
cctttcggta agtgcagtgg aagctgtaca ctgcccaggc aaagcgtccg ggcagcgtag    540
gcgggcgact cagatcccag ccagtggact tagcccctgt ttgctcctcc gataactggg    600
gtgaccttgg ttaatattca ccagcagcct ccccgttgc ccctctggat ccactgctta    660
aatacggacg aggacagggc cctgtctcct cagcttcagg caccaccact gacctgggac    720
agtgaataga tcctgagaac ttcagggtga gtctatggga cccttgatgt tttctttccc    780
cttcttttct atggttaagt tcatgtcata ggaaggggag aagtaacagg gtacacatat    840
tgaccaaatc agggtaattt tgcatttgta attttaaaaa atgctttctt cttttaatat    900
acttttttgt ttatcttatt tctaatactt tccctaatct cttctttca gggcaataat    960 gatacaatgt atcatgcctc tttgcaccat tctaaagaat aacagtgata atttctgggt   1020
taaggcaata gcaatatttc tgcatataaa tatttctgca tataaattgt aactgatgta   1080
agaggtttca tattgctaat agcagctaca atccagctac cattctgctt ttattttctg   1140
gttgggataa ggctggatta ttctgagtcc aagctaggcc cttttgctaa tcttgttcat   1200
acctcttatc ttcctcccac agctcctggg caacctgctg gtctctctgc tggcccatca   1260
ctttggcaaa gcacgcgtgc caccatgccg tcttctgtct cgtggggcat cctcctgctg   1320
gcaggcctgt gctgcctggt ccctgtctcc ctggctctgc tggttccccg agagctgagt   1380
ggctcctccc cagtcctgga ggagactcac ccagctcacc agcagggagc cagcagacca   1440
gggcccgggg atgcccaggc acaccccggg cggccgcgag cagtgcccac acagtgcgac   1500 gtcccccca acagccgctt cgattgcgcc cctgacaagg ccatcaccca ggaacagtgc   1560
gaggcccgcg gctgttgcta catccctgca aagcagggc tgcagggagc cagatgggg    1620 cagccctggt gcttcttccc acccagctac cccagctaca agctggagaa cctgagctcc   1680
tctgaaatgg gctacacggc cacccctgacc cgtaccaccc ccaccttctt ccccaaggac   1740
atcctgaccc tgcggctgga cgtgatgatg gagactgaga accgcctcca cttcacgatc   1800
aaagatccag ctaacaggcg ctacgaggtg cccttggaga cccgcatgt ccacagccgg    1860 gcaccgtccc cactctacag cgtggagttc tccgaggagc ccttcgggat gatcgtgcgc   1920
cggcagctgg acgccgcgt gctgctgaac acgacggtgg cgcccctgtt ctttgcggac   1980
cagttccttc agctgtccac ctcgctgccc tcgcagtata tcacaggcct cgccgagcac   2040
ctcagtcccc tgatgctcag caccagctgg accaggatca cctgtggaa ccgggacctt    2100 gcgcccacgc ccggtgcgaa cctctacggg tctcacccctt tctacctggc gctggaggac   2160
ggcgggtcgg cacacggggt gttcctgcta aacagcaatg ccatggatgt ggtcctgcag   2220
ccgagccctg cccttagctg gaggtcgaca ggtgggatcc tggatgtcta catcttcctg   2280
ggcccagagc ccaagagcgt ggtgcagcag tacctggacg ttgtgggata cccgttcatg   2340
ccgccatact ggggcctggg cttccacctg tgccgctggg gctactcctc caccgctatc   2400
acccgccagg tggtggagaa catgaccagg gcccacttcc cctggacgt ccagtggaac   2460 gacctggact acatggactc ccggaggac ttcacgttca acaaggatgg cttcggac     2520 ttccccggcca tggtgcagga gctgcaccag gccggccggc gctacatgat gatcgtggat   2580
cctgccatca gcagctcggg ccctgccggg agctacaggc cctacgacga gggtctgcgg   2640
aggggggttt tcatcaccaa cgagaccggc cagccgctga ttgggaaggt atggcccggg   2700
tccactgcct tccccgactt caccaacccc acagccctgg cctggtggga ggacatggtg   2760
```

-continued

| | |
|---|---|
| gctgagttcc atgaccaggt gcccttcgac ggcatgtgga ttgacatgaa cgagccttcc | 2820 |
| aacttcatca ggggctctga ggacggctgc cccaacaatg agctggagaa cccaccctac | 2880 |
| gtgcctgggg tggttggggg gaccctccag gcggccacca tctgtgcctc cagccaccag | 2940 |
| tttctctcca cacactacaa cctgcacaac ctctacggcc tgaccgaagc catcgcctcc | 3000 |
| cacagggcgc tggtgaaggc tcgggggaca cgcccatttg tgatctcccg ctcgaccttt | 3060 |
| gctggccacg gccgatacgc cggccactgg acggggacg tgtggagctc ctgggagcag | 3120 |
| ctcgcctcct ccgtgccaga atcctgcag tttaacctgc tggggtgcc tctggtcggg | 3180 |
| gccgacgtct gcggcttcct gggcaacacc tcagaggagc tgtgtgtgcg ctggacccag | 3240 |
| ctgggggcct tctaccccctt catgcggaac acaacagcc tgctcagtct gccccaggag | 3300 |
| ccgtacagct tcagcgagcc ggcccagcag gccatgagga aggccctcac cctgcgctac | 3360 |
| gcactcctcc cccacctcta cacactgttc caccaggccc acgtcgcggg ggagaccgtg | 3420 |
| gcccggcccc tcttcctgga gttccccaag gactctagca cctggactgt ggaccaccag | 3480 |
| ctcctgtggg gggaggccct gctcatcacc ccagtgctcc aggccgggaa ggccgaagtg | 3540 |
| actggctact ccccccttggg cacatggtac gacctgcaga cggtgccagt agaggccctt | 3600 |
| ggcagcctcc cacccccacc tgcagctccc cgtgagccag ccatccacag cgaggggcag | 3660 |
| tgggtgacgc tgccggcccc cctggacacc atcaacgtcc acctccgggc tgggtacatc | 3720 |
| atccccctgc agggccctgg cctcacaacc acagagtccc gccagcagcc catggccctg | 3780 |
| gctgtggccc tgaccaaggg tggggaggcc cgaggggagc tgttctggga cgatggagag | 3840 |
| agcctggaag tgctggagcg aggggcctac acacaggtca tcttcctggc caggaataac | 3900 |
| acgatcgtga atgagctggt acgtgtgacc agtgagggag ctggcctgca gctgcagaag | 3960 |
| gtgactgtcc tgggcgtggc cacggcgccc cagcaggtcc tctccaacgg tgtccctgtc | 4020 |
| tccaacttca cctacagccc cgacaccaag gtcctggaca tctgtgtctc gctgttgatg | 4080 |
| ggagagcagt ttctcgtcag ctggtgttag ctcgagagat ctaccggtga attcaccgcg | 4140 |
| ggtttaaact gtgccttcta gttgccagcc atctgttgtt tgcccctccc ccgtgccttc | 4200 |
| cttgaccctg gaaggtgcca ctcccactgt cctttcctaa taaaatgagg aaattgcatc | 4260 |
| gcattgtctg agtaggtgtc attctattct ggggggtggg gtggggcta gctctaga | 4318 |

<210> SEQ ID NO 23
<211> LENGTH: 4318
<212> TYPE: DNA
<213> ORGANISM: artificial
<220> FEATURE:
<223> OTHER INFORMATION: construct: sp2+hGAAco1-delta-8

<400> SEQUENCE: 23

| | |
|---|---|
| aggctcagag gcacacagga gtttctgggc tcaccctgcc cccttccaac ccctcagttc | 60 |
| ccatcctcca gcagctgttt gtgtgctgcc tctgaagtcc acactgaaca aacttcagcc | 120 |
| tactcatgtc cctaaaatgg gcaaacattg caagcagcaa acagcaaaca cacagccctc | 180 |
| cctgcctgct gaccttggag ctggggcaga ggtcagagac ctctctgggc ccatgccacc | 240 |
| tccaacatcc actcgacccc ttggaatttc ggtggagagg agcagaggtt gtcctggcgt | 300 |
| ggtttaggta gtgtgagagg ggtacccggg gatcttgcta ccagtggaac agccactaag | 360 |
| gattctgcag tgagagcaga gggccagcta agtggtactc tcccagagac tgtctgactc | 420 |
| acgccacccc ctccaccttg gacacaggac gctgtggttt ctgagccagg tacaatgact | 480 |

```
cctttcggta agtgcagtgg aagctgtaca ctgcccaggc aaagcgtccg ggcagcgtag      540
gcgggcgact cagatcccag ccagtggact tagcccctgt ttgctcctcc gataactggg      600
gtgaccttgg ttaatattca ccagcagcct ccccgttgc ccctctggat ccactgctta      660 aatacgacg aggacagggc cctgtctcct cagcttcagg caccaccact gacctgggac      720
agtgaataga tcctgagaac ttcagggtga gtctatggga cccttgatgt tttctttccc      780
cttcttttct atggttaagt tcatgtcata ggaaggggag aagtaacagg gtacacatat      840
tgaccaaatc agggtaattt tgcatttgta atttttaaaaa atgctttctt cttttaatat      900
acttttttgt ttatcttatt tctaatactt tccctaatct ctttctttca gggcaataat      960
gatacaatgt atcatgcctc tttgcaccat tctaaagaat aacagtgata atttctgggt     1020
taaggcaata gcaatatttc tgcatataaa tatttctgca tataaattgt aactgatgta     1080
agaggtttca tattgctaat agcagctaca atccagctac cattctgctt ttattttctg     1140
gttgggataa ggctggatta ttctgagtcc aagctaggcc ttttgctaa tcttgttcat     1200 acctcttatc ttcctcccac agctcctggg caacctgctg gtctctctgc tggcccatca     1260
ctttggcaaa gcacgcgtgc caccatgcct agctctgtgt cctggggcat tctgctgctg     1320
gccggcctgt gttgtctggt gcctgtgtct ctggccctac tagtgcccag agagctgagc     1380
ggcagctctc ccgtgctgga agaaacacac cctgcccatc agcagggcgc ctctagacct     1440
ggacctagag atgcccaggc ccaccccggc agacctagag ctgtgcctac ccagtgtgac     1500
gtgcccccca acagcagatt cgactgcgcc cctgacaagg ccatcaccca ggaacagtgc     1560
gaggccagag gctgctgcta catccctgcc aagcagggac tgcagggcgc tcagatggga     1620
cagccctggt gcttcttccc accctcctac cccagctaca agctggaaaa cctgagcagc     1680
agcgagatgg gctacaccgc caccctgacc agaaccaccc ccacattctt cccaaaggac     1740
atcctgaccc tgcggctgga cgtgatgatg gaaaccgaga accggctgca cttcaccatc     1800
aaggaccccg ccaatcggag atacgaggtg cccctggaaa ccccccacgt gcactctaga     1860
gcccccagcc ctctgtacag cgtggaattc agcgaggaac ccttcggcgt gatcgtgcgg     1920
agacagctga tggcagagt gctgctgaac accaccgtgg cccctctgtt cttcgccgac     1980
cagttcctgc agctgagcac cagcctgccc agccagtaca tcacaggact ggccgagcac     2040
ctgagccccc tgatgctgag cacatcctgg accggatca ccctgtggaa cagggatctg     2100
gcccctaccc ctggcgccaa tctgtacggc agccacccct tctacctggc cctggaagat     2160
ggcggatctg cccacggagt gtttctgctg aactccaacg ccatggacgt ggtgctgcag     2220
cctagccctg ccctgtcttg gagaagcaca ggcggcatcc tggatgtgta catctttctg     2280
ggccccgagc caagagcgt ggtgcagcag tatctggatg tcgtgggcta cccttcatg     2340 ccccttact ggggcctggg attccacctg tgcagatggg gctactccag caccgccatc     2400
accagacagg tggtggaaaa catgaccaga gcccacttcc cactgatgt gcagtggaac     2460 gacctggact acatggacag cagacgggac ttcaccttca caaggacgg cttcggggac     2520 ttccccgcca tggtgcagga actgcatcag ggcggcagac ggtacatgat gatcgtggat     2580
cccgccatca gctcctctgg ccctgccggc tcttacagac cctacgacga gggcctgcgg     2640
agaggcgtgt tcatcaccaa cgagacaggc cagcccctga tcggcaaagt gtggcctggc     2700
agcacagcct tccccgactt caccaatcct accgccctgg cttggtggga ggacatggtg     2760
gccgagttcc acgaccaggt gcccttcgac ggcatgtgga tcgacatgaa cgagcccagc     2820
aacttcatcc ggggcagcga ggatggctgc cccaacaacg aactggaaaa tccccccttac     2880
```

| | |
|---|---:|
| gtgcccggcg tcgtgggcgg aacactgcag gccgctacaa tctgtgccag cagccaccag | 2940 |
| tttctgagca cccactacaa cctgcacaac ctgtacggcc tgaccgaggc cattgccagc | 3000 |
| caccgcgctc tcgtgaaagc cagaggcaca cggcccttcg tgatcagcag aagcaccttt | 3060 |
| gccggccacg gcagatacgc cggacattgg actggcgacg tgtggtcctc ttgggagcag | 3120 |
| ctggcctcta gcgtgcccga gatcctgcag ttcaatctgc tgggcgtgcc actcgtgggc | 3180 |
| gccgatgtgt gtggcttcct gggcaacacc tccgaggaac tgtgtgtgcg gtggacacag | 3240 |
| ctgggcgcct tctacccttt catgagaaac acaacagcc tgctgagcct gccccaggaa | 3300 |
| ccctacagct ttagcgagcc tgcacagcag gccatgcgga aggccctgac actgagatac | 3360 |
| gctctgctgc cccacctgta caccctgttt caccaggccc atgtggccgg cgagacagtg | 3420 |
| gccagacctc tgtttctgga attccccaag acagcagca cctggaccgt ggaccatcag | 3480 |
| ctgctgtggg gagaggctct gctgattacc ccagtgctgc aggcaggcaa ggccgaagtg | 3540 |
| accggctact tccccctggg cacttggtac gacctgcaga ccgtgcctgt ggaagccctg | 3600 |
| ggatctctgc ctccacctcc tgccgctcct agagagcctg ccattcactc tgagggccag | 3660 |
| tgggtcacac tgcctgcccc cctggatacc atcaacgtgc acctgagggc cggctacatc | 3720 |
| ataccactgc agggacctgg cctgaccacc accgagtcta gacagcagcc aatggccctg | 3780 |
| gccgtggccc tgaccaaagg cggagaagct aggggcgagc tgttctggga cgatggcgag | 3840 |
| agcctggaag tgctggaaag aggcgcctat acccaagtga tcttcctggc ccggaacaac | 3900 |
| accatcgtga acgagctggt gcgcgtgacc tctgaaggcg ctggactgca gctgcagaaa | 3960 |
| gtgaccgtgc tgggagtggc cacagcccct cagcaggtgc tgtctaatgg cgtgcccgtg | 4020 |
| tccaacttca cctacagccc cgacaccaag gtgctggaca tctgcgtgtc actgctgatg | 4080 |
| ggagagcagt ttctggtgtc ctggtgctga ctcgagagat ctaccggtga attcaccgcg | 4140 |
| ggtttaaact gtgccttcta gttgccagcc atctgttgtt tgcccctccc cgtgccttc | 4200 |
| cttgaccctg gaaggtgcca ctcccactgt cctttcctaa taaaatgagg aaattgcatc | 4260 |
| gcattgtctg agtaggtgtc attctattct gggggggtggg gtggggcta gctctaga | 4318 |

<210> SEQ ID NO 24
<211> LENGTH: 4318
<212> TYPE: DNA
<213> ORGANISM: artificial
<220> FEATURE:
<223> OTHER INFORMATION: construct: sp2+hGAAco2-delta-8

<400> SEQUENCE: 24

| | |
|---|---:|
| aggctcagag gcacacagga gtttctgggc tcaccctgcc cccttccaac ccctcagttc | 60 |
| ccatcctcca gcagctgttt gtgtgctgcc tctgaagtcc acactgaaca aacttcagcc | 120 |
| tactcatgtc cctaaaatgg gcaaacattg caagcagcaa acagcaaaca cacagccctc | 180 |
| cctgcctgct gaccttggag ctggggcaga ggtcagagac ctctctgggc ccatgccacc | 240 |
| tccaacatcc actcgacccc ttggaatttc ggtggagagg agcagaggtt gtcctggcgt | 300 |
| ggtttaggta gtgtgagagg ggtacccggg gatcttgcta ccagtggaac agccactaag | 360 |
| gattctgcag tgagagcaga gggccagcta agtggtactc tcccagagac tgtctgactc | 420 |
| acgccacccc ctccaccttg gacacaggac gctgtggttt ctgagccagg tacaatgact | 480 |
| cctttcggta agtgcagtgg aagctgtaca ctgcccaggc aaagcgtccg ggcagcgtag | 540 |
| gcgggcgact cagatcccag ccagtggact tagcccctgt ttgctcctcc gataactggg | 600 |

```
gtgaccttgg ttaatattca ccagcagcct cccccgttgc ccctctggat ccactgctta    660
aatacggacg aggacagggc cctgtctcct cagcttcagg caccaccact gacctgggac    720
agtgaataga tcctgagaac ttcagggtga gtctatggga cccttgatgt tttctttccc    780 cttctttttct atggttaagt tcatgtcata ggaaggggag aagtaacagg gtacacatat    840
tgaccaaatc agggtaattt tgcatttgta attttaaaaa atgctttctt cttttaatat    900
acttttttgt ttatcttatt tctaatactt tccctaatct cttctttttca gggcaataat    960 gatacaatgt atcatgcctc tttgcaccat tctaaagaat aacagtgata atttctgggt   1020
taaggcaata gcaatatttc tgcatataaa tatttctgca tataaattgt aactgatgta   1080
agaggtttca tattgctaat agcagctaca atccagctac cattctgctt ttattttctg   1140
gttgggataa ggctggatta ttctgagtcc aagctaggcc ttttgctaa tcttgttcat   1200 acctcttatc ttcctcccac agctcctggg caacctgctg gtctctctgc tggcccatca   1260 cttttggcaaa gcacgcgtgc caccatgcca tcgtcagtgt cttggggcat tcttctgctc   1320
gccggattgt gttgcctggt gcctgtctca ttggccctgt tggtgcctag agagctgagc   1380
ggatcatccc cagtgctgga ggagactcat cctgctcacc aacagggagc ttccagacca   1440
ggaccgagag acgcccaagc ccatcctggt agaccaagag ctgtgcctac ccaatgcgac   1500
gtgccaccca actcccgatt cgactgcgcg ccagataagg ctattaccca agagcagtgt   1560
gaagccagag gttgctgcta catcccagcg aagcaaggat tgcaaggcgc ccaaatggga   1620
caaccttggt gtttcttccc cccttcgtac ccatcatata aactcgaaaa cctgtcctct   1680
tcggaaatgg gttatactgc caccctcacc agaactactc ctactttctt cccgaaagac   1740
atcttgacct tgaggctgga cgtgatgatg gagactgaaa accggctgca tttcactatc   1800
aaagatcctg ccaatcggcg atacgaggtc cctctggaaa cccctcacgt gcactcacgg   1860
gctccttctc cgctttactc cgtcgaattc tctgaggaac ccttcggagt gatcgttaga   1920
cgccagctgg atggtagagt gctgttgaac actactgtgg ccccactttt cttcgctgac   1980
cagtttctgc aactgtccac ttccctgcca tcccagtaca ttactggact cgccgaacac   2040
ctgtcgccac tgatgctctc gacctcttgg actagaatca ctttgtggaa cagagacttg   2100
gcccctactc cgggagcaaa tctgtacgga agccacccct tttacctggc gctcgaagat   2160
ggcggatccg ctcacggagt gttcctgctg aatagcaacg caatgacgt ggtgctgcaa   2220 ccttcccctg cactcagttg gagaagtacc gggggtattc tggacgtgta catcttcctc   2280
ggaccagaac ccaagagcgt ggtgcagcaa tatctggacg tggtcggata ccctttttatg   2340 cctccttact ggggactggg attccacctt tgccgttggg gctactcatc caccgccatt   2400
accagacagg tggtggagaa tatgaccaga gcccacttcc ctctcgacgt gcagtggaac   2460
gatctggact atatggactc ccggagagat ttcaccttca acaaggacgg gttccgcgat   2520
tttcccgcga tggttcaaga gctccaccag ggtggtcgaa gatatatgat gatcgtcgac   2580
ccagccattt cgagcagcgg acccgctgga tcttatagac cttacgacga aggccttagg   2640
agaggagtgt tcatcacaaa cgagactgga cagcctttga tcggtaaagt gtggcctgga   2700
tcaaccgcct ttcctgactt taccaatccc actgccttgg cttggtggga ggacatggtg   2760
gccgaattcc acgaccaagt ccccttgat ggaatgtgga tcgatatgaa cgaaccaagc   2820
aattttatca gaggttccga agacggttgc cccaacaacg aactggaaaa ccctccttat   2880
gtgcccggag tcgtgggcgg aacattacag gccgcgacta tttgcgccag cagccaccaa   2940
ttcctgtcca ctcactacaa cctccacaac ctttatggat taaccgaagc tattgcaagt   3000
```

```
cacagggctc tggtgaaggc tagagggact aggcccttg tgatctcccg atccacctt    3060
gccggacacg ggagatacgc cggtcactgg actggtgacg tgtggagctc atgggaacaa   3120
ctggcctcct ccgtgccgga aatcttacag ttcaaccttc tgggtgtccc tcttgtcgga   3180
gcagacgtgt gtgggtttct tggtaacacc tccgaggaac tgtgtgtgcg ctggactcaa   3240
ctgggtgcat tctacccatt catgagaaac cacaactcct tgctgtccct gccacaagag   3300
ccctactcgt tcagcgagcc tgcacaacag gctatgcgga aggcactgac cctgagatac   3360
gccctgcttc cacacttata cactctcttc catcaagcgc atgtggcagg agaaaccgtt   3420
gcaaggcctc ttttccttga attccccaag gattcctcga cttggacggt ggatcatcag   3480
ctgctgtggg gagaagctct gctgattact ccagtgttgc aagccggaaa agctgaggtg   3540
accggatact ttccgctggg aacctggtac gacctccaga ctgtccctgt tgaagccctt   3600
ggatcactgc ctccgcctcc ggcagctcca cgcgaaccag ctatacattc cgagggacag   3660
tgggttacat taccagctcc tctggacaca atcaacgtcc acttaagagc tggctacatt   3720
atccctctgc aaggaccagg actgactacg accgagagca gacagcagcc aatggcactg   3780
gctgtggctc tgaccaaggg aggggaagct agaggagaac tcttctggga tgatggggag   3840
tcccttgaag tgctggaaag aggcgcttac actcaagtca ttttccttgc acggaacaac   3900
accattgtga cgaattggt gcgagtgacc agcgaaggag ctggacttca actgcagaag   3960
gtcactgtgc tcggagtggc taccgctcct cagcaagtgc tgtcgaatgg agtccccgtg   4020
tcaaacttta cctactcccc tgacactaag gtgctcgaca tttgcgtgtc cctcctgatg   4080
ggagagcagt tccttgtgtc ctggtgttga ctcgagagat ctaccggtga attcaccgcg   4140
ggtttaaact gtgccttcta gttgccagcc atctgttgtt tgcccctccc ccgtgccttc   4200
cttgaccctg gaaggtgcca ctcccactgt cctttcctaa taaaatgagg aaattgcatc   4260
gcattgtctg agtaggtgtc attctattct ggggggtggg gtggggcta gctctaga     4318
```

<210> SEQ ID NO 25
<211> LENGTH: 4300
<212> TYPE: DNA
<213> ORGANISM: artificial
<220> FEATURE:
<223> OTHER INFORMATION: construct: sp7+hGAAco1-delta-8

<400> SEQUENCE: 25

```
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtacccggg gatcttgcta ccagtggaac agccactaag    360
gattctgcag tgagagcaga gggccagcta agtggtactc tcccagagac tgtctgactc    420
acgccacccc ctcccaccttg gacacaggac gctgtggttt ctgagccagg tacaatgact   480
cctttcggta agtgcagtgg aagctgtaca ctgcccaggc aaagcgtccg ggcagcgtag   540
gcgggcgact cagatcccag ccagtggact tagcccctgt ttgctcctcc gataactggg   600
gtgaccttgg ttaatattca ccagcagcct ccccgttgc ccctctggat ccactgctta    660
aatacggacg aggacagggc cctgtctcct cagcttcagg caccaccact gacctgggac   720
```

```
agtgaataga tcctgagaac ttcagggtga gtctatggga cccttgatgt tttcttccc    780
cttcttttct atggttaagt tcatgtcata ggaaggggag aagtaacagg gtacacatat   840
tgaccaaatc agggtaattt tgcatttgta attttaaaaa atgctttctt cttttaatat   900
acttttttgt ttatcttatt tctaatactt tccctaatct cttttcttca gggcaataat   960
gatacaatgt atcatgcctc tttgcaccat tctaaagaat aacagtgata atttctgggt  1020
taaggcaata gcaatatttc tgcatataaa tatttctgca tataaattgt aactgatgta  1080
agaggtttca tattgctaat agcagctaca atccagctac cattctgctt ttattttctg  1140
gttgggataa ggctggatta ttctgagtcc aagctaggcc cttttgctaa tcttgttcat  1200
acctcttatc ttcctcccac agctcctggg caacctgctg gtctctctgc tggcccatca  1260
ctttggcaaa gcacgcgtgc caccatggcc tttctgtggc tgctgagctg ttgggccctg  1320
ctgggcacca ccttcggcct actagtgccc agagagctga gcggcagctc tcccgtgctg  1380
gaagaaacac accctgccca tcagcagggc gcctctagac ctggacctag agatgcccag  1440
gcccaccccg gcagacctag agctgtgcct acccagtgtg acgtgccccc caacagcaga  1500
ttcgactgcg cccctgacaa ggccatcacc caggaacagt gcgaggccag aggctgctgc  1560
tacatccctg ccaagcaggg actgcagggc gctcagatgg acagccctg gtgcttcttc   1620
ccacctcct accccagcta caagctggaa aacctgagca gcagcgagat gggctacacc   1680
gccaccctga ccagaaccac ccccacattc ttcccaaagg acatcctgac cctgcgctg    1740
gacgtgatga tggaaaccga gaaccggctg cacttcacca tcaaggaccc cgccaatcgg   1800
agatacgagg tgcccctgga aaccccccac gtgcactcta gagcccccag ccctctgtac  1860
agcgtggaat tcagcgagga acccttcggc gtgatcgtgc ggagacagct ggatggcaga  1920
gtgctgctga acaccaccgt ggcccctctg ttcttcgccg accagttcct gcagctgagc  1980
accagcctgc ccagccagta catcacagga ctggccgagc acctgagccc cctgatgctg  2040
agcacatcct ggaccggat cacccctgtg aacagggatc tggcccctac ccctggcgcc   2100
aatctgtacg gcagccaccc tttctacctg gccctggaag atggcggatc tgcccacgga  2160
gtgtttctgc tgaactccaa cgccatggac gtggtgctgc agcctagccc tgccctgtct   2220
tggagaagca caggcggcat cctggatgtg tacatctttc tgggccccga gcccaagagc   2280
gtggtgcagc agtatctgga tgtcgtgggc taccccttca tgcccccctta ctggggcctg  2340
ggattccacc tgtgcagatg gggctactcc agcaccgcca tcaccagaca ggtggtggaa   2400
aacatgacca gagcccactt cccactggat gtgcagtgga acgacctgga ctacatggac  2460
agcagacggg acttcaccct caacaaggac ggcttccggg acttccccgc catggtgcag  2520
gaactgcatc agggcggcag acggtacatg atgatcgtgg atcccgccat cagctcctct  2580
ggccctgccg gctcttacag accctacgac gagggcctgc ggagaggcgt gttcatcacc  2640
aacgagacag gccagcccct gatcggcaaa gtgtggcctg gcagcacagc cttccccgac  2700
ttcaccaatc ctaccgccct ggcttggtgg aggacatgg tggccgagtt ccacgaccag   2760
gtgcccttcg acggcatgtg gatcgacatg aacgagccca gcaacttcat ccggggcagc  2820
gaggatggct gccccaacaa cgaactggaa aatcccccctt acgtgccggg cgtcgtgggc   2880
ggaacactgc aggccgctac aatctgtgcc agcagccacc agtttctgag cacccactac  2940
aacctgcaca acctgtacgg cctgaccgag gccattgcca gccaccgcgc tctcgtgaaa   3000
gccagaggca cacggccctt cgtgatcagc agaagcacct ttgccggcca cggcagatac  3060
gccggacatt ggactggcga cgtgtggtcc tcttgggagc agctggcctc tagcgtgccc  3120
```

-continued

```
gagatcctgc agttcaatct gctgggcgtg ccactcgtgg gcgccgatgt gtgtggcttc    3180
ctgggcaaca cctccgagga actgtgtgtg cggtggacac agctgggcgc cttctaccct    3240
ttcatgagaa accacaacag cctgctgagc ctgccccagg aaccctacag ctttagcgag    3300
cctgcacagc aggccatgcg gaaggccctg acactgagat acgctctgct gccccacctg    3360
tacaccctgt ttcaccaggc ccatgtggcc ggcgagacag tggccagacc tctgtttctg    3420
gaattcccca aggacagcag cacctggacc gtggaccatc agctgctgtg gggagaggct    3480
ctgctgatta ccccagtgct gcaggcaggc aaggccgaag tgaccggcta ctttcccctg    3540
ggcacttggt acgacctgca gaccgtgcct gtggaagccc tgggatctct gcctccacct    3600
cctgccgctc ctagagagcc tgccattcac tctgagggcc agtgggtcac actgcctgcc    3660
cccctggata ccatcaacgt gcacctgagg gccggctaca tcataccact gcagggacct    3720
ggcctgacca ccaccgagtc tagacagcag ccaatggccc tggccgtggc cctgaccaaa    3780
ggcggagaag ctaggggcga gctgttctgg gacgatggcg agagcctgga agtgctggaa    3840
agaggcgcct atacccaagt gatcttcctg gcccggaaca caccatcgt gaacgagctg    3900 gtgcgcgtga cctctgaagg cgctggactg cagctgcaga aagtgaccgt gctgggagtg    3960
gccacagccc ctcagcaggt gctgtctaat ggcgtgcccg tgtccaactt cacctacagc    4020
cccgacacca aggtgctgga catctgcgtg tcactgctga tgggagagca gtttctggtg    4080
tcctggtgct gactcgagag atctaccggt gaattcaccg cgggtttaaa ctgtgccttc    4140
tagttgccag ccatctgttg tttgcccctc cccgtgcct tccttgaccc tggaaggtgc    4200
cactcccact gtcctttcct aataaaatga ggaaattgca tcgcattgtc tgagtaggtg    4260
tcattctatt ctgggggtgg ggtgggggc tagctctaga                          4300
```

<210> SEQ ID NO 26
<211> LENGTH: 4198
<212> TYPE: DNA
<213> ORGANISM: artificial
<220> FEATURE:
<223> OTHER INFORMATION: sp7+hGAAco1-delta-42

<400> SEQUENCE: 26

```
aggctcagag gcacacagga gtttctgggc tcaccctgcc cccttccaac ccctcagttc      60
ccatcctcca gcagctgttt gtgtgctgcc tctgaagtcc acactgaaca aacttcagcc     120
tactcatgtc cctaaaatgg gcaaacattg caagcagcaa acagcaaaca cacagccctc     180
cctgcctgct gaccttggag ctggggcaga ggtcagagac ctctctgggc ccatgccacc     240
tccaacatcc actcgacccc ttggaatttc ggtggagagg agcagaggtt gtcctggcgt     300
ggtttaggta gtgtgagagg ggtacccggg gatcttgcta ccagtggaac agccactaag     360
gattctgcag tgagagcaga gggccagcta agtggtactc tcccagagac tgtctgactc     420
acgccacccc ctccacccttg gacacaggac gctgtggttt ctgagccagg tacaatgact     480
cctttcggta agtgcagtgg aagctgtaca ctgcccaggc aaagcgtccg ggcagcgtag     540
gcgggcgact cagatcccag ccagtggact tagcccctgt ttgctcctcc gataactggg     600
gtgaccttgg ttaatattca ccagcagcct ccccgttgc ccctctggat ccactgctta     660
aatacggacg aggacagggc cctgtctcct cagcttcagg caccaccact gacctgggac     720
agtgaataga tcctgagaac ttcagggtga gtctatggga cccttgatgt tttcttccc     780 cttcttttct atggttaagt tcatgtcata ggaaggggag aagtaacagg gtacacatat     840
```

```
tgaccaaatc agggtaattt tgcatttgta attttaaaaa atgctttctt cttttaatat    900
acttttttgt ttatcttatt tctaatactt tccctaatct ctttctttca gggcaataat    960
gatacaatgt atcatgcctc tttgcaccat tctaaagaat aacagtgata atttctgggt    1020
taaggcaata gcaatatttc tgcatataaa tatttctgca tataaattgt aactgatgta    1080
agaggtttca tattgctaat agcagctaca atccagctac cattctgctt ttattttctg    1140
gttgggataa ggctggatta ttctgagtcc aagctaggcc cttttgctaa tcttgttcat    1200
acctcttatc ttcctcccac agctcctggg caacctgctg gtctctctgc tggcccatca    1260
ctttggcaaa gcacgcgtgc caccatggcc tttctgtggc tgctgagctg ttgggccctg    1320
ctgggcacca ccttcggcgc ccaccccggc agacctagag ctgtgcctac ccagtgtgac    1380
gtgcccccca acagcagatt cgactgcgcc cctgacaagg ccatcaccca ggaacagtgc    1440
gaggccagag gctgctgcta catccctgcc aagcagggac tgcagggcgc tcagatggga    1500
cagccctggt gcttcttccc accctcctac cccagctaca agctggaaaa cctgagcagc    1560
agcgagatgg gctacaccgc cacctgacc agaaccaccc ccacattctt cccaaaggac    1620
atcctgaccc tgcggctgga cgtgatgatg gaaaccgaga accggctgca cttcaccatc    1680
aaggaccccg ccaatcggag atacgaggtg cccctgaaa ccccccacgt gcactctaga    1740
gcccccagcc ctctgtacag cgtggaattc agcgaggaac ccttcggcgt gatcgtgcgg    1800
agacagctga tggcagagt gctgctgaac accaccgtgg cccctctgtt cttcgccgac    1860
cagttcctgc agctgagcac cagcctgccc agccagtaca tcacaggact ggccgagcac    1920
ctgagccccc tgatgctgag cacatcctgg acccggatca ccctgtggaa cagggatctg    1980
gccccctaccc ctggcgccaa tctgtacggc agccaccctt tctacctggc cctggaagat    2040
ggcggatctg cccacggagt gttctgctg aactccaacg ccatgacgt ggtgctgcag    2100
cctagccctg ccctgtcttg gagaagcaca ggcggcatcc tggatgtgta catctttctg    2160
ggcccccgagc caagagcgt ggtgcagcag tatctggatg tcgtgggcta cccccttcatg    2220
cccccttact ggggcctggg attccacctg tgcagatggg gctactccag caccgccatc    2280
accagacagg tggtggaaaaa catgaccaga gcccacttcc cactgatgt gcagtggaac    2340
gacctggact acatggacag cagacgggac ttcaccttca caaggacgg cttccgggac    2400
ttccccgcca tggtgcagga actgcatcag ggcggcagac ggtacatgat gatcgtggat    2460
cccgccatca gctcctctgg ccctgccggc tcttacagac cctacgacga gggcctgcgg    2520
agaggcgtgt tcatcaccaa cgagacaggc cagcccctga tcggcaaagt gtggcctggc    2580
agcacagcct tccccgactt caccaatcct accgccctgg cttggtggga ggacatggtg    2640
gccgagttcc acgaccaggt gccccttcgac ggcatgtgga tcgacatgaa cgagcccagc    2700
aacttcatcc ggggcagcga ggatggctgc cccaacaacg aactggaaaa tcccccttac    2760
gtgcccggcg tcgtgggcgg aacactgcag gccgctacaa tctgtgccag cagccaccag    2820
tttctgagca cccactacaa cctgcacaac ctgtacggcc tgaccgaggc cattgccagc    2880
caccgcgctc tcgtgaaagc cagaggcaca cggcccttcg tgatcagcag aagcaccttt    2940
gccgccacg gcagatacgc cggacattgg actggcgacg tgtggtcctc ttgggagcag    3000
ctggcctcta gcgtgcccga tcctgcag ttcaatctgc tgggcgtgcc actcgtgggc    3060
gccgatgtgt gtggcttcct gggcaacacc tccgaggaac tgtgtgtgcg gtggacacag    3120
ctgggcgcct tctaccctt catgagaaac cacaacagcc tgctgagcct gccccaggaa    3180
ccctacagct ttagcgagcc tgcacagcag gccatgcgga aggccctgac actgagatac    3240
```

```
gctctgctgc cccacctgta caccctgttt caccaggccc atgtggccgg cgagacagtg   3300
gccagacctc tgtttctgga attccccaag gacagcagca cctggaccgt ggaccatcag   3360
ctgctgtggg gagaggctct gctgattacc ccagtgctgc aggcaggcaa ggccgaagtg   3420
accggctact ttcccctggg cacttggtac gacctgcaga ccgtgcctgt ggaagccctg   3480
ggatctctgc ctccacctcc tgccgctcct agagagcctg ccattcactc tgagggccag   3540
tgggtcacac tgcctgcccc cctggatacc atcaacgtgc acctgagggc cggctacatc   3600
ataccactgc agggacctgg cctgaccacc accgagtcta dacagcagcc aatggccctg   3660
gccgtggccc tgaccaaagg cggagaagct aggggcgagc tgttctggga cgatggcgag   3720
agcctggaag tgctggaaag aggcgcctat acccaagtga tcttcctggc ccggaacaac   3780
accatcgtga acgagctggt gcgcgtgacc tctgaaggcg ctggactgca gctgcagaaa   3840
gtgaccgtgc tgggagtggc cacagcccct cagcaggtgc tgtctaatgg cgtgcccgtg   3900
tccaacttca cctacagccc cgacaccaag gtgctggaca tctgcgtgtc actgctgatg   3960
ggagagcagt ttctggtgtc ctggtgctga ctcgagagat ctaccggtga attcaccgcg   4020
ggtttaaact gtgccttcta gttgccagcc atctgttgtt tgcccctccc ccgtgccttc   4080
cttgaccctg gaaggtgcca ctcccactgt cctttcctaa taaaatgagg aaattgcatc   4140
gcattgtctg agtaggtgtc attctattct ggggggtggg gtggggcta gctctaga     4198
```

<210> SEQ ID NO 27
<211> LENGTH: 917
<212> TYPE: PRT
<213> ORGANISM: artificial
<220> FEATURE:
<223> OTHER INFORMATION: hGAA-delta-8

<400> SEQUENCE: 27

```
Leu Leu Val Pro Arg Glu Leu Ser Gly Ser Pro Val Leu Glu Glu
1               5                   10                  15

Thr His Pro Ala His Gln Gln Gly Ala Ser Arg Pro Gly Pro Arg Asp
            20                  25                  30

Ala Gln Ala His Pro Gly Arg Pro Arg Ala Val Pro Thr Gln Cys Asp
        35                  40                  45

Val Pro Pro Asn Ser Arg Phe Asp Cys Ala Pro Asp Lys Ala Ile Thr
    50                  55                  60

Gln Glu Gln Cys Glu Ala Arg Gly Cys Cys Tyr Ile Pro Ala Lys Gln
65                  70                  75                  80

Gly Leu Gln Gly Ala Gln Met Gly Gln Pro Trp Cys Phe Phe Pro Pro
                85                  90                  95

Ser Tyr Pro Ser Tyr Lys Leu Glu Asn Leu Ser Ser Ser Glu Met Gly
            100                 105                 110

Tyr Thr Ala Thr Leu Thr Arg Thr Thr Pro Thr Phe Phe Pro Lys Asp
        115                 120                 125

Ile Leu Thr Leu Arg Leu Asp Val Met Met Glu Thr Glu Asn Arg Leu
    130                 135                 140

His Phe Thr Ile Lys Asp Pro Ala Asn Arg Arg Tyr Glu Val Pro Leu
145                 150                 155                 160

Glu Thr Pro His Val His Ser Arg Ala Pro Ser Pro Leu Tyr Ser Val
                165                 170                 175

Glu Phe Ser Glu Glu Pro Phe Gly Val Ile Val Arg Arg Gln Leu Asp
            180                 185                 190
```

```
Gly Arg Val Leu Leu Asn Thr Thr Val Ala Pro Leu Phe Ala Asp
            195                 200                 205

Gln Phe Leu Gln Leu Ser Thr Ser Leu Pro Ser Gln Tyr Ile Thr Gly
210                 215                 220

Leu Ala Glu His Leu Ser Pro Leu Met Leu Ser Thr Ser Trp Thr Arg
225                 230                 235                 240

Ile Thr Leu Trp Asn Arg Asp Leu Ala Pro Thr Pro Gly Ala Asn Leu
            245                 250                 255

Tyr Gly Ser His Pro Phe Tyr Leu Ala Leu Glu Asp Gly Gly Ser Ala
                260                 265                 270

His Gly Val Phe Leu Leu Asn Ser Asn Ala Met Asp Val Val Leu Gln
            275                 280                 285

Pro Ser Pro Ala Leu Ser Trp Arg Ser Thr Gly Gly Ile Leu Asp Val
290                 295                 300

Tyr Ile Phe Leu Gly Pro Glu Pro Lys Ser Val Val Gln Gln Tyr Leu
305                 310                 315                 320

Asp Val Val Gly Tyr Pro Phe Met Pro Pro Tyr Trp Gly Leu Gly Phe
                325                 330                 335

His Leu Cys Arg Trp Gly Tyr Ser Ser Thr Ala Ile Thr Arg Gln Val
            340                 345                 350

Val Glu Asn Met Thr Arg Ala His Phe Pro Leu Asp Val Gln Trp Asn
            355                 360                 365

Asp Leu Asp Tyr Met Asp Ser Arg Arg Asp Phe Thr Phe Asn Lys Asp
            370                 375                 380

Gly Phe Arg Asp Phe Pro Ala Met Val Gln Glu Leu His Gln Gly Gly
385                 390                 395                 400

Arg Arg Tyr Met Met Ile Val Asp Pro Ala Ile Ser Ser Ser Gly Pro
                405                 410                 415

Ala Gly Ser Tyr Arg Pro Tyr Asp Glu Gly Leu Arg Arg Gly Val Phe
            420                 425                 430

Ile Thr Asn Glu Thr Gly Gln Pro Leu Ile Gly Lys Val Trp Pro Gly
            435                 440                 445

Ser Thr Ala Phe Pro Asp Phe Thr Asn Pro Thr Ala Leu Ala Trp Trp
450                 455                 460

Glu Asp Met Val Ala Glu Phe His Asp Gln Val Pro Phe Asp Gly Met
465                 470                 475                 480

Trp Ile Asp Met Asn Glu Pro Ser Asn Phe Ile Arg Gly Ser Glu Asp
            485                 490                 495

Gly Cys Pro Asn Asn Glu Leu Glu Asn Pro Pro Tyr Val Pro Gly Val
                500                 505                 510

Val Gly Gly Thr Leu Gln Ala Ala Thr Ile Cys Ala Ser Ser His Gln
            515                 520                 525

Phe Leu Ser Thr His Tyr Asn Leu His Asn Leu Tyr Gly Leu Thr Glu
530                 535                 540

Ala Ile Ala Ser His Arg Ala Leu Val Lys Ala Arg Gly Thr Arg Pro
545                 550                 555                 560

Phe Val Ile Ser Arg Ser Thr Phe Ala Gly His Gly Arg Tyr Ala Gly
                565                 570                 575

His Trp Thr Gly Asp Val Trp Ser Ser Trp Glu Gln Leu Ala Ser Ser
            580                 585                 590

Val Pro Glu Ile Leu Gln Phe Asn Leu Leu Gly Val Pro Leu Val Gly
            595                 600                 605

Ala Asp Val Cys Gly Phe Leu Gly Asn Thr Ser Glu Glu Leu Cys Val
```

```
            610                 615                 620
Arg Trp Thr Gln Leu Gly Ala Phe Tyr Pro Phe Met Arg Asn His Asn
625                 630                 635                 640

Ser Leu Leu Ser Leu Pro Gln Glu Pro Tyr Ser Phe Ser Glu Pro Ala
                645                 650                 655

Gln Gln Ala Met Arg Lys Ala Leu Thr Leu Arg Tyr Ala Leu Leu Pro
                660                 665                 670

His Leu Tyr Thr Leu Phe His Gln Ala His Val Ala Gly Glu Thr Val
                675                 680                 685

Ala Arg Pro Leu Phe Leu Glu Phe Pro Lys Asp Ser Ser Thr Trp Thr
690                 695                 700

Val Asp His Gln Leu Leu Trp Gly Glu Ala Leu Leu Ile Thr Pro Val
705                 710                 715                 720

Leu Gln Ala Gly Lys Ala Glu Val Thr Gly Tyr Phe Pro Leu Gly Thr
                725                 730                 735

Trp Tyr Asp Leu Gln Thr Val Pro Val Glu Ala Leu Gly Ser Leu Pro
                740                 745                 750

Pro Pro Pro Ala Ala Pro Arg Glu Pro Ala Ile His Ser Glu Gly Gln
                755                 760                 765

Trp Val Thr Leu Pro Ala Pro Leu Asp Thr Ile Asn Val His Leu Arg
                770                 775                 780

Ala Gly Tyr Ile Ile Pro Leu Gln Gly Pro Gly Leu Thr Thr Thr Glu
785                 790                 795                 800

Ser Arg Gln Gln Pro Met Ala Leu Ala Val Ala Leu Thr Lys Gly Gly
                805                 810                 815

Glu Ala Arg Gly Glu Leu Phe Trp Asp Asp Gly Glu Ser Leu Glu Val
                820                 825                 830

Leu Glu Arg Gly Ala Tyr Thr Gln Val Ile Phe Leu Ala Arg Asn Asn
                835                 840                 845

Thr Ile Val Asn Glu Leu Val Arg Val Thr Ser Glu Gly Ala Gly Leu
                850                 855                 860

Gln Leu Gln Lys Val Thr Val Leu Gly Val Ala Thr Ala Pro Gln Gln
865                 870                 875                 880

Val Leu Ser Asn Gly Val Pro Val Ser Asn Phe Thr Tyr Ser Pro Asp
                885                 890                 895

Thr Lys Val Leu Asp Ile Cys Val Ser Leu Leu Met Gly Glu Gln Phe
                900                 905                 910

Leu Val Ser Trp Cys
                915

<210> SEQ ID NO 28
<211> LENGTH: 883
<212> TYPE: PRT
<213> ORGANISM: artificial
<220> FEATURE:
<223> OTHER INFORMATION: hGAA-delta-42

<400> SEQUENCE: 28

Ala His Pro Gly Arg Pro Arg Ala Val Pro Thr Gln Cys Asp Val Pro
1               5                   10                  15

Pro Asn Ser Arg Phe Asp Cys Ala Pro Asp Lys Ala Ile Thr Gln Glu
                20                  25                  30

Gln Cys Glu Ala Arg Gly Cys Cys Tyr Ile Pro Ala Lys Gln Gly Leu
            35                  40                  45

Gln Gly Ala Gln Met Gly Gln Pro Trp Cys Phe Phe Pro Pro Ser Tyr
```

```
            50                  55                  60
Pro Ser Tyr Lys Leu Glu Asn Leu Ser Ser Glu Met Gly Tyr Thr
65                  70                  75                  80

Ala Thr Leu Thr Arg Thr Thr Pro Thr Phe Phe Pro Lys Asp Ile Leu
                85                  90                  95

Thr Leu Arg Leu Asp Val Met Met Glu Thr Glu Asn Arg Leu His Phe
            100                 105                 110

Thr Ile Lys Asp Pro Ala Asn Arg Arg Tyr Glu Val Pro Leu Glu Thr
        115                 120                 125

Pro His Val His Ser Arg Ala Pro Ser Pro Leu Tyr Ser Val Glu Phe
    130                 135                 140

Ser Glu Glu Pro Phe Gly Val Ile Val Arg Arg Gln Leu Asp Gly Arg
145                 150                 155                 160

Val Leu Leu Asn Thr Thr Val Ala Pro Leu Phe Phe Ala Asp Gln Phe
                165                 170                 175

Leu Gln Leu Ser Thr Ser Leu Pro Ser Gln Tyr Ile Thr Gly Leu Ala
            180                 185                 190

Glu His Leu Ser Pro Leu Met Leu Ser Thr Ser Trp Thr Arg Ile Thr
        195                 200                 205

Leu Trp Asn Arg Asp Leu Ala Pro Thr Pro Gly Ala Asn Leu Tyr Gly
    210                 215                 220

Ser His Pro Phe Tyr Leu Ala Leu Glu Asp Gly Gly Ser Ala His Gly
225                 230                 235                 240

Val Phe Leu Leu Asn Ser Asn Ala Met Asp Val Val Leu Gln Pro Ser
                245                 250                 255

Pro Ala Leu Ser Trp Arg Ser Thr Gly Gly Ile Leu Asp Val Tyr Ile
            260                 265                 270

Phe Leu Gly Pro Glu Pro Lys Ser Val Val Gln Gln Tyr Leu Asp Val
        275                 280                 285

Val Gly Tyr Pro Phe Met Pro Pro Tyr Trp Gly Leu Gly Phe His Leu
    290                 295                 300

Cys Arg Trp Gly Tyr Ser Ser Thr Ala Ile Thr Arg Gln Val Val Glu
305                 310                 315                 320

Asn Met Thr Arg Ala His Phe Pro Leu Asp Val Gln Trp Asn Asp Leu
                325                 330                 335

Asp Tyr Met Asp Ser Arg Arg Asp Phe Thr Phe Asn Lys Asp Gly Phe
            340                 345                 350

Arg Asp Phe Pro Ala Met Val Gln Glu Leu His Gln Gly Gly Arg Arg
        355                 360                 365

Tyr Met Met Ile Val Asp Pro Ala Ile Ser Ser Ser Gly Pro Ala Gly
    370                 375                 380

Ser Tyr Arg Pro Tyr Asp Glu Gly Leu Arg Arg Gly Val Phe Ile Thr
385                 390                 395                 400

Asn Glu Thr Gly Gln Pro Leu Ile Gly Lys Val Trp Pro Gly Ser Thr
                405                 410                 415

Ala Phe Pro Asp Phe Thr Asn Pro Thr Ala Leu Ala Trp Trp Glu Asp
            420                 425                 430

Met Val Ala Glu Phe His Asp Gln Val Pro Phe Asp Gly Met Trp Ile
        435                 440                 445

Asp Met Asn Glu Pro Ser Asn Phe Ile Arg Gly Ser Glu Asp Gly Cys
    450                 455                 460

Pro Asn Asn Glu Leu Glu Asn Pro Pro Tyr Val Pro Gly Val Val Gly
465                 470                 475                 480
```

```
Gly Thr Leu Gln Ala Ala Thr Ile Cys Ala Ser Ser His Gln Phe Leu
                485                 490                 495

Ser Thr His Tyr Asn Leu His Asn Leu Tyr Gly Leu Thr Glu Ala Ile
                500                 505                 510

Ala Ser His Arg Ala Leu Val Lys Ala Arg Gly Thr Arg Pro Phe Val
                515                 520                 525

Ile Ser Arg Ser Thr Phe Ala Gly His Gly Arg Tyr Ala Gly His Trp
                530                 535                 540

Thr Gly Asp Val Trp Ser Ser Trp Glu Gln Leu Ala Ser Ser Val Pro
545                 550                 555                 560

Glu Ile Leu Gln Phe Asn Leu Leu Gly Val Pro Leu Val Gly Ala Asp
                565                 570                 575

Val Cys Gly Phe Leu Gly Asn Thr Ser Glu Glu Leu Cys Val Arg Trp
                580                 585                 590

Thr Gln Leu Gly Ala Phe Tyr Pro Phe Met Arg Asn His Asn Ser Leu
                595                 600                 605

Leu Ser Leu Pro Gln Glu Pro Tyr Ser Phe Ser Glu Pro Ala Gln Gln
                610                 615                 620

Ala Met Arg Lys Ala Leu Thr Leu Arg Tyr Ala Leu Leu Pro His Leu
625                 630                 635                 640

Tyr Thr Leu Phe His Gln Ala His Val Ala Gly Glu Thr Val Ala Arg
                645                 650                 655

Pro Leu Phe Leu Glu Phe Pro Lys Asp Ser Ser Thr Trp Thr Val Asp
                660                 665                 670

His Gln Leu Leu Trp Gly Glu Ala Leu Leu Ile Thr Pro Val Leu Gln
                675                 680                 685

Ala Gly Lys Ala Glu Val Thr Gly Tyr Phe Pro Leu Gly Thr Trp Tyr
690                 695                 700

Asp Leu Gln Thr Val Pro Val Glu Ala Leu Gly Ser Leu Pro Pro Pro
705                 710                 715                 720

Pro Ala Ala Pro Arg Glu Pro Ala Ile His Ser Gly Gln Trp Val
                725                 730                 735

Thr Leu Pro Ala Pro Leu Asp Thr Ile Asn Val His Leu Arg Ala Gly
                740                 745                 750

Tyr Ile Ile Pro Leu Gln Gly Pro Gly Leu Thr Thr Thr Glu Ser Arg
                755                 760                 765

Gln Gln Pro Met Ala Leu Ala Val Ala Leu Thr Lys Gly Gly Glu Ala
                770                 775                 780

Arg Gly Glu Leu Phe Trp Asp Asp Gly Glu Ser Leu Glu Val Leu Glu
785                 790                 795                 800

Arg Gly Ala Tyr Thr Gln Val Ile Phe Leu Ala Arg Asn Asn Thr Ile
                805                 810                 815

Val Asn Glu Leu Val Arg Val Thr Ser Glu Gly Ala Gly Leu Gln Leu
                820                 825                 830

Gln Lys Val Thr Val Leu Gly Val Ala Thr Ala Pro Gln Gln Val Leu
                835                 840                 845

Ser Asn Gly Val Pro Val Ser Asn Phe Thr Tyr Ser Pro Asp Thr Lys
                850                 855                 860

Val Leu Asp Ile Cys Val Ser Leu Leu Met Gly Glu Gln Phe Leu Val
865                 870                 875                 880

Ser Trp Cys
```

```
<210> SEQ ID NO 29
<211> LENGTH: 952
<212> TYPE: PRT
<213> ORGANISM: homo sapiens

<400> SEQUENCE: 29

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380
```

-continued

```
Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
            405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
            565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
            770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
```

805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
                915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 30
<211> LENGTH: 952
<212> TYPE: PRT
<213> ORGANISM: homo sapiens

<400> SEQUENCE: 30

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

-continued

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
            245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu

```
                    645                 650                 655
Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 31
<211> LENGTH: 957
<212> TYPE: PRT
<213> ORGANISM: homo sapiens

<400> SEQUENCE: 31

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60
```

-continued

```
Pro Arg Asp Ala Gln Ala His Pro Gly Arg Pro Arg Ala Val Pro Thr
 65                  70                  75                  80

Gln Cys Asp Val Pro Pro Asn Ser Arg Phe Asp Cys Ala Pro Asp Lys
             85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
```

```
                    485                 490                 495
Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
                515                 520                 525

Ser Glu Asp Gly Cys Pro Asn Asn Leu Glu Asn Pro Pro Tyr Val
            530                 535                 540

Pro Gly Val Val Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
            770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
            835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910
```

```
Pro Gln Gln Val Leu Ser Asn Gly Val Pro Val Ser Asn Phe Thr Tyr
            915                 920                 925

Ser Pro Asp Thr Lys Ala Arg Gly Pro Arg Val Leu Asp Ile Cys Val
    930                 935                 940

Ser Leu Leu Met Gly Glu Gln Phe Leu Val Ser Trp Cys
945                 950                 955

<210> SEQ ID NO 32
<211> LENGTH: 952
<212> TYPE: PRT
<213> ORGANISM: homo sapiens

<400> SEQUENCE: 32

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly
        50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
```

-continued

```
                325                 330                 335
Leu Asp Val Tyr Ile Phe Leu Gly Pro Glu Pro Lys Ser Val Val Gln
                340                 345                 350
Gln Tyr Leu Asp Val Val Gly Tyr Pro Phe Met Pro Pro Tyr Trp Gly
                355                 360                 365
Leu Gly Phe His Leu Cys Arg Trp Gly Tyr Ser Ser Thr Ala Ile Thr
                370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
                420                 425                 430
Gln Gly Gly Arg Arg Tyr Met Met Ile Val Asp Pro Ala Ile Ser Ser
                435                 440                 445
Ser Gly Pro Ala Gly Ser Tyr Arg Leu Tyr Asp Glu Gly Leu Arg Arg
                450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
                500                 505                 510
Asp Gly Met Trp Ile Asp Met Asn Glu Pro Ser Asn Phe Ile Arg Gly
                515                 520                 525
Ser Glu Asp Gly Cys Pro Asn Asn Glu Leu Glu Asn Pro Pro Tyr Val
                530                 535                 540
Pro Gly Val Val Gly Gly Thr Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
                580                 585                 590
Thr Arg Pro Phe Val Ile Ser Arg Ser Thr Phe Ala Gly His Gly Arg
                595                 600                 605
Tyr Ala Gly His Trp Thr Gly Asp Val Trp Ser Ser Trp Glu Gln Leu
                610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
Leu Cys Val Arg Trp Thr Gln Leu Gly Ala Phe Tyr Pro Phe Met Arg
                660                 665                 670
Asn His Asn Ser Leu Leu Ser Leu Pro Gln Glu Pro Tyr Ser Phe Ser
                675                 680                 685
Glu Pro Ala Gln Gln Ala Met Arg Lys Ala Leu Thr Leu Arg Tyr Ala
                690                 695                 700
Leu Leu Pro His Leu Tyr Thr Leu Phe His Gln Ala His Val Ala Gly
705                 710                 715                 720
Glu Thr Val Ala Arg Pro Leu Phe Leu Glu Phe Pro Lys Asp Ser Ser
                725                 730                 735
Thr Trp Thr Val Asp His Gln Leu Leu Trp Gly Glu Ala Leu Leu Ile
                740                 745                 750
```

-continued

```
Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
770                 775                 780

Ser Leu Pro Pro Pro Ala Pro Arg Glu Pro Ala Ile His Ser
785                 790                 795                 800

Glu Gly Gln Trp Val Thr Leu Pro Ala Pro Leu Asp Thr Ile Asn Val
                    805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
            835                 840                 845

Lys Gly Gly Glu Ala Arg Gly Glu Leu Phe Trp Asp Asp Gly Glu Ser
        850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                    885                 890                 895

Ala Gly Leu Gln Leu Gln Lys Val Thr Val Leu Gly Val Ala Thr Ala
                900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
        930                 935                 940

Glu Gln Phe Leu Val Ser Trp Cys
945                 950

<210> SEQ ID NO 33
<211> LENGTH: 925
<212> TYPE: PRT
<213> ORGANISM: artificial
<220> FEATURE:
<223> OTHER INFORMATION: variant hGAAwt w/o sp

<400> SEQUENCE: 33

Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
                20                  25                  30

Ala Ser Arg Pro Gly Pro Arg Asp Ala Gln Ala His Pro Gly Arg Pro
            35                  40                  45

Arg Ala Val Pro Thr Gln Cys Asp Val Pro Pro Asn Ser Arg Phe Asp
        50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                    85                  90                  95

Gln Pro Trp Cys Phe Phe Pro Pro Ser Tyr Pro Ser Tyr Lys Leu Glu
                100                 105                 110

Asn Leu Ser Ser Ser Glu Met Gly Tyr Thr Ala Thr Leu Thr Arg Thr
            115                 120                 125

Thr Pro Thr Phe Phe Pro Lys Asp Ile Leu Thr Leu Arg Leu Asp Val
        130                 135                 140

Met Met Glu Thr Glu Asn Arg Leu His Phe Thr Ile Lys Asp Pro Ala
145                 150                 155                 160
```

```
Asn Arg Arg Tyr Glu Val Pro Leu Glu Thr Pro Arg Val His Ser Arg
                165                 170                 175

Ala Pro Ser Pro Leu Tyr Ser Val Glu Phe Ser Glu Glu Pro Phe Gly
            180                 185                 190

Val Ile Val His Arg Gln Leu Asp Gly Arg Val Leu Leu Asn Thr Thr
        195                 200                 205

Val Ala Pro Leu Phe Phe Ala Asp Gln Phe Leu Gln Leu Ser Thr Ser
    210                 215                 220

Leu Pro Ser Gln Tyr Ile Thr Gly Leu Ala Glu His Leu Ser Pro Leu
225                 230                 235                 240

Met Leu Ser Thr Ser Trp Thr Arg Ile Thr Leu Trp Asn Arg Asp Leu
                245                 250                 255

Ala Pro Thr Pro Gly Ala Asn Leu Tyr Gly Ser His Pro Phe Tyr Leu
            260                 265                 270

Ala Leu Glu Asp Gly Gly Ser Ala His Gly Val Phe Leu Leu Asn Ser
        275                 280                 285

Asn Ala Met Asp Val Val Leu Gln Pro Ser Pro Ala Leu Ser Trp Arg
    290                 295                 300

Ser Thr Gly Gly Ile Leu Asp Val Tyr Ile Phe Leu Gly Pro Glu Pro
305                 310                 315                 320

Lys Ser Val Val Gln Gln Tyr Leu Asp Val Val Gly Tyr Pro Phe Met
                325                 330                 335

Pro Pro Tyr Trp Gly Leu Gly Phe His Leu Cys Arg Trp Gly Tyr Ser
            340                 345                 350

Ser Thr Ala Ile Thr Arg Gln Val Val Glu Asn Met Thr Arg Ala His
        355                 360                 365

Phe Pro Leu Asp Val Gln Trp Asn Asp Leu Asp Tyr Met Asp Ser Arg
    370                 375                 380

Arg Asp Phe Thr Phe Asn Lys Asp Gly Phe Arg Asp Phe Pro Ala Met
385                 390                 395                 400

Val Gln Glu Leu His Gln Gly Gly Arg Arg Tyr Met Met Ile Val Asp
                405                 410                 415

Pro Ala Ile Ser Ser Ser Gly Pro Ala Gly Ser Tyr Arg Pro Tyr Asp
            420                 425                 430

Glu Gly Leu Arg Arg Gly Val Phe Ile Thr Asn Glu Thr Gly Gln Pro
        435                 440                 445

Leu Ile Gly Lys Val Trp Pro Gly Ser Thr Ala Phe Pro Asp Phe Thr
    450                 455                 460

Asn Pro Thr Ala Leu Ala Trp Trp Glu Asp Met Val Ala Glu Phe His
465                 470                 475                 480

Asp Gln Val Pro Phe Asp Gly Met Trp Ile Asp Met Asn Glu Pro Ser
                485                 490                 495

Asn Phe Ile Arg Gly Ser Glu Asp Gly Cys Pro Asn Asn Glu Leu Glu
            500                 505                 510

Asn Pro Pro Tyr Val Pro Gly Val Gly Gly Thr Leu Gln Ala Ala
        515                 520                 525

Thr Ile Cys Ala Ser Ser His Gln Phe Leu Ser Thr His Tyr Asn Leu
    530                 535                 540

His Asn Leu Tyr Gly Leu Thr Glu Ala Ile Ala Ser His Arg Ala Leu
545                 550                 555                 560

Val Lys Ala Arg Gly Thr Arg Pro Phe Val Ile Ser Arg Ser Thr Phe
                565                 570                 575
```

```
Ala Gly His Gly Arg Tyr Ala Gly His Trp Thr Gly Asp Val Trp Ser
            580                 585                 590

Ser Trp Glu Gln Leu Ala Ser Ser Val Pro Glu Ile Leu Gln Phe Asn
        595                 600                 605

Leu Leu Gly Val Pro Leu Val Gly Ala Asp Val Cys Gly Phe Leu Gly
        610                 615                 620

Asn Thr Ser Glu Glu Leu Cys Val Arg Trp Thr Gln Leu Gly Ala Phe
625                 630                 635                 640

Tyr Pro Phe Met Arg Asn His Asn Ser Leu Ser Leu Pro Gln Glu
            645                 650                 655

Pro Tyr Ser Phe Ser Glu Pro Ala Gln Gln Ala Met Arg Lys Ala Leu
        660                 665                 670

Thr Leu Arg Tyr Ala Leu Leu Pro His Leu Tyr Thr Leu Phe His Gln
        675                 680                 685

Ala His Val Ala Gly Glu Thr Val Ala Arg Pro Leu Phe Leu Glu Phe
        690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
            725                 730                 735

Thr Gly Tyr Phe Pro Leu Gly Thr Trp Tyr Asp Leu Gln Thr Val Pro
            740                 745                 750

Ile Glu Ala Leu Gly Ser Leu Pro Pro Pro Ala Ala Pro Arg Glu
            755                 760                 765

Pro Ala Ile His Ser Gly Gln Trp Val Thr Leu Pro Ala Pro Leu
770                 775                 780

Asp Thr Ile Asn Val His Leu Arg Ala Gly Tyr Ile Ile Pro Leu Gln
785                 790                 795                 800

Gly Pro Gly Leu Thr Thr Thr Glu Ser Arg Gln Gln Pro Met Ala Leu
            805                 810                 815

Ala Val Ala Leu Thr Lys Gly Gly Glu Ala Arg Gly Glu Leu Phe Trp
            820                 825                 830

Asp Asp Gly Glu Ser Leu Glu Val Leu Glu Arg Gly Ala Tyr Thr Gln
        835                 840                 845

Val Ile Phe Leu Ala Arg Asn Asn Thr Ile Val Asn Glu Leu Val Arg
850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
            885                 890                 895

Ser Asn Phe Thr Tyr Ser Pro Asp Thr Lys Val Leu Asp Ile Cys Val
            900                 905                 910

Ser Leu Leu Met Gly Glu Gln Phe Leu Val Ser Trp Cys
        915                 920                 925

<210> SEQ ID NO 34
<211> LENGTH: 896
<212> TYPE: PRT
<213> ORGANISM: artificial
<220> FEATURE:
<223> OTHER INFORMATION: hGAA-delta-29

<400> SEQUENCE: 34

Gln Gln Gly Ala Ser Arg Pro Gly Pro Arg Asp Ala Gln Ala His Pro
1               5                   10                  15
```

-continued

```
Gly Arg Pro Arg Ala Val Pro Thr Gln Cys Asp Val Pro Asn Ser
             20                  25                  30
Arg Phe Asp Cys Ala Pro Asp Lys Ala Ile Thr Gln Glu Gln Cys Glu
         35                  40                  45
Ala Arg Gly Cys Cys Tyr Ile Pro Ala Lys Gln Gly Leu Gln Gly Ala
     50                  55                  60
Gln Met Gly Gln Pro Trp Cys Phe Phe Pro Ser Tyr Pro Ser Tyr
 65                  70                  75                  80
Lys Leu Glu Asn Leu Ser Ser Ser Glu Met Gly Tyr Thr Ala Thr Leu
                 85                  90                  95
Thr Arg Thr Thr Pro Thr Phe Phe Pro Lys Asp Ile Leu Thr Leu Arg
             100                 105                 110
Leu Asp Val Met Met Glu Thr Glu Asn Arg Leu His Phe Thr Ile Lys
         115                 120                 125
Asp Pro Ala Asn Arg Arg Tyr Glu Val Pro Leu Glu Thr Pro His Val
     130                 135                 140
His Ser Arg Ala Pro Ser Pro Leu Tyr Ser Val Glu Phe Ser Glu Glu
145                 150                 155                 160
Pro Phe Gly Val Ile Val Arg Arg Gln Leu Asp Gly Arg Val Leu Leu
                 165                 170                 175
Asn Thr Thr Val Ala Pro Leu Phe Phe Ala Asp Gln Phe Leu Gln Leu
             180                 185                 190
Ser Thr Ser Leu Pro Ser Gln Tyr Ile Thr Gly Leu Ala Glu His Leu
         195                 200                 205
Ser Pro Leu Met Leu Ser Thr Ser Trp Thr Arg Ile Thr Leu Trp Asn
     210                 215                 220
Arg Asp Leu Ala Pro Thr Pro Gly Ala Asn Leu Tyr Gly Ser His Pro
225                 230                 235                 240
Phe Tyr Leu Ala Leu Glu Asp Gly Gly Ser Ala His Gly Val Phe Leu
                 245                 250                 255
Leu Asn Ser Asn Ala Met Asp Val Val Leu Gln Pro Ser Pro Ala Leu
             260                 265                 270
Ser Trp Arg Ser Thr Gly Gly Ile Leu Asp Val Tyr Ile Phe Leu Gly
         275                 280                 285
Pro Glu Pro Lys Ser Val Val Gln Gln Tyr Leu Asp Val Val Gly Tyr
     290                 295                 300
Pro Phe Met Pro Pro Tyr Trp Gly Leu Gly Phe His Leu Cys Arg Trp
305                 310                 315                 320
Gly Tyr Ser Ser Thr Ala Ile Thr Arg Gln Val Val Glu Asn Met Thr
                 325                 330                 335
Arg Ala His Phe Pro Leu Asp Val Gln Trp Asn Asp Leu Asp Tyr Met
             340                 345                 350
Asp Ser Arg Arg Asp Phe Thr Phe Asn Lys Asp Gly Phe Arg Asp Phe
         355                 360                 365
Pro Ala Met Val Gln Glu Leu His Gln Gly Gly Arg Arg Tyr Met Met
     370                 375                 380
Ile Val Asp Pro Ala Ile Ser Ser Ser Gly Pro Ala Gly Ser Tyr Arg
385                 390                 395                 400
Pro Tyr Asp Glu Gly Leu Arg Arg Gly Val Phe Ile Thr Asn Glu Thr
                 405                 410                 415
Gly Gln Pro Leu Ile Gly Lys Val Trp Pro Gly Ser Thr Ala Phe Pro
             420                 425                 430
Asp Phe Thr Asn Pro Thr Ala Leu Ala Trp Trp Glu Asp Met Val Ala
```

-continued

```
            435                 440                 445
Glu Phe His Asp Gln Val Pro Phe Asp Gly Met Trp Ile Asp Met Asn
450                 455                 460
Glu Pro Ser Asn Phe Ile Arg Gly Ser Glu Asp Gly Cys Pro Asn Asn
465                 470                 475                 480
Glu Leu Glu Asn Pro Pro Tyr Val Pro Gly Val Val Gly Gly Thr Leu
                    485                 490                 495
Gln Ala Ala Thr Ile Cys Ala Ser Ser His Gln Phe Leu Ser Thr His
                500                 505                 510
Tyr Asn Leu His Asn Leu Tyr Gly Leu Thr Glu Ala Ile Ala Ser His
            515                 520                 525
Arg Ala Leu Val Lys Ala Arg Gly Thr Arg Pro Phe Val Ile Ser Arg
530                 535                 540
Ser Thr Phe Ala Gly His Gly Arg Tyr Ala Gly His Trp Thr Gly Asp
545                 550                 555                 560
Val Trp Ser Ser Trp Glu Gln Leu Ala Ser Ser Val Pro Glu Ile Leu
                    565                 570                 575
Gln Phe Asn Leu Leu Gly Val Pro Leu Val Gly Ala Asp Val Cys Gly
                580                 585                 590
Phe Leu Gly Asn Thr Ser Glu Glu Leu Cys Val Arg Trp Thr Gln Leu
            595                 600                 605
Gly Ala Phe Tyr Pro Phe Met Arg Asn His Asn Ser Leu Leu Ser Leu
610                 615                 620
Pro Gln Glu Pro Tyr Ser Phe Ser Glu Pro Ala Gln Gln Ala Met Arg
625                 630                 635                 640
Lys Ala Leu Thr Leu Arg Tyr Ala Leu Leu Pro His Leu Tyr Thr Leu
                    645                 650                 655
Phe His Gln Ala His Val Ala Gly Glu Thr Val Ala Arg Pro Leu Phe
                660                 665                 670
Leu Glu Phe Pro Lys Asp Ser Ser Thr Trp Thr Val Asp His Gln Leu
            675                 680                 685
Leu Trp Gly Glu Ala Leu Leu Ile Thr Pro Val Leu Gln Ala Gly Lys
690                 695                 700
Ala Glu Val Thr Gly Tyr Phe Pro Leu Gly Thr Trp Tyr Asp Leu Gln
705                 710                 715                 720
Thr Val Pro Val Glu Ala Leu Gly Ser Leu Pro Pro Pro Ala Ala
                    725                 730                 735
Pro Arg Glu Pro Ala Ile His Ser Glu Gly Gln Trp Val Thr Leu Pro
                740                 745                 750
Ala Pro Leu Asp Thr Ile Asn Val His Leu Arg Ala Gly Tyr Ile Ile
            755                 760                 765
Pro Leu Gln Gly Pro Gly Leu Thr Thr Thr Glu Ser Arg Gln Gln Pro
770                 775                 780
Met Ala Leu Ala Val Ala Leu Thr Lys Gly Gly Glu Ala Arg Gly Glu
785                 790                 795                 800
Leu Phe Trp Asp Asp Gly Glu Ser Leu Glu Val Leu Glu Arg Gly Ala
                    805                 810                 815
Tyr Thr Gln Val Ile Phe Leu Ala Arg Asn Asn Thr Ile Val Asn Glu
                820                 825                 830
Leu Val Arg Val Thr Ser Glu Gly Ala Gly Leu Gln Leu Gln Lys Val
            835                 840                 845
Thr Val Leu Gly Val Ala Thr Ala Pro Gln Gln Val Leu Ser Asn Gly
850                 855                 860
```

```
Val Pro Val Ser Asn Phe Thr Tyr Ser Pro Asp Thr Lys Val Leu Asp
865                 870                 875                 880

Ile Cys Val Ser Leu Leu Met Gly Glu Gln Phe Leu Val Ser Trp Cys
            885                 890                 895

<210> SEQ ID NO 35
<211> LENGTH: 882
<212> TYPE: PRT
<213> ORGANISM: artificial
<220> FEATURE:
<223> OTHER INFORMATION: hGAA-delta-43

<400> SEQUENCE: 35

His Pro Gly Arg Pro Arg Ala Val Pro Thr Gln Cys Asp Val Pro Pro
1               5                   10                  15

Asn Ser Arg Phe Asp Cys Ala Pro Asp Lys Ala Ile Thr Gln Glu Gln
            20                  25                  30

Cys Glu Ala Arg Gly Cys Cys Tyr Ile Pro Ala Lys Gln Gly Leu Gln
        35                  40                  45

Gly Ala Gln Met Gly Gln Pro Trp Cys Phe Phe Pro Pro Ser Tyr Pro
    50                  55                  60

Ser Tyr Lys Leu Glu Asn Leu Ser Ser Ser Glu Met Gly Tyr Thr Ala
65                  70                  75                  80

Thr Leu Thr Arg Thr Thr Pro Thr Phe Phe Pro Lys Asp Ile Leu Thr
                85                  90                  95

Leu Arg Leu Asp Val Met Met Glu Thr Glu Asn Arg Leu His Phe Thr
            100                 105                 110

Ile Lys Asp Pro Ala Asn Arg Arg Tyr Glu Val Pro Leu Glu Thr Pro
        115                 120                 125

His Val His Ser Arg Ala Pro Ser Pro Leu Tyr Ser Val Glu Phe Ser
    130                 135                 140

Glu Glu Pro Phe Gly Val Ile Val Arg Arg Gln Leu Asp Gly Arg Val
145                 150                 155                 160

Leu Leu Asn Thr Thr Val Ala Pro Leu Phe Phe Ala Asp Gln Phe Leu
                165                 170                 175

Gln Leu Ser Thr Ser Leu Pro Ser Gln Tyr Ile Thr Gly Leu Ala Glu
            180                 185                 190

His Leu Ser Pro Leu Met Leu Ser Thr Ser Trp Thr Arg Ile Thr Leu
        195                 200                 205

Trp Asn Arg Asp Leu Ala Pro Thr Pro Gly Ala Asn Leu Tyr Gly Ser
    210                 215                 220

His Pro Phe Tyr Leu Ala Leu Glu Asp Gly Gly Ser Ala His Gly Val
225                 230                 235                 240

Phe Leu Leu Asn Ser Asn Ala Met Asp Val Val Leu Gln Pro Ser Pro
                245                 250                 255

Ala Leu Ser Trp Arg Ser Thr Gly Gly Ile Leu Asp Val Tyr Ile Phe
            260                 265                 270

Leu Gly Pro Glu Pro Lys Ser Val Val Gln Gln Tyr Leu Asp Val Val
        275                 280                 285

Gly Tyr Pro Phe Met Pro Pro Tyr Trp Gly Leu Gly Phe His Leu Cys
    290                 295                 300

Arg Trp Gly Tyr Ser Ser Thr Ala Ile Thr Arg Gln Val Val Glu Asn
305                 310                 315                 320

Met Thr Arg Ala His Phe Pro Leu Asp Val Gln Trp Asn Asp Leu Asp
                325                 330                 335
```

```
Tyr Met Asp Ser Arg Arg Asp Phe Thr Phe Asn Lys Asp Gly Phe Arg
            340                 345                 350

Asp Phe Pro Ala Met Val Gln Glu Leu His Gln Gly Gly Arg Arg Tyr
            355                 360                 365

Met Met Ile Val Asp Pro Ala Ile Ser Ser Gly Pro Ala Gly Ser
370                 375                 380

Tyr Arg Pro Tyr Asp Glu Gly Leu Arg Arg Gly Val Phe Ile Thr Asn
385                 390                 395                 400

Glu Thr Gly Gln Pro Leu Ile Gly Lys Val Trp Pro Gly Ser Thr Ala
                405                 410                 415

Phe Pro Asp Phe Thr Asn Pro Thr Ala Leu Ala Trp Trp Glu Asp Met
            420                 425                 430

Val Ala Glu Phe His Asp Gln Val Pro Phe Asp Gly Met Trp Ile Asp
            435                 440                 445

Met Asn Glu Pro Ser Asn Phe Ile Arg Gly Ser Glu Asp Gly Cys Pro
450                 455                 460

Asn Asn Glu Leu Glu Asn Pro Pro Tyr Val Pro Gly Val Val Gly Gly
465                 470                 475                 480

Thr Leu Gln Ala Ala Thr Ile Cys Ala Ser Ser His Gln Phe Leu Ser
                485                 490                 495

Thr His Tyr Asn Leu His Asn Leu Tyr Gly Leu Thr Glu Ala Ile Ala
            500                 505                 510

Ser His Arg Ala Leu Val Lys Ala Arg Gly Thr Arg Pro Phe Val Ile
            515                 520                 525

Ser Arg Ser Thr Phe Ala Gly His Gly Arg Tyr Ala Gly His Trp Thr
            530                 535                 540

Gly Asp Val Trp Ser Ser Trp Glu Gln Leu Ala Ser Ser Val Pro Glu
545                 550                 555                 560

Ile Leu Gln Phe Asn Leu Leu Gly Val Pro Leu Val Gly Ala Asp Val
                565                 570                 575

Cys Gly Phe Leu Gly Asn Thr Ser Glu Glu Leu Cys Val Arg Trp Thr
            580                 585                 590

Gln Leu Gly Ala Phe Tyr Pro Phe Met Arg Asn His Asn Ser Leu Leu
            595                 600                 605

Ser Leu Pro Gln Glu Pro Tyr Ser Phe Ser Glu Pro Ala Gln Gln Ala
            610                 615                 620

Met Arg Lys Ala Leu Thr Leu Arg Tyr Ala Leu Leu Pro His Leu Tyr
625                 630                 635                 640

Thr Leu Phe His Gln Ala His Val Ala Gly Glu Thr Val Ala Arg Pro
                645                 650                 655

Leu Phe Leu Glu Phe Pro Lys Asp Ser Ser Thr Trp Thr Val Asp His
            660                 665                 670

Gln Leu Leu Trp Gly Glu Ala Leu Leu Ile Thr Pro Val Leu Gln Ala
            675                 680                 685

Gly Lys Ala Glu Val Thr Gly Tyr Phe Pro Leu Gly Thr Trp Tyr Asp
            690                 695                 700

Leu Gln Thr Val Pro Val Glu Ala Leu Gly Ser Leu Pro Pro Pro
705                 710                 715                 720

Ala Ala Pro Arg Glu Pro Ala Ile His Ser Glu Gly Gln Trp Val Thr
            725                 730                 735

Leu Pro Ala Pro Leu Asp Thr Ile Asn Val His Leu Arg Ala Gly Tyr
            740                 745                 750
```

```
Ile Ile Pro Leu Gln Gly Pro Gly Leu Thr Thr Thr Glu Ser Arg Gln
            755                 760                 765

Gln Pro Met Ala Leu Ala Val Ala Leu Thr Lys Gly Gly Glu Ala Arg
    770                 775                 780

Gly Glu Leu Phe Trp Asp Asp Gly Glu Ser Leu Glu Val Leu Glu Arg
785                 790                 795                 800

Gly Ala Tyr Thr Gln Val Ile Phe Leu Ala Arg Asn Asn Thr Ile Val
                805                 810                 815

Asn Glu Leu Val Arg Val Thr Ser Glu Gly Ala Gly Leu Gln Leu Gln
            820                 825                 830

Lys Val Thr Val Leu Gly Val Ala Thr Ala Pro Gln Gln Val Leu Ser
            835                 840                 845

Asn Gly Val Pro Val Ser Asn Phe Thr Tyr Ser Pro Asp Thr Lys Val
            850                 855                 860

Leu Asp Ile Cys Val Ser Leu Leu Met Gly Glu Gln Phe Leu Val Ser
865                 870                 875                 880

Trp Cys

<210> SEQ ID NO 36
<211> LENGTH: 878
<212> TYPE: PRT
<213> ORGANISM: artificial
<220> FEATURE:
<223> OTHER INFORMATION: hGAA-delta-47

<400> SEQUENCE: 36

Pro Arg Ala Val Pro Thr Gln Cys Asp Val Pro Pro Asn Ser Arg Phe
1               5                   10                  15

Asp Cys Ala Pro Asp Lys Ala Ile Thr Gln Glu Gln Cys Glu Ala Arg
            20                  25                  30

Gly Cys Cys Tyr Ile Pro Ala Lys Gln Gly Leu Gln Gly Ala Gln Met
        35                  40                  45

Gly Gln Pro Trp Cys Phe Phe Pro Pro Ser Tyr Pro Ser Tyr Lys Leu
    50                  55                  60

Glu Asn Leu Ser Ser Ser Glu Met Gly Tyr Thr Ala Thr Leu Thr Arg
65                  70                  75                  80

Thr Thr Pro Thr Phe Phe Pro Lys Asp Ile Leu Thr Leu Arg Leu Asp
                85                  90                  95

Val Met Met Glu Thr Glu Asn Arg Leu His Phe Thr Ile Lys Asp Pro
            100                 105                 110

Ala Asn Arg Arg Tyr Glu Val Pro Leu Glu Thr Pro His Val His Ser
            115                 120                 125

Arg Ala Pro Ser Pro Leu Tyr Ser Val Glu Phe Ser Glu Glu Pro Phe
    130                 135                 140

Gly Val Ile Val Arg Arg Gln Leu Asp Gly Arg Val Leu Leu Asn Thr
145                 150                 155                 160

Thr Val Ala Pro Leu Phe Phe Ala Asp Gln Phe Leu Gln Leu Ser Thr
                165                 170                 175

Ser Leu Pro Ser Gln Tyr Ile Thr Gly Leu Ala Glu His Leu Ser Pro
            180                 185                 190

Leu Met Leu Ser Thr Ser Trp Thr Arg Ile Thr Leu Trp Asn Arg Asp
            195                 200                 205

Leu Ala Pro Thr Pro Gly Ala Asn Leu Tyr Gly Ser His Pro Phe Tyr
    210                 215                 220

Leu Ala Leu Glu Asp Gly Gly Ser Ala His Gly Val Phe Leu Leu Asn
```

-continued

```
            225                 230                 235                 240
        Ser Asn Ala Met Asp Val Val Leu Gln Pro Ser Pro Ala Leu Ser Trp
                        245                 250                 255
        Arg Ser Thr Gly Gly Ile Leu Asp Val Tyr Ile Phe Leu Gly Pro Glu
                        260                 265                 270
        Pro Lys Ser Val Val Gln Gln Tyr Leu Asp Val Val Gly Tyr Pro Phe
                        275                 280                 285
        Met Pro Pro Tyr Trp Gly Leu Gly Phe His Leu Cys Arg Trp Gly Tyr
                        290                 295                 300
        Ser Ser Thr Ala Ile Thr Arg Gln Val Val Glu Asn Met Thr Arg Ala
        305                 310                 315                 320
        His Phe Pro Leu Asp Val Gln Trp Asn Asp Leu Asp Tyr Met Asp Ser
                        325                 330                 335
        Arg Arg Asp Phe Thr Phe Asn Lys Asp Gly Phe Arg Asp Phe Pro Ala
                        340                 345                 350
        Met Val Gln Glu Leu His Gln Gly Gly Arg Arg Tyr Met Met Ile Val
                        355                 360                 365
        Asp Pro Ala Ile Ser Ser Gly Pro Ala Gly Ser Tyr Arg Pro Tyr
                        370                 375                 380
        Asp Glu Gly Leu Arg Arg Gly Val Phe Ile Thr Asn Glu Thr Gly Gln
        385                 390                 395                 400
        Pro Leu Ile Gly Lys Val Trp Pro Gly Ser Thr Ala Phe Pro Asp Phe
                        405                 410                 415
        Thr Asn Pro Thr Ala Leu Ala Trp Trp Glu Asp Met Val Ala Glu Phe
                        420                 425                 430
        His Asp Gln Val Pro Phe Asp Gly Met Trp Ile Asp Met Asn Glu Pro
                        435                 440                 445
        Ser Asn Phe Ile Arg Gly Ser Glu Asp Gly Cys Pro Asn Asn Glu Leu
                        450                 455                 460
        Glu Asn Pro Pro Tyr Val Pro Gly Val Val Gly Gly Thr Leu Gln Ala
        465                 470                 475                 480
        Ala Thr Ile Cys Ala Ser Ser His Gln Phe Leu Ser Thr His Tyr Asn
                        485                 490                 495
        Leu His Asn Leu Tyr Gly Leu Thr Glu Ala Ile Ala Ser His Arg Ala
                        500                 505                 510
        Leu Val Lys Ala Arg Gly Thr Arg Pro Phe Val Ile Ser Arg Ser Thr
                        515                 520                 525
        Phe Ala Gly His Gly Arg Tyr Ala Gly His Trp Thr Gly Asp Val Trp
                        530                 535                 540
        Ser Ser Trp Glu Gln Leu Ala Ser Ser Val Pro Glu Ile Leu Gln Phe
        545                 550                 555                 560
        Asn Leu Leu Gly Val Pro Leu Val Gly Ala Asp Val Cys Gly Phe Leu
                        565                 570                 575
        Gly Asn Thr Ser Glu Glu Leu Cys Val Arg Trp Thr Gln Leu Gly Ala
                        580                 585                 590
        Phe Tyr Pro Phe Met Arg Asn His Asn Ser Leu Leu Ser Leu Pro Gln
                        595                 600                 605
        Glu Pro Tyr Ser Phe Ser Glu Pro Ala Gln Ala Met Arg Lys Ala
                        610                 615                 620
        Leu Thr Leu Arg Tyr Ala Leu Leu Pro His Leu Tyr Thr Leu Phe His
        625                 630                 635                 640
        Gln Ala His Val Ala Gly Glu Thr Val Ala Arg Pro Leu Phe Leu Glu
                        645                 650                 655
```

Phe Pro Lys Asp Ser Ser Thr Trp Thr Val Asp His Gln Leu Leu Trp
            660                 665                 670

Gly Glu Ala Leu Leu Ile Thr Pro Val Leu Gln Ala Gly Lys Ala Glu
        675                 680                 685

Val Thr Gly Tyr Phe Pro Leu Gly Thr Trp Tyr Asp Leu Gln Thr Val
690                 695                 700

Pro Val Glu Ala Leu Gly Ser Leu Pro Pro Pro Ala Ala Pro Arg
705                 710                 715                 720

Glu Pro Ala Ile His Ser Glu Gly Gln Trp Val Thr Leu Pro Ala Pro
                725                 730                 735

Leu Asp Thr Ile Asn Val His Leu Arg Ala Gly Tyr Ile Ile Pro Leu
            740                 745                 750

Gln Gly Pro Gly Leu Thr Thr Thr Glu Ser Arg Gln Gln Pro Met Ala
        755                 760                 765

Leu Ala Val Ala Leu Thr Lys Gly Gly Glu Ala Arg Gly Glu Leu Phe
770                 775                 780

Trp Asp Asp Gly Glu Ser Leu Glu Val Leu Glu Arg Gly Ala Tyr Thr
785                 790                 795                 800

Gln Val Ile Phe Leu Ala Arg Asn Asn Thr Ile Val Asn Glu Leu Val
                805                 810                 815

Arg Val Thr Ser Glu Gly Ala Gly Leu Gln Leu Gln Lys Val Thr Val
            820                 825                 830

Leu Gly Val Ala Thr Ala Pro Gln Gln Val Leu Ser Asn Gly Val Pro
        835                 840                 845

Val Ser Asn Phe Thr Tyr Ser Pro Asp Thr Lys Val Leu Asp Ile Cys
850                 855                 860

Val Ser Leu Leu Met Gly Glu Gln Phe Leu Val Ser Trp Cys
865                 870                 875

<210> SEQ ID NO 37
<211> LENGTH: 2745
<212> TYPE: DNA
<213> ORGANISM: artificial
<220> FEATURE:
<223> OTHER INFORMATION: sp7+hGAAwt-delta-29

<400> SEQUENCE: 37
atggcctttc tgtggctgct gagctgttgg gccctgctgg caccaccttc ggccagcag      60 ggagccagca gaccagggcc ccgggatgcc caggcacacc ccggcggcc gcgagcagtg     120 cccacacagt gcgacgtccc ccccaacagc cgcttcgatt gccccctga caaggccatc     180 acccaggaac agtgcgaggc ccgcggctgt tgctacatcc ctgcaaagca ggggctgcag     240
ggagcccaga tggggcagcc ctggtgcttc ttcccaccca gctacccag ctacaagctg     300 gagaacctga gctcctctga aatgggctac acggccaccc tgacccgtac caccccacc     360 ttcttcccca aggacatcct gacccctgcg ctggacgtga tgatggagac tgagaaccgc     420
ctccacttca cgatcaaaga tccagctaac aggcgctacg aggtgccctt ggagaccccg     480
catgtccaca gccgggcacc gtccccactc tacagcgtgg agttctccga ggagcccttc     540
ggggtgatcg tgcgccggca gctggacggc cgcgtgctgc tgaacacgac ggtggcgccc     600
ctgttctttg cggaccagtt ccttcagctg tccacctcgc tgccctcgca gtatatcaca     660
ggcctcgccg agcacctcag tcccctgatg ctcagcacca gctggaccag gatcacccctg     720 tggaaccggg accttgcgcc cacgcccggt gcgaacctct acgggtctca cccttctac     780

```
ctggcgctgg aggacggcgg gtcggcacac ggggtgttcc tgctaaacag caatgccatg    840
gatgtggtcc tgcagccgag ccctgcccct agctggaggt cgacaggtgg gatcctggat    900
gtctacatct tcctgggccc agagcccaag agcgtggtgc agcagtacct ggacgttgtg    960
ggatacccgt tcatgccgcc atactggggc ctgggcttcc acctgtgccg ctggggctac   1020
tcctccaccg ctatcacccg ccaggtggtg gagaacatga ccagggccca cttcccctg    1080
gacgtccagt ggaacgacct ggactacatg gactcccgga gggacttcac gttcaacaag   1140
gatggcttcc gggacttccc ggccatggtg caggagctgc accagggcgg ccggcgctac   1200
atgatgatcg tggatcctgc catcagcagc tcgggccctg ccgggagcta caggccctac   1260
gacgagggtc tgcggagggg ggttttcatc accaacgaga ccggccagcc gctgattggg   1320
aaggtatggc ccgggtccac tgccttcccc gacttcacca cccccacagc cctggcctgg   1380
tgggaggaca tggtggctga gttccatgac caggtgccct cgacggcat gtggattgac   1440
atgaacgagc cttccaactt catcaggggc tctgaggacg gctgcccaa caatgagctg   1500
gagaacccac cctacgtgcc tggggtggtt gggggggaccc tccaggcggc caccatctgt   1560
gcctccagcc accagtttct ctccacacac tacaacctgc acaacctcta cggcctgacc   1620
gaagccatcg cctcccacag ggcgctggtg aaggctcggg ggacacgccc atttgtgatc   1680
tcccgctcga cctttgctgg ccacggccga tacgccggcc actggacggg ggacgtgtgg   1740
agctcctggg agcagctcgc ctcctccgtg ccagaaatcc tgcagtttaa cctgctgggg   1800
gtgcctctgg tcgggccga cgtctgcggc ttcctgggca cacctcaga ggagctgtgt   1860
gtgcgctgga cccagctggg ggccttctac cccttcatgc ggaaccacaa cagcctgctc   1920
agtctgcccc aggagccgta cagcttcagc gagccggccc agcaggccat gaggaaggcc   1980
ctcacccctgc gctacgcact cctccccccac ctctacacac tgttccacca ggcccacgtc   2040
gcggggggaga ccgtggcccg gcccctcttc ctggagttcc caaggactc tagcacctgg   2100
actgtggacc accagctcct gtgggggggag ccctgctca tcaccccagt gctccaggcc   2160
gggaaggccg aagtgactgg ctacttcccc ttgggcacat ggtacgacct gcagacggtg   2220
ccagtagagg cccttggcag cctcccaccc ccacctgcag ctccccgtga gccagccatc   2280
cacagcgagg ggcagtgggt gacgctgccg gccccctgg acaccatcaa cgtccacctc   2340
cgggctgggt acatcatccc cctgcagggc cctggcctca aaccacaga gtcccgccag   2400
cagcccatgg ccctggctgt ggccctgacc aagggtgggg aggcccgagg ggagctgttc   2460
tgggacgatg gagagagcct ggaagtgctg gagcgagggg cctacacaca ggtcatcttc   2520
ctggccagga ataacacgat cgtgaatgag ctggtacgtg tgaccagtga gggagctggc   2580
ctgcagctgc agaaggtgac tgtcctgggc gtggccacgg cgcccagca ggtcctctcc   2640
aacggtgtcc ctgtctccaa cttcacctac agccccgaca ccaaggtcct ggacatctgt   2700
gtctcgctgt tgatgggaga gcagtttctc gtcagctggt gttag                   2745
```

<210> SEQ ID NO 38
<211> LENGTH: 2745
<212> TYPE: DNA
<213> ORGANISM: artificial
<220> FEATURE:
<223> OTHER INFORMATION: sp7+hGAAco1-delta-29

<400> SEQUENCE: 38

```
atggcctttc tgtggctgct gagctgttgg gccctgctgg caccaccttt cggccagcag     60
ggcgcctcta gacctggacc tagagatgcc caggcccacc ccggcagacc tagagctgtg    120
```

```
cctacccagt gtgacgtgcc ccccaacagc agattcgact gcgcccctga caaggccatc    180
acccaggaac agtgcgaggc cagaggctgc tgctacatcc ctgccaagca gggactgcag    240
ggcgctcaga tgggacagcc ctggtgcttc ttcccaccct cctacccag ctacaagctg     300
gaaaacctga gcagcagcga gatgggctac accgccaccc tgaccagaac cacccccaca    360
ttcttcccaa aggacatcct gaccctgcgg ctggacgtga tgatggaaac cgagaaccgg    420
ctgcacttca ccatcaagga ccccgccaat cggagatacg aggtgcccct ggaaaccccc    480
cacgtgcact ctagagcccc cagccctctg tacagcgtgg aattcagcga ggaacccttc    540
ggcgtgatcg tgcggagaca gctggatggc agagtgctgc tgaacaccac cgtggcccct    600
ctgttcttcg ccgaccagtt cctgcagctg agcaccagcc tgcccagcca gtacatcaca    660
ggactggccg agcacctgag cccctgatg ctgagcacat cctggacccg gatcaccctg     720
tggaacaggg atctggcccc tacccctggc gccaatctgt acggcagcca cccttctac    780
ctggccctgg aagatggcgg atctgcccac ggagtgttc tgctgaactc caacgccatg     840
gacgtggtgc tgcagcctag ccctgccctg tcttggagaa gcacaggcgg catcctggat    900
gtgtacatct ttctgggccc cgagcccaag agcgtggtgc agcagtatct ggatgtcgtg    960
ggctacccct tcatgccccc ttactggggc ctgggattcc acctgtgcag atggggctac   1020
tccagcaccg ccatcaccag acaggtggtg gaaaacatga ccagagccca cttcccactg   1080
gatgtgcagt ggaacgacct ggactacatg gacagcagac gggacttcac cttcaacaag   1140
gacggcttcc gggacttccc cgccatggtg caggaactgc atcagggcgg cagacggtac   1200
atgatgatcg tggatcccgc catcagctcc tctggccctg ccggctctta cagaccctac   1260
gacgagggcc tgcggagagg cgtgttcatc accaacgaga caggccagcc cctgatcggc   1320
aaagtgtggc ctggcagcac agccttcccc gacttcacca tcctaccgc cctggcttgg    1380
tgggaggaca tggtggccga gttccacgac caggtgccct cgacggcat gtggatcgac    1440
atgaacgagc ccagcaactt catccggggc agcgaggatg gctgccccaa caacgaactg   1500
gaaaatcccc cttacgtgcc cggcgtcgtg ggcggaacac tgcaggccgc tacaatctgt   1560
gccagcagcc accagtttct gagcacccac tacaacctgc acaacctgta cggcctgacc   1620
gaggccattg ccagccaccg cgctctcgtg aaagccagag gcacacggcc cttcgtgatc   1680
agcagaagca ccttttgccgg ccacggcaga tacgccggac attggactgg cgacgtgtgg   1740
tcctcttggg agcagctggc ctctagcgtg cccgagatcc tgcagttcaa tctgctgggc   1800
gtgccactcg tgggcgccga tgtgtgtggc ttcctgggca cacctccga ggaactgtgt    1860
gtgcggtgga cacagctggg cgccttctac ccctttcatga gaaaccacaa cagcctgctg   1920
agcctgcccc aggaaccta cagctttagc gagcctgcac agcaggccat gcggaaggcc    1980
ctgacactga gatacgctct gctgccccac ctgtacaccc tgtttcacca ggcccatgtg   2040
gccggcgaga cagtggccag acctctgttt ctggaattcc caaggacag cagccacctgg   2100
accgtggacc atcagctgct gtggggagag gctctgctga ttaccccagt gctgcaggca   2160
ggcaaggccg aagtgaccgg ctactttccc ctgggcactt ggtacgacct gcagaccgtg   2220
cctgtggaag ccctgggatc tctgcctcca cctcctgccg ctcctagaga gcctgccatt   2280
cactctgagg gccagtgggt cacactgcct gcccccctgg ataccatcaa cgtgcacctg   2340
agggccggct acatcatacc actgcaggga cctggcctga ccaccaccga gtctagacag   2400
cagccaatgg ccctggccgt ggccctgacc aaaggcggag aagctagggg cgagctgttc   2460
```

| | |
|---|---|
| tgggacgatg gcgagagcct ggaagtgctg gaaagaggcg cctataccca agtgatcttc | 2520 |
| ctggcccgga acaacaccat cgtgaacgag ctggtgcgcg tgacctctga aggcgctgga | 2580 |
| ctgcagctgc agaaagtgac cgtgctggga gtggccacag cccctcagca ggtgctgtct | 2640 |
| aatggcgtgc ccgtgtccaa cttcacctac agccccgaca ccaaggtgct ggacatctgc | 2700 |
| gtgtcactgc tgatgggaga gcagtttctg gtgtcctggt gctga | 2745 |

<210> SEQ ID NO 39
<211> LENGTH: 2745
<212> TYPE: DNA
<213> ORGANISM: artificial
<220> FEATURE:
<223> OTHER INFORMATION: sp7+hGAAco2-delta-29

<400> SEQUENCE: 39

| | |
|---|---|
| atggccttc tgtggctgct gagctgttgg gccctgctgg gcaccacctt cggccaacag | 60 |
| ggagcttcca gaccaggacc gagagacgcc aagcccatc ctggtagacc aagagctgtg | 120 |
| cctacccaat gcgacgtgcc acccaactcc cgattcgact gcgcgccaga taaggctatt | 180 |
| acccaagagc agtgtgaagc cagaggttgc tgctacatcc cagcgaagca aggattgcaa | 240 |
| ggcgcccaaa tgggacaacc ttggtgtttc ttccccccctt cgtacccatc atataaactc | 300 |
| gaaaacctgt cctcttcgga aatgggttat actgccaccc tcaccagaac tactcctact | 360 |
| ttcttcccga aagacatctt gaccttgagg ctggacgtga tgatggagac tgaaaaccgg | 420 |
| ctgcatttca ctatcaaaga tcctgccaat cggcgatacg aggtccctct ggaaaccccct | 480 |
| cacgtgcact cacgggctcc ttctccgctt tactccgtcg aattctctga ggaaccttc | 540 |
| ggagtgatcg ttagacgcca gctggatggt agagtgctgt gaacactac tgtggcccca | 600 |
| ctttcttcg ctgaccagtt tctgcaactg tccacttcc tgccatccca gtacattact | 660 |
| ggactcgccg aacacctgtc gccactgatg ctctcgacct cttggactag aatcactttg | 720 |
| tgaacagag acttggcccc tactccggga gcaaatctgt acggaagcca ccctttttac | 780 |
| ctggcgctcg aagatggcgg atccgctcac ggagtgttcc tgctgaatag caacgcaatg | 840 |
| gacgtggtgc tgcaaccttc ccctgcactc agttggagaa gtaccggggg tattctggac | 900 |
| gtgtacatct tcctcggacc agaacccaag agcgtggtgc agcaatatct ggacgtggtc | 960 |
| ggataccctt ttatgcctcc ttactgggga ctgggattcc acctttgccg ttggggctac | 1020 |
| tcatccaccg ccattaccag acaggtggtg gagaatatga ccagagccca cttccctctc | 1080 |
| gacgtgcagt ggaacgatct ggactatatg gactcccgga gagatttcac cttcaacaag | 1140 |
| gacgggttcc gcgattttcc cgcgatggtt caagagctcc accagggtgg tcgaagatat | 1200 |
| atgatgatcg tcgacccagc catttcgagc agcggacccg ctggatctta tagaccttac | 1260 |
| gacgaaggcc ttaggagagg agtgttcatc acaaacgaga ctggacagcc tttgatcggt | 1320 |
| aaagtgtggc ctggatcaac cgcctttcct gactttacca atcccactgc cttggcttgg | 1380 |
| tgggaggaca tggtggccga attccacgac caagtcccct tgatggaat gtggatcgat | 1440 |
| atgaacgaac caagcaattt tatcagaggt tccgaagacg gttgccccaa caacgaactg | 1500 |
| gaaaaccctc cttatgtgcc cggagtcgtg ggcggaacat acaggccgc gactatttgc | 1560 |
| gccagcagcc accaattcct gtccactcac tacaacctcc acaacctta tggattaacc | 1620 |
| gaagctattg caagtcacag ggctctggtg aaggctagag ggactaggcc ctttgtgatc | 1680 |
| tcccgatcca ccttgccgg acacgggaga tacgccggtc actggactgg tgacgtgtgg | 1740 |
| agctcatggg aacaactggc ctcctccgtg ccggaaatct acagttcaa ccttctgggt | 1800 |

-continued

```
gtccctcttg tcggagcaga cgtgtgtggg tttcttggta acacctccga ggaactgtgt    1860
gtgcgctgga ctcaactggg tgcattctac ccattcatga gaaaccacaa ctccttgctg    1920
tccctgccac aagagcccta ctcgttcagc gagcctgcac aacaggctat gcggaaggca    1980
ctgaccctga gatacgccct gcttccacac ttatacactc tcttccatca agcgcatgtg    2040
gcaggagaaa ccgttgcaag gcctctttc cttgaattcc caaggattc ctcgacttgg      2100 acggtggatc atcagctgct gtggggagaa gctctgctga ttactccagt gttgcaagcc    2160
ggaaaagctg aggtgaccgg atactttccg ctgggaacct ggtacgacct ccagactgtc    2220
cctgttgaag cccttggatc actgcctccg cctccggcag ctccacgcga accagctata    2280
cattccgagg gacagtgggt tacattacca gctcctctgg acacaatcaa cgtccactta    2340
agagctggct acattatccc tctgcaagga ccaggactga ctacgaccga gagcagacag    2400
cagccaatgg cactggctgt ggctctgacc aagggagggg aagctagagg agaactcttc    2460
tgggatgatg gggagtccct tgaagtgctg gaaagaggcg cttacactca agtcattttc    2520
cttgcacgga caacaccat tgtgaacgaa ttggtgcgag tgaccagcga aggagctgga    2580
cttcaactgc agaaggtcac tgtgctcgga gtggctaccg ctcctcagca agtgctgtcg    2640
aatggagtcc ccgtgtcaaa ctttacctac tcccctgaca ctaaggtgct cgacatttgc    2700
gtgtccctcc tgatgggaga gcagttcctt gtgtcctggt gttga                   2745
```

<210> SEQ ID NO 40
<211> LENGTH: 2706
<212> TYPE: DNA
<213> ORGANISM: artificial
<220> FEATURE:
<223> OTHER INFORMATION: sp7+hGAAwt-delta-42

<400> SEQUENCE: 40

```
atggcctttc tgtggctgct gagctgttgg gccctgctgg caccaccttc ggcgcacac     60 cccgggcggc cgcgagcagt gcccacacag tgcgacgtcc ccccaacag ccgcttcgat     120 tgcgccctg acaaggccat cacccaggaa cagtgcgagg cccgcggctg ttgctacatc     180
cctgcaaagc aggggctgca gggagcccag atggggcagc cctggtgctt cttcccaccc    240
agctacccca gctacaagct ggagaacctg agctcctctg aaatgggcta cacggccacc    300
ctgacccgta ccaccccac cttcttcccc aaggacatcc tgaccctgcg gctggacgtg    360
atgatggaga ctgagaaccg cctccacttc acgatcaaag atccagctaa caggcgctac   420
gaggtgccct ggagaccccc gcatgtccac agccgggcac cgtccccact ctacagcgtg    480
gagttctccg aggagcccctt cggggtgatc gtgcgccggc agctggacgg ccgcgtgctg    540
ctgaacacga cggtggcgcc cctgttcttt gcggaccagt ccttcagct gtccacctcg    600 ctgccctcgc agtatatcac aggcctcgcc gagcacctca gtcccctgat gctcagcacc    660
agctggacca ggatcaccct gtggaaccgg accttgcgc ccacgcccgg tcgaacctc     720 tacgggtctc acccttcta cctggcgctg gaggacggcg gtcggcaca cggggtgttc    780 ctgctaaaca gcaatgccat ggatgtggtc ctgcagccga gccctgccct tagctggagg    840
tcgacaggtg ggatcctgga tgtctacatc ttcctgggcc cagagcccaa gagcgtggtg    900
cagcagtacc tggacgttgt gggataccg ttcatgccgc catactgggg cctgggcttc    960
cacctgtgcc gctggggcta ctcctccacc gctataccc gccaggtggt ggagaacatg    1020
accagggccc acttccccct ggacgtccag tggaacgacc tggactacat ggactcccgg    1080
```

| | |
|---|---|
| agggacttca cgttcaacaa ggatggcttc cgggacttcc cggccatggt gcaggagctg | 1140 |
| caccagggcg gccggcgcta catgatgatc gtggatcctg ccatcagcag ctcgggccct | 1200 |
| gccgggagct acaggcccta cgacgagggt ctgcggaggg gggttttcat caccaacgag | 1260 |
| accggccagc cgctgattgg gaaggtatgg cccgggtcca ctgccttccc cgacttcacc | 1320 |
| aaccccacag ccctggcctg gtgggaggac atggtggctg agttccatga ccaggtgccc | 1380 |
| ttcgacggca tgtggattga catgaacgag ccttccaact tcatcagggg ctctgaggac | 1440 |
| ggctgcccca acaatgagct ggagaaccca ccctacgtgc tggggtggt tgggggacc | 1500 |
| ctccaggcgg ccaccatctg tgcctccagc caccagtttc tctccacaca ctacaacctg | 1560 |
| cacaacctct acggcctgac cgaagccatc gcctcccaca gggcgctggt gaaggctcgg | 1620 |
| gggacacgcc catttgtgat ctcccgctcg acctttgctg ccacggccg atacgccggc | 1680 |
| cactggacgg gggacgtgtg gagctcctgg gagcagctcg cctcctccgt gccagaaatc | 1740 |
| ctgcagttta acctgctggg ggtgcctctg gtcggggccg acgtctgcgg cttcctgggc | 1800 |
| aacacctcag aggagctgtg tgtgcgctgg acccagctgg gggccttcta ccccttcatg | 1860 |
| cggaaccaca acagcctgct cagtctgccc caggagccgt acagcttcag cgagccggcc | 1920 |
| cagcaggcca tgaggaaggc cctcacctg cgctacgcac tcctccccca cctctacaca | 1980 |
| ctgttccacc aggcccacgt cgcggggggag accgtggccc ggcccctctt cctggagttc | 2040 |
| cccaaggact ctagcacctg gactgtggac caccagctcc tgtgggggga ggccctgctc | 2100 |
| atcaccccag tgctccaggc cgggaaggcc gaagtgactg gctacttccc cttgggcaca | 2160 |
| tggtacgacc tgcagacggt gccagtagag gcccttggca gctcccacc cccacctgca | 2220 |
| gctccccgtg agccagccat ccacagcgag gggcagtggg tgacgctgcc ggccccctg | 2280 |
| gacaccatca cgtccacct ccgggctggg tacatcatcc cctgcaggg ccctggcctc | 2340 |
| acaaccacag agtcccgcca gcagcccatg gccctggctg tggccctgac caagggtggg | 2400 |
| gaggcccgag gggagctgtt ctgggacgat ggagagagcc tggaagtgct ggagcgaggg | 2460 |
| gcctacacac aggtcatctt cctggccagg aataacacga tcgtgaatga gctggtacgt | 2520 |
| gtgaccagtg agggagctgg cctgcagctg cagaaggtga ctgtcctggg cgtggccacg | 2580 |
| gcgccccagc aggtcctctc caacggtgtc cctgtctcca acttcaccta cagccccgac | 2640 |
| accaaggtcc tggacatctg tgtctcgctg ttgatgggag agcagtttct cgtcagctgg | 2700 |
| tgttag | 2706 |

<210> SEQ ID NO 41
<211> LENGTH: 2706
<212> TYPE: DNA
<213> ORGANISM: artificial
<220> FEATURE:
<223> OTHER INFORMATION: sp7-hGAAco2-delta-42

<400> SEQUENCE: 41

| | |
|---|---|
| atggcctttc tgtggctgct gagctgttgg gccctgctgg gcaccacctt cggcgcccat | 60 |
| cctggtagac caagagctgt gcctacccaa tgcgacgtgc acccaactc ccgattcgac | 120 |
| tgcgcgccag ataaggctat tacccaagag cagtgtgaag ccagaggttg ctgctacatc | 180 |
| ccagcgaagc aaggattgca aggcgcccaa atgggacaac cttggtgttt cttccccct | 240 |
| tcgtacccat catataaact cgaaaacctg tcctcttcgg aaatgggtta tactgccacc | 300 |
| ctcaccagaa ctactcctac tttcttcccg aaagacatct tgaccttgag gctggacgtg | 360 |
| atgatggaga ctgaaaaccg gctgcatttc actatcaaag atcctgccaa tcggcgatac | 420 |

```
gaggtccctc tggaaacccc tcacgtgcac tcacgggctc cttctccgct ttactccgtc    480
gaattctctg aggaacccu cggagtgatc gttagacgcc agctggatgg tagagtgctg    540
ttgaacacta ctgtggcccc acttttcttc gctgaccagt ttctgcaact gtccacttcc    600
ctgccatccc agtacattac tggactcgcc gaacacctgt cgccactgat gctctcgacc    660
tcttggacta gaatcacttt gtggaacaga gacttggccc ctactccggg agcaaatctg    720 tacgaagcc accccttttta cctggcgctc gaagatggcg gatccgctca cggagtgttc    780
ctgctgaata gcaacgcaat ggacgtggtg ctgcaacctt ccctgcact cagttggaga    840 agtaccgggg gtattctgga cgtgtacatc ttcctcggac cagaacccaa gagcgtggtg    900
cagcaatatc tggacgtggt cggatacct tttatgcctc cttactgggg actgggatc    960 cacctttgcc gttggggcta ctcatccacc gccattacca gacaggtggt ggagaatatg    1020
accagagccc acttccctct cgacgtgcag tggaacgatc tggactatat ggactcccgg    1080
agagatttca ccttcaacaa ggacgggttc cgcgattttc ccgcgatggt tcaagagctc    1140
caccagggtg gtcgaagata tatgatgatc gtcgacccag ccatttcgag cagcggaccc    1200
gctggatctt atagacctta cgacgaaggc cttaggagag gagtgttcat cacaaacgag    1260
actggacagc ctttgatcgg taaagtgtgg cctggatcaa ccgccttttc tgactttacc    1320
aatcccactg cctggcttg tgggaggac atggtggccg aattccacga ccaagtcccc    1380
tttgatggaa tgtggatcga tatgaacgaa ccaagcaatt ttatcagagg ttccgaagac    1440
ggttgcccca acaacgaact ggaaaaccct ccttatgtgc ccggagtcgt gggcggaaca    1500
ttacaggccg cgactatttg cgccagcagc caccaattcc tgtccactca ctacaacctc    1560 cacaacctt atggattaac cgaagctatt gcaagtcaca gggctctggt gaaggctaga    1620
gggactaggc cctttgtgat ctcccgatcc acctttgccg gacacgggag atacgccggt    1680
cactggactg gtgacgtgtg gagctcatgg gaacaactgg cctcctccgt gccggaaatc    1740
ttacagttca accttctggg tgtccctctt gtcggagcag acgtgtgtgg gtttcttggt    1800
aacacctccg aggaactgtg tgtgcgctgg actcaactgg gtgcattcta cccattcatg    1860
agaaaccaca actccttgct gtccctgcca caagagccct actcgttcag cgagcctgca    1920
caacaggcta tgcggaaggc actgaccctg agatacgccc tgcttccaca cttatacact    1980
ctcttccatc aagcgcatgt ggcaggagaa accgttgcaa ggcctctttt ccttgaattc    2040
cccaaggatt cctcgacttg gacggtggat catcagctgc tgtggggaga agctctgctg    2100
attactccag tgttgcaagc cggaaaaagct gaggtgaccg atactttcc gctgggaacc    2160 tggtacgacc tccagactgt ccctgttgaa gcccttggat cactgcctcc gcctccggca    2220
gctccacgcg aaccagctat acattccgag ggacagtggg ttacattacc agctcctctg    2280
gacacaatca acgtccactt aagagctggc tacattatcc ctctgcaagg accaggactg    2340
actacgaccg agagcagaca gcagccaatg gcactggctg tggctctgac caagggaggg    2400
gaagctagag gagaactctt ctgggatgat ggggagtccc ttgaagtgct ggaaagaggc    2460
gcttacactc aagtcatttt ccttgcacgg aacaacacca ttgtgaacga attggtgcga    2520
gtgaccagcg aaggagctgg acttcaactg cagaaggtca ctgtgctcgg agtggctacc    2580
gctcctcagc aagtgctgtc gaatggagtc cccgtgtcaa actttaccta ctcccctgac    2640
actaaggtgc tcgacatttg cgtgtccctc ctgatgggag agcagttcct tgtgtcctgg    2700
tgttga                                                              2706
```

<210> SEQ ID NO 42
<211> LENGTH: 2703
<212> TYPE: DNA
<213> ORGANISM: artificial
<220> FEATURE:
<223> OTHER INFORMATION: sp7-hGAAwt-delta-43

<400> SEQUENCE: 42

```
atggcctttc tgtggctgct gagctgttgg gccctgctgg gcaccacctt cggccacccc      60
gggcggccgc gagcagtgcc cacacagtgc gacgtccccc ccaacagccg cttcgattgc     120
gcccctgaca aggccatcac ccaggaacag tgcgaggccc gcggctgttg ctacatccct     180
gcaaagcagg ggctgcaggg agcccagatg gggcagcccg gtgcttcttc ccacccagc     240
tacccccagct acaagctgga gaacctgagc tcctctgaaa tgggctacac ggccaccctg     300
acccgtacca ccccccacctt cttccccaag gacatcctga ccctgcggct ggacgtgatg     360
atggagactg agaaccgcct ccacttcacg atcaaagatc cagctaacag gcgctacgag     420
gtgcccttgg agaccccgca tgtccacagc cgggcaccgt ccccactcta cagcgtggag     480
ttctccgagg agcccttcgg ggtgatcgtg cgccggcagc tggacggccg cgtgctgctg     540
aacacgacgg tggcgcccct gttctttgcg gaccagttcc ttcagctgtc cacctcgctg     600
ccctcgcagt atatcacagg cctcgccgag cacctcagtc cctgatgct cagcaccagc     660
tggaccagga tcaccctgtg gaaccgggac cttgcgccca cgcccggtgc gaacctctac     720
gggtctcacc ctttctacct ggcgctggag gacggcgggt cggcacacgg ggtgttcctg     780
ctaaacagca tgccatgga tgtggtcctg cagccgagcc ctgcccttag ctggaggtcg     840
acaggtggga tcctggatgt ctacatcttc ctgggcccag agcccaagag cgtggtgcag     900
cagtacctgg acgttgtggg ataccgttc atgccgccat actggggcct gggcttccac     960
ctgtgccgct ggggctactc ctccaccgct atcacccgcc aggtggtgga aaccatgacc    1020
agggcccact cccccctgga cgtccagtgg aacgacctgg actacatgga ctcccggagg    1080
gacttcacgt tcaacaagga tggcttccgg gacttcccgg ccatggtgca ggagctgcac    1140
cagggcggcc ggcgctacat gatgatcgtg gatcctgcca tcagcagctc gggccctgcc    1200
gggagctaca ggccctacga cgagggtctg cggaggggg ttttcatcac caacgagacc    1260
ggccagccgc tgattgggaa ggtatggccc ggtccactg ccttccccga cttcaccaac    1320
cccacagccc tggcctggtg ggaggacatg gtggctgagt ccatgacca ggtgcccttc    1380
gacggcatgt ggattgacat gaacgagcct tccaacttca tcaggggctc tgaggacggc    1440
tgccccaaca atgagctgga aaacccaccc tacgtgcctg gggtggttgg ggggaccctc    1500
caggcggcca ccatctgtgc ctccagccac cagtttctct ccacacacta caacctgcac    1560
aacctctacg gcctgaccga agccatcgcc tcccacaggg cgctggtgaa ggctcggggg    1620
acacgcccat ttgtgatctc ccgctcgacc tttgctggcc acggccgata cgccggccac    1680
tggacggggg acgtgtggag ctcctgggag cagctcgcct cctccgtgcc agaaatcctg    1740
cagtttaacc tgctgggggt gcctctggtc ggggccgacg tctgcggctt cctgggcaac    1800
acctcagagg agctgtgtgt gcgctggacc cagctggggg ccttctaccc cttcatgcgg    1860
aaccacaaca gcctgctcag tctgccccag gagccgtaca gcttcagcga gccggcccag    1920
caggccatga ggaaggccct cacccctgcgc tacgcactcc tccccacct ctacacactg    1980
ttccaccagg cccacgtcgc gggggagacc gtggcccggc cctcttcct ggagttcccc    2040
aaggactcta gcacctggac tgtggaccac cagctcctgt gggggggaggc cctgctcatc    2100
```

-continued

| | |
|---|---|
| acccccagtgc tccaggccgg gaaggccgaa gtgactggct acttcccctt gggcacatgg | 2160 |
| tacgacctgc agacggtgcc agtagaggcc cttggcagcc tcccaccccc acctgcagct | 2220 |
| ccccgtgagc cagccatcca cagcgagggg cagtgggtga cgctgccggc cccctggac | 2280 |
| accatcaacg tccacctccg ggctgggtac atcatccccc tgcagggccc tggcctcaca | 2340 |
| accacagagt cccgccagca gcccatggcc ctggctgtgg ccctgaccaa gggtggggag | 2400 |
| gcccgagggg agctgttctg ggacgatgga gagagcctgg aagtgctgga gcgaggggcc | 2460 |
| tacacacagg tcatcttcct ggccaggaat aacacgatcg tgaatgagct ggtacgtgtg | 2520 |
| accagtgagg gagctggcct gcagctgcag aaggtgactg tcctgggcgt ggccacggcg | 2580 |
| ccccagcagg tcctctccaa cggtgtccct gtctccaact tcacctacag ccccgacacc | 2640 |
| aaggtcctgg acatctgtgt ctcgctgttg atgggagagc agtttctcgt cagctggtgt | 2700 |
| tag | 2703 |

<210> SEQ ID NO 43
<211> LENGTH: 2703
<212> TYPE: DNA
<213> ORGANISM: artificial
<220> FEATURE:
<223> OTHER INFORMATION: sp7+hGAAco1-delta-43

<400> SEQUENCE: 43

| | |
|---|---|
| atggcctttc tgtggctgct gagctgttgg gccctgctgg caccaccttc ggccaccccc | 60 |
| ggcagaccta gagctgtgcc tacccagtgt gacgtgcccc caacagcag attcgactgc | 120 |
| gccctgaca aggccatcac ccaggaacag tgcgaggcca gagctgctg ctacatccct | 180 |
| gccaagcagg gactgcaggg cgctcagatg ggacagccct ggtgcttctt ccacccctcc | 240 |
| taccccagct acaagctgga aacctgagc agcagcgaga tgggctacac cgccaccctg | 300 |
| accagaacca ccccccacatt cttcccaaag gacatcctga ccctgcggct ggacgtgatg | 360 |
| atggaaaccg agaaccggct gcacttcacc atcaaggacc ccgccaatcg agatacgag | 420 |
| gtgcccctgg aaacccccca cgtgcactct agagccccca gccctctgta cagcgtggaa | 480 |
| ttcagcgagg aacccttcgg cgtgatcgtg cggagacagc tggatggcag agtgctgctg | 540 |
| aacaccaccg tggcccctct gttcttcgcc gaccagttcc tgcagctgag caccagcctg | 600 |
| cccagccagt acatcacagg actggccgag cacctgagcc cctgatgct gagcacatcc | 660 |
| tggacccgga tcaccctgtg aacagggat ctggcccta ccctggcgc aatctgtac | 720 |
| ggcagccacc ctttctacct ggccctggaa gatggcggat ctgccacgg agtgtttctg | 780 |
| ctgaactcca acgccatgga cgtggtgctg cagcctagcc ctgccctgtc ttggagaagc | 840 |
| acaggcggca tcctggatgt gtacatcttt ctgggcccg agcccaagag cgtggtgcag | 900 |
| cagtatctgg atgtcgtggg ctacccttc atgcccct actggggcct gggattccac | 960 |
| ctgtgcagat ggggctactc cagcaccgcc atcaccagac aggtggtgga aaacatgacc | 1020 |
| agagcccact tccactgga tgtgcagtgg aacgacctgg actacatgga cagcagacgg | 1080 |
| gacttcacct tcaacaagga cggcttccgg gacttcccg ccatggtgca ggaactgcat | 1140 |
| cagggcggca gacggtacat gatgatcgtg gatcccgcca tcagctcctc tggccctgcc | 1200 |
| ggctcttaca gaccctacga cgagggcctg cggagaggcg tgttcatcac caacgagaca | 1260 |
| ggccagcccc tgatcggcaa agtgtggcct ggcagcacag ccttccccga cttcaccaat | 1320 |
| cctaccgccc tggcttggtg ggaggacatg gtggccgagt ccacgacca ggtgcccttc | 1380 |

| | |
|---|---|
| gacggcatgt ggatcgacat gaacgagccc agcaacttca tccggggcag cgaggatggc | 1440 |
| tgccccaaca acgaactgga aaatccccct tacgtgcccg cgtcgtgggc cggaacactg | 1500 |
| caggccgcta caatctgtgc cagcagccac cagtttctga gcacccacta caacctgcac | 1560 |
| aacctgtacg gcctgaccga ggccattgcc agccaccgcg ctctcgtgaa agccagaggc | 1620 |
| acacggccct tcgtgatcag cagaagcacc tttgccggcc acggcagata cgccggacat | 1680 |
| tggactggcg acgtgtggtc ctcttgggag cagctggcct ctagcgtgcc cgagatcctg | 1740 |
| cagttcaatc tgctgggcgt gccactcgtg ggcgccgatg tgtgtggctt cctgggcaac | 1800 |
| acctccgagg aactgtgtgt gcggtggaca cagctgggcg ccttctaccc tttcatgaga | 1860 |
| aaccacaaca gcctgctgag cctgccccag gaaccctaca gctttagcga gcctgcacag | 1920 |
| caggccatgc ggaaggccct gacactgaga tacgctctgc tgccccacct gtacaccctg | 1980 |
| tttcaccagg cccatgtggc cggcgagaca gtggccagac tctgtttct ggaattcccc | 2040 |
| aaggacagca gcacctggac cgtgaccat cagctgctgt ggggagaggc tctgctgatt | 2100 |
| accccagtgc tgcaggcagg caaggccgaa gtgaccggca ctttcccct gggcacttgg | 2160 |
| tacgacctgc agaccgtgcc tgtggaagcc ctgggatctc tgcctccacc tcctgccgct | 2220 |
| cctagagagc ctgccattca ctctgagggc cagtgggtca cactgcctgc cccctggat | 2280 |
| accatcaacg tgcacctgag ggccggctac atcataccac tgcagggacc tggcctgacc | 2340 |
| accaccgagt ctagacagca gccaatggcc ctggccgtgg ccctgaccaa aggcggagaa | 2400 |
| gctaggggcg agctgttctg gacgatggc gagagcctgg aagtgctgga agaggcgcc | 2460 |
| tatacccaag tgatcttcct ggcccggaac aacaccatcg tgaacgagct ggtgcgcgtg | 2520 |
| acctctgaag gcgctggact gcagctgcag aaagtgaccg tgctgggagt ggccacagcc | 2580 |
| cctcagcagg tgctgtctaa tggcgtgccc gtgtccaact tcacctacag ccccgacacc | 2640 |
| aaggtgctgg acatctgcgt gtcactgctg atgggagagc agtttctggt gtcctggtgc | 2700 |
| tga | 2703 |

<210> SEQ ID NO 44
<211> LENGTH: 2703
<212> TYPE: DNA
<213> ORGANISM: artificial
<220> FEATURE:
<223> OTHER INFORMATION: sp7+hGAAco2-delta-43

<400> SEQUENCE: 44

| | |
|---|---|
| atggcctttc tgtggctgct gagctgttgg gccctgctgg caccaccttt cggccatcct | 60 |
| ggtagaccaa gagctgtgcc tacccaatgc gacgtgccac ccaactcccg attcgactgc | 120 |
| gcgccagata aggctattac ccaagagcag tgtgaagcca gaggttgctg ctacatccca | 180 |
| gcgaagcaag gattgcaagg cgcccaaatg ggacaacctt ggtgtttctt cccccttcg | 240 |
| tacccatcat ataaactcga aaacctgtcc tcttcggaaa tgggttatac tgccacctc | 300 |
| accagaacta ctcctacttt cttcccgaaa gacatcttga ccttgaggct ggacgtgatg | 360 |
| atggagactg aaaaccggct gcatttcact atcaaagatc ctgccaatcg gcgatacgag | 420 |
| gtccctctgg aaacccctca cgtgcactca cgggctcctt ctccgctta ctccgtcgaa | 480 |
| ttctctgagg aaccctcgg agtgatcgtt agacgccagc tggatggtag agtgctgttg | 540 |
| aacactactg tggcccccac tttcttcgct gaccagtttc tgcaactgtc cacttccctg | 600 |
| ccatcccagt acattactgg actcgccgaa cacctgtcgc cactgatgct ctcgacctct | 660 |
| tggactagaa tcactttgtg gaacagagac ttggccccta ctccgggagc aaatctgtac | 720 |

```
ggaagccacc cttttacct ggcgctcgaa gatggcggat ccgctcacgg agtgttcctg    780
ctgaatagca acgcaatgga cgtggtgctg caaccttccc ctgcactcag ttggagaagt    840
accgggggta ttctggacgt gtacatcttc ctcggaccag aacccaagag cgtggtgcag    900
caatatctgg acgtggtcgg ataccctttt atgcctcctt actggggact gggattccac    960
ctttgccgtt ggggctactc atccaccgcc attaccagac aggtggtgga gaatatgacc   1020
agagcccact ccctctcga cgtgcagtgg aacgatctgg actatatgga ctcccggaga   1080
gatttcacct tcaacaagga cgggttccgc gattttcccg cgatggttca agagctccac   1140
cagggtggtc gaagatatat gatgatcgtc gacccagcca tttcgagcag cggacccgct   1200
ggatcttata gaccttacga cgaaggcctt aggagaggag tgttcatcac aaacgagact   1260
ggacagcctt tgatcggtaa agtgtggcct ggatcaaccg cctttcctga ctttaccaat   1320
cccactgcct tggcttggtg ggaggacatg gtggccgaat ccacgacca gtcccctttt   1380 gatggaatgt ggatcgatat gaacgaacca agcaatttta tcagaggttc cgaagacggt   1440
tgccccaaca acgaactgga aaaccctcct tatgtgcccg gagtcgtggg cggaacatta   1500
caggccgcga ctatttgcgc cagcagccac caattcctgt ccactcacta aacctccac   1560 aacctttatg gattaaccga agctattgca agtcacaggg ctctggtgaa ggctagaggg   1620
actaggcccc ttgtgatctc ccgatccacc tttgccggac acgggagata cgccggtcac   1680
tggactggtg acgtgtggag ctcatgggaa caactggcct cctccgtgcc ggaaatctta   1740
cagttcaacc ttctgggtgt ccctcttgtc ggagcagacg tgtgtgggtt tcttggtaac   1800
acctccgagg aactgtgtgt gcgctggact caactgggtg cattctaccc attcatgaga   1860
aaccacaact ccttgctgtc cctgccacaa gagccctact cgttcagcga gcctgcacaa   1920
caggctatgc ggaaggcact gacccctgaga tacgccctgc ttccacactt atacactctc   1980
ttccatcaag cgcatgtggc aggagaaacc gttgcaaggc ctcttttcct tgaattcccc   2040
aaggattcct cgacttggac ggtggatcat cagctgctgt ggggagaagc tctgctgatt   2100
actccagtgt tgcaagccgg aaaagctgag gtgaccggat actttccgct gggaacctgg   2160
tacgacctcc agactgtccc tgttgaagcc cttggatcac tgcctccgcc tcggcagct   2220 ccacgcgaac cagctataca ttccgaggga cagtgggtta cattaccagc tcctctggac   2280
acaatcaacg tccacttaag agctggctac attatccctc tgcaaggacc aggactgact   2340
acgaccgaga gcagacagca gccaatggca ctggctgtgg ctctgaccaa gggaggggaa   2400
gctagaggag aactcttctg ggatgatggg gagtcccttg aagtgctgga agaggcgct   2460 tacactcaag tcattttcct tgcacggaac acaccattg tgaacgaatt ggtgcgagtg   2520
accagcgaag gagctggact tcaactgcag aaggtcactg tgctcggagt ggctaccgct   2580
cctcagcaag tgctgtcgaa tggagtcccc gtgtcaaact ttacctactc ccctgacact   2640
aaggtgctcg acatttgcgt gtccctcctg atgggagagc agttccttgt gtcctggtgt   2700
tga                                                                2703
```

<210> SEQ ID NO 45
<211> LENGTH: 2691
<212> TYPE: DNA
<213> ORGANISM: artificial
<220> FEATURE:
<223> OTHER INFORMATION: sp7+hGAAwt-delta-47

<400> SEQUENCE: 45

```
atggcctttc tgtggctgct gagctgttgg gccctgctgg gcaccacctt cggcccgcga    60
gcagtgccca cacagtgcga cgtcccccc aacagccgct tcgattgcgc ccctgacaag    120
gccatcaccc aggaacagtg cgaggcccgc ggctgttgct acatccctgc aaagcagggg    180
ctgcagggag cccagatggg gcagccctgg tgcttcttcc cacccagcta ccccagctac    240
aagctggaga acctgagctc ctctgaaatg ggctacacgg ccaccctgac ccgtaccacc    300
cccaccttct tccccaagga catcctgacc ctgcggctgg acgtgatgat ggagactgag    360
aaccgcctcc acttcacgat caaagatcca gctaacaggc gctacgaggt gcccttggag    420
accccgcatg tccacagccg ggcaccgtcc ccactctaca gcgtggagtt ctccgaggag    480
cccttcgggg tgatcgtgcg ccggcagctg gacggccgcg tgctgctgaa cacgacggtg    540
gcgcccctgt tctttgcgga ccagttcctt cagctgtcca cctcgctgcc ctcgcagtat    600
atcacaggcc tcgccgagca cctcagtccc ctgatgctca gcaccagctg gaccaggatc    660
accctgtgga accgggacct tgcgcccacg cccggtgcga acctctacgg gtctcaccct    720
ttctacctgg cgctggagga cggcgggtcg gcacacgggg tgttcctgct aaacagcaat    780
gccatggatg tggtcctgca gccgagccct gcccttagct ggaggtcgac aggtgggatc    840
ctggatgtct acatcttcct gggcccagag cccaagagcg tggtgcagca gtacctggac    900
gttgtgggat accgttcat gccgccatac tggggcctgg gcttccacct gtgccgctgg    960
ggctactcct ccaccgctat cacccgccag gtggtgagaa acatgaccag ggcccacttc    1020
cccctggacg tccagtggaa cgacctggac tacatggact cccggaggga cttcacgttc    1080
aacaaggatg gcttccggga cttcccggcc atggtgcagg agctgcacca gggcggccgg    1140
cgctacatga tgatcgtgga tcctgccatc agcagctcgg gccctgccgg gagctacagg    1200
ccctacgacg agggtctgcg gagggggtt ttcatcacca acgagaccgg ccagccgctg    1260
attgggaagg tatggcccgg gtccactgcc ttccccgact caccaacccc cacagccctg    1320
gcctggtggg aggacatggt ggctgagttc catgaccagg tgcccttcga cggcatgtgg    1380
attgacatga acgagccttc caacttcatc aggggctctg aggacggctg ccccaacaat    1440
gagctggaga acccacccta cgtgcctggg gtggttgggg ggaccctcca ggcggccacc    1500
atctgtgcct ccagccacca gtttctctcc acacactaca acctgcacaa cctctacggc    1560
ctgaccgaag ccatcgcctc ccacagggcg ctggtgaagg ctcgggggac acgcccattt    1620
gtgatctccc gctcgacctt tgctggccac ggccgatacg ccggccactg gacgggggac    1680
gtgtggagct cctgggagca gctcgcctcc tccgtgccag aaatcctgca gtttaacctg    1740
ctgggggtgc ctctggtcgg ggccgacgtc tgcggcttcc tgggcaacac ctcagaggag    1800
ctgtgtgtgc gctggaccca gctggggggcc ttctaccccct tcatgcggaa ccacaacagc    1860
ctgctcagtc tgccccagga gccgtacagc ttcagcgagc cggcccagca ggccatgagg    1920
aaggccctca ccctgcgcta cgcactcctc ccccacctct acacactgtt ccaccaggcc    1980
cacgtcgcgg gggagaccgt ggcccggccc ctcttcctgg agttccccaa ggactctagc    2040
acctggactg tggaccacca gctcctgtgg ggggaggccc tgctcatcac cccagtgctc    2100
caggccggga aggccgaagt gactggctac ttccccttgg gcatatggta cgacctgcag    2160
acggtgccag tagaggccct tggcagcctc ccacccccac ctgcagctcc ccgtgagcca    2220
gccatccaca gcgaggggca gtgggtgacg ctgccggccc cctggacac catcaacgtc    2280
cacctccggg ctgggtacat catcccctg cagggcctg gcctcacaac cacagagtcc    2340
cgccagcagc ccatggccct ggctgtggcc ctgaccaagg tggggaggc ccgaggggag    2400
```

```
ctgttctggg acgatggaga gagcctggaa gtgctggagc gaggggccta cacacaggtc    2460
atcttcctgg ccaggaataa cacgatcgtg aatgagctgg tacgtgtgac cagtgaggga    2520
gctggcctgc agctgcagaa ggtgactgtc ctgggcgtgg ccacggcgcc ccagcaggtc    2580
ctctccaacg gtgtccctgt ctccaacttc acctacagcc ccgacaccaa ggtcctggac    2640
atctgtgtct cgctgttgat gggagagcag tttctcgtca gctggtgtta g             2691
```

<210> SEQ ID NO 46
<211> LENGTH: 2691
<212> TYPE: DNA
<213> ORGANISM: artificial
<220> FEATURE:
<223> OTHER INFORMATION: sp7+hGAAco1-delta-47

<400> SEQUENCE: 46

```
atggccttc tgtggctgct gagctgttgg gccctgctgg caccaccttc ggccctaga      60 gctgtgccta cccagtgtga cgtgcccccc aacagcagat cgactgcgc ccctgacaag    120 gccatcaccc aggaacagtg cgaggccaga ggctgctgct acatccctgc caagcaggga   180
ctgcagggcg ctcagatggg acagccctgg tgcttcttcc caccctccta ccccagctac   240
aagctggaaa acctgagcag cagcgagatg ggctacaccg ccaccctgac cagaaccacc   300
cccacattct cccaaagga catcctgacc ctgcggctgg acgtgatgat ggaaaccgag   360
aaccggctgc acttcaccat caaggacccc gccaatcgga gatacgaggt gccctggaa    420 accccccacg tgcactctag agccccccagc cctctgtaca gcgtggaatt cagcgaggaa   480
cccttcggcg tgatcgtgcg agacagctg atggcagag tgctgctgaa caccaccgtg    540
gcccctctgt cttcgccga ccagttcctg cagctgagca ccagcctgcc cagccagtac    600
atcacaggac tggccgagca cctgagcccc ctgatgctga gcacatcctg acccggatc    660 accctgtgga caggggatct ggcccctacc cctggcgcca atctgtacgg cagccaccct   720
ttctacctgg ccctggaaga tggcggatct gcccacggag tgtttctgct gaactccaac   780
gccatggacg tggtgctgca gcctagccct gccctgtctt ggagaagcac aggcggcatc   840
ctggatgtgt acatctttct gggccccgag cccaagagcg tggtgcagca gtatctggat   900
gtcgtgggct accccttcat gcccccttac tggggcctgg gattccaccct gtgcagatgg   960 ggctactcca gcaccgccat caccagacag gtggtgaaaa acatgaccag agcccacttc   1020
ccactggatg tgcagtggaa cgacctggac tacatggaca gcagacggga cttcaccttc   1080
aacaaggacg gcttccggga cttcccgcc atggtgcagg aactgcatca gggcggcaga   1140
cggtacatga tgatcgtgga tcccgccatc agctcctctg ccctgccgg ctcttacaga   1200 ccctacgacg agggcctgcg gagaggcgtg ttcatcacca acgagacagg ccagcccctg   1260
atcggcaaag tgtggcctgg cagcacagcc ttccccgact caccaatcc taccgccctg   1320 gcttggtggg aggacatggt ggccgagttc acgaccagg tgcccttcga cggcatgtgg   1380
atcgacatga acgagcccag caacttcatc cggggcagcg aggatggctg ccccaacaac   1440
gaactggaaa atccccccta cgtgcccggc gtcgtgggcg aacactgca ggccgctaca   1500 atctgtgcca gcagccacca gtttctgagc acccactaca acctgcacaa cctgtacggc   1560
ctgaccgagg ccattgccag ccaccgcgct ctcgtgaaag ccagaggcac acggcccttc   1620
gtgatcagca gaagccctt tgccggccac ggcagatacg ccggacattg gactggcgac   1680
gtgtggtcct cttgggagca gctggcctct agcgtgcccg agatcctgca gttcaatctg   1740
```

```
ctgggcgtgc cactcgtggg cgccgatgtg tgtggcttcc tgggcaacac ctccgaggaa    1800
ctgtgtgtgc ggtggacaca gctgggcgcc ttctacccct tcatgagaaa ccacaacagc    1860
ctgctgagcc tgccccagga accctacagc tttagcgagc tgcacagca ggccatgcgg     1920 aaggccctga cactgagata cgctctgctg ccccacctgt acaccctgtt tcaccaggcc    1980
catgtggccg gcgagacagt ggccagacct ctgtttctgg aattccccaa ggacagcagc    2040
acctggaccg tggaccatca gctgctgtgg ggagaggctc tgctgattac cccagtgctg    2100
caggcaggca aggccgaagt gaccggctac tttcccctgg gcacttggta cgacctgcag    2160
accgtgcctg tggaagccct gggatctctg cctccacctc tgccgctcc tagagagcct     2220 gccattcact ctgagggcca gtgggtcaca ctgcctgccc cctggatac catcaacgtg      2280 cacctgaggg ccggctacat cataccactg cagggacctg gcctgaccac caccgagtct    2340
agacagcagc caatggccct ggccgtggcc ctgaccaaag gcggagaagc taggggcgag    2400
ctgttctggg acgatggcga gagcctggaa gtgctggaaa gaggcgccta tacccaagtg    2460
atcttcctgg cccggaacaa caccatcgtg aacgagctgg tgcgcgtgac ctctgaaggc    2520
gctggactgc agctgcagaa agtgaccgtg ctgggagtgg ccacagcccc tcagcaggtg    2580
ctgtctaatg gcgtgcccgt gtccaacttc acctacagcc ccgacaccaa ggtgctggac    2640
atctgcgtgt cactgctgat gggagagcag tttctggtgt cctggtgctg a             2691

<210> SEQ ID NO 47
<211> LENGTH: 2691
<212> TYPE: DNA
<213> ORGANISM: artificial
<220> FEATURE:
<223> OTHER INFORMATION: sp7+hGAAco2-delta-47

<400> SEQUENCE: 47
atggcctttc tgtggctgct gagctgttgg gccctgctgg caccaccttt cggcccaaga    60
gctgtgccta cccaatgcga cgtgccaccc aactcccgat cgactgcgc gccagataag     120 gctattaccc aagagcagtg tgaagccaga ggttgctgct acatcccagc gaagcaagga    180
ttgcaaggcg cccaaatggg acaaccttgg tgtttcttcc cccttcgta cccatcatat     240 aaactcgaaa acctgtcctc ttcggaaatg ggttatactg ccaccctcac cagaactact    300
cctactttct cccgaaagac atcttgacc ttgaggctgg acgtgatgat ggagactgaa      360
aaccggctgc atttcactat caaagatcct gccaatcggc gatacgaggt ccctctggaa    420 accccctcacg tgcactcacg ggctccttct ccgctttact ccgtcgaatt ctctgaggaa    480
cccttcggag tgatcgttag acgccagctg gatggtagag tgctgttgaa cactactgtg    540
gcccactttt cttcgctga ccagtttctg caactgtcca cttccctgcc atcccagtac     600
attactggac tcgccgaaca cctgtcgcca ctgatgctct cgacctcttg gactagaatc    660
actttgtgga acagagactt ggcccctact ccgggagcaa atctgtacgg aagccacccct   720 ttttacctgg cgctcgaaga tgcggatcc gctcacggag tgttcctgct gaatagcaac     780
gcaatggacg tggtgctgca accttcccct gcactcagtt ggagaagtac cgggggtatt    840
ctggacgtgt acatcttcct cggaccagaa cccaagagcg tggtgcagca atatctggac    900
gtggtcggat ccctttttat gcctccttac tggggactgg gattccacct tgccgttgg     960 ggctactcat ccaccgccat taccagacag tggtggaga atatgaccag agcccacttc    1020
cctctcgacg tgcagtggaa cgatctggac tatatggact cccggagaga tttcaccttc    1080
aacaaggacg ggttccgcga ttttccgcg atggttcaag agctccacca gggtggtcga    1140
```

| | |
|---|---|
| agatatatga tgatcgtcga cccagccatt tcgagcagcg acccgctgg atcttataga | 1200 |
| ccttacgacg aaggccttag gagaggagtg ttcatcacaa acgagactgg acagcctttg | 1260 |
| atcggtaaag tgtggcctgg atcaaccgcc tttcctgact ttaccaatcc cactgccttg | 1320 |
| gcttggtggg aggacatggt ggccgaattc cacgaccaag tcccctttga tggaatgtgg | 1380 |
| atcgatatga acgaaccaag caattttatc agaggttccg aagacggttg ccccaacaac | 1440 |
| gaactggaaa accctcctta tgtgcccgga gtcgtgggcg aacattaca ggccgcgact | 1500 |
| atttgcgcca gcagccacca attcctgtcc actcactaca acctccacaa cctttatgga | 1560 |
| ttaaccgaag ctattgcaag tcacagggct ctggtgaagg ctagagggac taggcccttt | 1620 |
| gtgatctccc gatccacctt tgccggacac gggagatacg ccggtcactg gactggtgac | 1680 |
| gtgtggagct catgggaaca actggcctcc tccgtgccgg aaatcttaca gttcaacctt | 1740 |
| ctgggtgtcc ctcttgtcgg agcagacgtg tgtgggtttc ttggtaacac ctccgaggaa | 1800 |
| ctgtgtgtgc gctggactca actgggtgca ttctacccat tcatgagaaa ccacaactcc | 1860 |
| ttgctgtccc tgccacaaga gccctactcg ttcagcgagc ctgcacaaca ggctatgcgg | 1920 |
| aaggcactga ccctgagata cgccctgctt ccacacttat acactctctt ccatcaagcg | 1980 |
| catgtggcag agaaaccgt tgcaaggcct cttttccttg aattccccaa ggattcctcg | 2040 |
| acttggacgg tggatcatca gctgctgtgg ggagaagctc tgctgattac tccagtgttg | 2100 |
| caagccggaa aagctgaggt gaccggatac tttccgctgg aacctggta cgacctccag | 2160 |
| actgtccctg ttgaagccct tggatcactg cctccgcctc cggcagctcc acgcgaacca | 2220 |
| gctatacatt ccgagggaca gtgggttaca ttaccagctc ctctggacac aatcaacgtc | 2280 |
| cacttaagag ctggctacat tatccctctg caaggaccag gactgactac gaccgagagc | 2340 |
| agacagcagc caatggcact ggctgtggct ctgaccaagg gaggggaagc tagaggagaa | 2400 |
| ctcttctggg atgatgggga gtcccttgaa gtgctggaaa gaggcgctta cactcaagtc | 2460 |
| attttccttg cacggaacaa caccattgtg aacgaattgg tgcgagtgac cagcgaagga | 2520 |
| gctggacttc aactgcagaa ggtcactgtg ctcggagtgg ctaccgctcc tcagcaagtg | 2580 |
| ctgtcgaatg gagtccccgt gtcaaacttt acctactccc ctgacactaa ggtgctcgac | 2640 |
| atttgcgtgt ccctcctgat gggagagcag ttccttgtgt cctggtgttg a | 2691 |

<210> SEQ ID NO 48
<211> LENGTH: 2652
<212> TYPE: DNA
<213> ORGANISM: artificial
<220> FEATURE:
<223> OTHER INFORMATION: hGAAco1-delta-42

<400> SEQUENCE: 48

| | |
|---|---|
| gcccaccccg gcagacctag agctgtgcct acccagtgtg acgtgccccc caacagcaga | 60 |
| ttcgactgcg cccctgacaa ggccatcacc caggaacagt gcgaggccag aggctgctgc | 120 |
| tacatccctg ccaagcaggg actgcagggc gctcagatgg gacagccctg gtgcttcttc | 180 |
| ccaccctcct accccagcta caagctggaa aacctgagca gcagcgagat gggctacacc | 240 |
| gccaccctga ccagaaccac ccccacattc ttccaaagg acatcctgac cctgcggctg | 300 |
| gacgtgatga tggaaaccga gaaccggctg cacttcacca tcaaggaccc cgccaatcgg | 360 |
| agatacgagg tgcccctgga aaccccccac gtgcactcta gagcccccag ccctctgtac | 420 |
| agcgtggaat tcagcgagga accttcggc gtgatcgtgc ggagacagct ggatggcaga | 480 |

```
gtgctgctga acaccaccgt ggcccctctg ttcttcgccg accagttcct gcagctgagc    540
accagcctgc ccagccagta catcacagga ctggccgagc acctgagccc cctgatgctg    600
agcacatcct ggacccggat caccctgtgg aacagggatc tggcccctac ccctggcgcc    660
aatctgtacg gcagccaccc tttctacctg gccctggaag atggcggatc tgcccacgga    720
gtgtttctgc tgaactccaa cgccatggac gtggtgctgc agcctagccc tgccctgtct    780
tggagaagca caggcggcat cctggatgtg tacatctttc tgggccccga gcccaagagc    840
gtggtgcagc agtatctgga tgtcgtgggc taccccttca tgccccctta ctggggcctg    900
ggattccacc tgtgcagatg gggctactcc agcaccgcca tcaccagaca ggtggtggaa    960
acatgaccac gagcccactt cccactggat gtgcagtgga cgacctggac tacatggac     1020 agcagacggg acttcacctt caacaaggac ggcttccggg acttccccgc catggtgcag    1080
gaactgcatc agggcggcag acggtacatg atgatcgtgg atcccgccat cagctcctct    1140
ggccctgccg gctcttacag accctacgac gagggcctgc ggagaggcgt gttcatcacc    1200
aacgagacag gccagcccct gatcggcaaa gtgtggcctg cagcacagc cttccccgac     1260 ttcaccaatc ctaccgccct ggcttggtgg aggacatgg tggccgagtt ccacgaccag     1320
gtgcccttcg acggcatgtg gatcgacatg aacgagccca gcaacttcat ccggggcagc    1380
gaggatggct gccccaacaa cgaactggaa atccccctt acgtgcccgg cgtcgtgggc     1440
ggaacactgc aggccgctac aatctgtgcc agcagccacc agtttctgag cacccactac    1500
aacctgcaca acctgtacgg cctgaccgag gccattgcca gccaccgcgc tctcgtgaaa    1560
gccagaggca cacggcccctt cgtgatcagc agaagcacct tgccggcca cggcagatac    1620 gccggacatt ggactggcga cgtgtggtcc tcttgggagc agctggcctc tagcgtgccc    1680
gagatcctgc agttcaatct gctgggcgtg ccactcgtgg cgccgatgt gtgtggcttc    1740 ctgggcaaca cctccgagga actgtgtgtg cggtggacac agctgggcgc cttctaccct    1800
ttcatgagaa accacaacag cctgctgagc ctgccccagg aaccctacag ctttagcgag    1860
cctgcacagc aggccatgcg gaaggccctg acactgagat acgctctgct gccccacctg    1920
tacaccctgt ttcaccaggc ccatgtggcc ggcgagacag tggccagacc tctgtttctg    1980
gaattcccca aggacagcag cacctggacc gtggaccatc agctgctgtg gggagaggct    2040
ctgctgatta ccccagtgct gcaggcaggc aaggccgaag tgaccggcta ctttcccctg    2100
ggcacttggt acgacctgca gaccgtgcct gtggaagccc tgggatctct gcctccacct    2160
cctgccgctc ctagagagcc tgccattcac tctgagggcc agtgggtcac actgcctgcc    2220
cccctggata ccatcaacgt gcacctgagg gccggctaca tcataccact gcagggacct    2280
ggcctgacca ccaccgagtc tagacagcag ccaatggccc tggccgtggc cctgaccaaa    2340
ggcggagaag ctaggggcga gctgttctgg gacgatggcg agagcctgga agtgctggaa    2400
agaggcgcct atacccaagt gatcttcctg gcccggaaca acaccatcgt gaacgagctg    2460
gtgcgcgtga cctctgaagg cgctggactg cagctgcaga aagtgaccgt gctgggagtg    2520
gccacagccc ctcagcaggt gctgtctaat ggcgtgcccg tgtccaactt cacctacagc    2580
cccgacacca aggtgctgga catctgcgtg tcactgctga tgggagagca gtttctggtg    2640
tcctggtgct ga                                                         2652

<210> SEQ ID NO 49
<211> LENGTH: 2652
<212> TYPE: DNA
<213> ORGANISM: artificial
```

<220> FEATURE:
<223> OTHER INFORMATION: hGAAco2-delta-42

<400> SEQUENCE: 49

```
gcccatcctg gtagaccaag agctgtgcct acccaatgcg acgtgccacc caactcccga      60
ttcgactgcg cgccagataa ggctattacc caagagcagt gtgaagccag aggttgctgc     120
tacatcccag cgaagcaagg attgcaaggc gcccaaatgg acaaccttg gtgtttcttc      180
cccccttcgt acccatcata taaactcgaa aacctgtcct cttcggaaat gggttatact     240
gccacactca ccagaactac tcctactttc ttcccgaaag acatcttgac cttgaggctg     300
gacgtgatga tggagactga aaaccggctg catttcacta tcaaagatcc tgccaatcgg     360
cgatacgagg tccctctgga aacccctcac gtgcactcac gggctccttc tccgctttac     420
tccgtcgaat tctctgagga acccttcgga gtgatcgtta cgccagct ggatggtaga       480
gtgctgttga acactactgt ggccccactt ttcttcgctg accagtttct gcaactgtcc     540
acttccctgc catcccagta cattactgga ctcgccgaac acctgtcgcc actgatgctc     600
tcgacctctt ggactagaat cactttgtgg aacagagact tggcccctac tccgggagca     660
aatctgtacg gaagccaccc ttttacctg gcgctcgaag atggcggatc cgctcacgga     720
gtgttcctgc tgaatagcaa cgcaatggac gtggtgctgc aaccttcccc tgcactcagt     780
tggagaagta ccgggggtat tctggacgtg tacatcttcc tcggaccaga acccaagagc     840
gtggtgcagc aatatctgga cgtggtcgga taccctttta tgcctcctta ctggggactg     900
ggattccacc tttgccgttg gggctactca tccaccgcca ttaccagaca ggtggtggag     960
aatatgacca gagcccactt ccctctcgac gtgcagtgga cgatctgga ctatatggac    1020
tcccggagag atttcacctt caacaaggac gggttccgcg attttcccgc gatggttcaa    1080
gagctccacc agggtggtcg aagatatatg atgatcgtcg acccagccat ttcgagcagc    1140
ggacccgctg gatcttatag accttacgac gaaggcctta ggagaggagt gttcatcaca    1200
aacgagactg gacagccttt gatcggtaaa gtgtggcctg gatcaaccgc ctttcctgac    1260
tttaccaatc ccactgcctt ggcttggtgg gaggacatgg tggccgaatt ccacgaccaa    1320
gtccccttg atggaatgtg gatcgatatg aacgaaccaa gcaattttat cagaggttcc    1380
gaagacggtt gccccaacaa cgaactggaa accctcctt atgtgcccgg agtcgtgggc    1440
ggaacattac aggccgcgac tatttgcgcc agcagccacc aattcctgtc cactcactac    1500
aacctccaca acctttatgg attaaccgaa gctattgcaa gtcacagggc tctggtgaag    1560
gctagaggga ctaggccctt tgtgatctcc cgatccacct tgccggaca cgggagatac     1620
gccggtcact ggactggtga cgtgtggagc tcatgggaac aactggcctc ctccgtgccg    1680
gaaatcttac agttcaacct tctgggtgtc cctcttgtcg gagcagacgt gtgtgggttt    1740
cttggtaaca cctccgagga actgtgtgtg cgctggactc aactgggtgc attctaccca    1800
ttcatgagaa accacaactc cttgctgtcc ctgccacaag agccctactc gttcagcgag    1860
cctgcacaac aggctatgcg gaaggcactg accctgagat acgccctgct tccacactta    1920
tacactctct tccatcaagc gcatgtggca ggagaaaccg ttgcaaggcc tcttttcctt    1980
gaattcccca aggattcctc gacttggacg gtggatcatc agctgctgtg gggagaagct    2040
ctgctgatta ctccagtgtt gcaagccgga aaagctgagg tgaccggata ctttccgctg    2100
ggaacctggt acgacctcca gactgtccct gttgaagccc ttggatcact gcctccgcct    2160
ccggcagctc cacgcgaacc agctatacat tccgagggac agtgggttac attaccagct    2220
```

```
cctctggaca caatcaacgt ccacttaaga gctggctaca ttatccctct gcaaggacca    2280
ggactgacta cgaccgagag cagacagcag ccaatggcac tggctgtggc tctgaccaag    2340 ggagggaag  ctagaggaga actcttctgg gatgatgggg agtcccttga agtgctggaa    2400
agaggcgctt acactcaagt catttcctt  gcacggaaca acaccattgt gaacgaattg    2460
gtgcgagtga ccagcgaagg agctggactt caactgcaga aggtcactgt gctcggagtg    2520
gctaccgctc ctcagcaagt gctgtcgaat ggagtccccg tgtcaaactt tacctactcc    2580
cctgacacta aggtgctcga catttgcgtg tccctcctga tgggagagca gttccttgtg    2640
tcctggtgtt ga                                                        2652
```

```
<210> SEQ ID NO 50
<211> LENGTH: 2649
<212> TYPE: DNA
<213> ORGANISM: artificial
<220> FEATURE:
<223> OTHER INFORMATION: hGAAco1-delta-43

<400> SEQUENCE: 50
caccccggca gacctagagc tgtgcctacc cagtgtgacg tgcccccaa  cagcagattc     60 gactgcgccc ctgacaaggc catcacccag gaacagtgcg aggccagagg ctgctgctac    120
atccctgcca agcagggact gcagggcgct cagatgggac agccctggtg cttcttccca    180
ccctcctacc ccagctacaa gctggaaaac ctgagcagca gcgagatggg ctacaccgcc    240
accctgacca gaaccacccc cacattcttc ccaaaggaca tcctgacccct gcggctggac    300 gtgatgatgg aaaccgagaa ccggctgcac ttcaccatca aggaccccgc caatcggaga    360
tacgaggtgc ccctggaaac cccccacgtg cactctagag cccccagccc tctgtacagc    420
gtggaattca gcgaggaacc cttcggcgtg atcgtgcgga cagctggga  tggcagagtg    480 ctgctgaaca ccaccgtggc ccctctgttc ttcgccgacc agttcctgca gctgagcacc    540
agcctgccca gccagtacat cacaggactg gccgagcacc tgagccccct gatgctgagc    600
acatcctgga ccccggatca cctgtggaac agggatctgg cccctacccc tggcgccaat    660
ctgtacggca gcaccccttt ctacctggcc ctggaagatg gcggatctgc ccacggagtg    720
tttctgctga actccaacgc catggacgtg gtgctgcagc ctagccctgc cctgtcttgg    780
agaagcacag gcggcatcct ggatgtgtac atctttctgg gccccgagcc caagagcgtg    840
gtgcagcagt atctggatgt cgtgggctac cccttcatgc cccttactg   gggcctggga    900 ttccacctgt gcagatgggg ctactccagc accgccatca ccagacaggt ggtgaaaac    960 atgaccagag cccacttccc actggatgtg cagtggaacg acctggacta catggacagc    1020
agacgggact tcaccttcaa caaggacggc ttccggagct tccccgccat ggtgcaggaa    1080
ctgcatcagg gcggcagacg gtacatgatg atcgtggatc cgccatcag  ctcctctggc    1140 cctgccggct cttacagacc ctacgacgag ggcctgcgga gggcgtgtt  catcaccaac    1200 gagacaggcc agccctgat  cggcaaagtg tggcctggca gcagagcct  ccccgacttc    1260 accaatccta ccgccctggc ttggtgggag gacatggtgg ccgagttcca cgaccaggtg    1320
cccttcgacg gcatgtggat cgacatgaac gagcccagca acttcatcccg gggcagcgag    1380 gatggctgcc ccaacaacga actggaaaat ccccccttacg tgcccggcgt cgtgggcgga    1440
acactgcagg ccgctacaat ctgtgccagc agccaccagt ttctgagcac ccactacaac    1500
ctgcacaacc tgtacggcct gaccgaggcc attgccagcc accgcgctct cgtgaaagcc    1560
agaggcacac ggcccttcgt gatcagcaga agcacctttg ccggccacgg cagatacgcc    1620
```

```
ggacattgga ctggcgacgt gtggtcctct tgggagcagc tggcctctag cgtgcccgag    1680
atcctgcagt tcaatctgct gggcgtgcca ctcgtgggcg ccgatgtgtg tggcttcctg    1740
ggcaacacct ccgaggaact gtgtgtgcgg tggacacagc tgggcgcctt ctacccttc     1800
atgagaaacc acaacagcct gctgagcctg ccccaggaac cctacagctt agcgagcct     1860
gcacagcagg ccatgcggaa ggccctgaca ctgagatacg ctctgctgcc ccacctgtac    1920
accctgtttc accaggccca tgtggccggc gagacagtgg ccagacctct gtttctggaa    1980
ttccccaagg acagcagcac ctggaccgtg gaccatcagc tgctgtgggg agaggctctg    2040
ctgattaccc cagtgctgca ggcaggcaag gccgaagtga ccggctactt tcccctgggc    2100
acttggtacg acctgcagac cgtgcctgtg aagccctgg  atctctgcc tccacctcct    2160
gccgctccta gagagcctgc cattcactct gagggccagt gggtcacact gcctgccccc    2220
ctggatacca tcaacgtgca cctgagggcc ggctacatca taccactgca gggacctggc    2280
ctgaccacca ccgagtctag acagcagcca atggccctgg ccgtggccct gaccaaaggc    2340
ggagaagcta ggggcgagct gttctgggac gatggcgaga gcctggaagt gctggaaaga    2400
ggcgcctata cccaagtgat cttcctggcc cggaacaaca ccatcgtgaa cgagctggtg    2460
cgcgtgacct ctgaaggcgc tggactgcag ctgcagaaag tgaccgtgct gggagtggcc    2520
acagccctc agcaggtgct gtctaatggc gtgcccgtgt ccaacttcac ctacagcccc    2580
gacaccaagg tgctggacat ctgcgtgtca ctgctgatgg gagagcagtt tctggtgtcc    2640
tggtgctga                                                           2649
```

<210> SEQ ID NO 51
<211> LENGTH: 2649
<212> TYPE: DNA
<213> ORGANISM: artificial
<220> FEATURE:
<223> OTHER INFORMATION: hGAAco2-delta-43

<400> SEQUENCE: 51

```
catcctggta gaccaagagc tgtgcctacc caatgcgacg tgccacccaa ctcccgattc      60
gactgcgcgc cagataaggc tattacccaa gagcagtgtg aagccagagg ttgctgctac    120
atcccagcga agcaaggatt gcaaggcgcc caaatgggac aaccttggtg tttcttcccc    180
ccttcgtacc catcatataa actcgaaaac ctgtcctctt cggaaatggg ttatactgcc    240
accctcacca gaactactcc tactttcttc ccgaaagaca tcttgacctt gaggctggac    300
gtgatgatgg agactgaaaa ccggctgcat tcactatca  aagatcctgc caatcggcga    360
tacgaggtcc ctctggaaac ccctcacgtg cactcacggg ctccttctcc gctttactcc    420
gtcgaattct ctgaggaacc cttcggagtg atcgttagac gccagctgga tggtagagtg    480
ctgttgaaca ctactgtggc cccacttttc ttcgctgacc agtttctgca actgtccact    540
tccctgccat cccagtacat tactggactc gccgaacacc tgtcgccact gatgctctcg    600
acctcttgga ctagaatcac tttgtggaac agagacttgg cccctactcc gggagcaaat    660
ctgtacggaa gccaccccttt ttacctggcg ctcgaagatg gcggatccgc tcacggagtg    720
ttcctgctga atagcaacgc aatggacgtg gtgctgcaac ttcccctgc  actcagttgg    780
agaagtaccg ggggtattct ggacgtgtac atcttcctcg gaccagaacc caagagcgtg    840
gtgcagcaat atctggacgt ggtcggatac ccttttatgc ctccttactg gggactggga    900
ttccacctttt gccgttgggg ctactcatcc accgccatta ccagacaggt ggtggagaat    960
```

```
atgaccagag cccacttccc tctcgacgtg cagtggaacg atctggacta tatggactcc    1020
cggagagatt tcaccttcaa caaggacggg ttccgcgatt ttcccgcgat ggttcaagag    1080
ctccaccagg gtggtcgaag atatatgatg atcgtcgacc cagccatttc gagcagcgga    1140
cccgctggat cttatagacc ttacgacgaa ggccttagga gaggagtgtt catcacaaac    1200
gagactggac agcctttgat cggtaaagtg tggcctggat caaccgcctt tcctgacttt    1260
accaatccca ctgccttggc ttggtgggag gacatggtgg ccgaattcca cgaccaagtc    1320 cccttttgatg aatgtggat cgatatgaac gaaccaagca attttatcag aggttccgaa    1380
gacggttgcc ccaacaacga actggaaaac cctccttatg tgcccggagt cgtgggcgga    1440
acattacagg ccgcgactat ttgcgccagc agccaccaat tcctgtccac tcactacaac    1500
ctccacaacc tttatggatt aaccgaagct attgcaagtc acagggctct ggtgaaggct    1560
agagggacta ggccctttgt gatctcccga tccacctttg ccggacacgg agatacgcc    1620 ggtcactgga ctggtgacgt gtggagctca tgggaacaac tggcctcctc cgtgccggaa    1680
atcttacagt tcaaccttct gggtgtccct cttgtcggag cagacgtgtg tgggtttctt    1740
ggtaacacct ccgaggaact gtgtgtgcgc tggactcaac tgggtgcatt ctacccattc    1800
atgagaaacc acaactcctt gctgtccctg ccacaagagc cctactcgtt cagcgagcct    1860
gcacaacagg ctatgcggaa ggcactgacc ctgagatacg ccctgcttcc acacttatac    1920
actctcttcc atcaagcgca tgtggcagga gaaaccgttg caaggcctct tttccttgaa    1980
ttccccaagg attcctcgac ttggacggtg gatcatcagc tgctgtgggg agaagctctg    2040
ctgattactc cagtgttgca agccggaaaa gctgaggtga ccggatactt ccgctggga    2100 acctggtacg acctccagac tgtccctgtt gaagcccttg gatcactgcc tccgcctccg    2160
gcagctccac gcgaaccagc tatacattcc gagggacagt gggttacatt accagctcct    2220
ctggacacaa tcaacgtcca cttaagagct ggctacatta tccctctgca aggaccagga    2280
ctgactacga ccgagagcag acagcagcca atggcactgg ctgtggctct gaccaaggga    2340
ggggaagcta gaggagaact cttctgggat gatggggagt cccttgaagt gctggaaaga    2400
ggcgcttaca ctcaagtcat tttccttgca cggaacaaca ccattgtgaa cgaattggtg    2460
cgagtgacca gcgaaggagc tggacttcaa ctgcagaagg tcactgtgct cggagtggct    2520
accgctcctc agcaagtgct gtcgaatgga gtccccgtgt caaactttac ctactcccct    2580
gacactaagg tgctcgacat ttgcgtgtcc ctcctgatgg gagagcagtt ccttgtgtcc    2640
tggtgttga                                                              2649
```

<210> SEQ ID NO 52
<211> LENGTH: 2637
<212> TYPE: DNA
<213> ORGANISM: artificial
<220> FEATURE:
<223> OTHER INFORMATION: hGAAco1-delta-47

<400> SEQUENCE: 52

```
cctagagctg tgcctaccca gtgtgacgtg cccccccaaca gcagattcga ctgcgcccct    60
gacaaggcca tcacccagga acagtgcgag gccagaggct gctgctacat ccctgccaag    120
cagggactgc agggcgctca gatgggacag ccctggtgct tcttcccacc ctcctacccc    180
agctacaagc tggaaaacct gagcagcagc gagatgggct acaccgccac cctgaccaga    240
accaccccca cattcttccc aaaggacatc ctgaccctgc ggctggacgt gatgatggaa    300
accgagaacc ggctgcactt caccatcaag gaccccgcca tcggagata cgaggtgccc    360
```

```
ctggaaaccc cccacgtgca ctctagagcc cccagccctc tgtacagcgt ggaattcagc    420
gaggaaccct tcggcgtgat cgtgcggaga cagctggatg cagagtgct gctgaacacc     480
accgtggccc ctctgttctt cgccgaccag ttcctgcagc tgagcaccag cctgcccagc    540
cagtacatca caggactggc cgagcacctg agcccctga tgctgagcac atcctggacc     600
cggatcaccc tgtggaacag ggatctggcc cctaccctg gcgccaatct gtacggcagc     660
caccctttct acctggccct ggaagatggc ggatctgccc acggagtgtt tctgctgaac    720
tccaacgcca tggacgtggt gctgcagcct agccctgccc tgtcttggag aagcacaggc    780
ggcatcctgg atgtgtacat ctttctgggc cccgagccca gagcgtggt gcagcagtat     840
ctggatgtcg tgggctaccc cttcatgccc ccttactggg gcctgggatt ccacctgtgc    900
agatggggct actccagcac cgccatcacc agacaggtgg tgaaaaacat gaccagagcc    960
cacttcccac tggatgtgca gtggaacgac ctggactaca tggacagcag acgggacttc   1020
accttcaaca aggacggctt ccgggacttc ccgccatgg tgcaggaact gcatcagggc    1080
ggcagacggt acatgatgat cgtggatccc gccatcagct cctctggccc tgccggctct   1140
tacagaccct acgacgaggg cctgcggaga ggcgtgttca tcaccaacga cacaggccag   1200
cccctgatcg gcaaagtgtg gcctggcagc acagccttcc ccgacttcac caatcctacc   1260
gccctggctt ggtgggagga catggtggcc gagttccacg accaggtgcc cttcgacggc   1320
atgtggatcg acatgaacga gcccagcaac ttcatccggg gcagcgagga tggctgcccc   1380
aacaacgaac tggaaaatcc cccttacgtg cccggcgtcg tgggcggaac actgcaggcc   1440
gctacaatct gtgccagcag ccaccagttt ctgagcaccc actacaacct gcacaacctg   1500
tacggcctga ccgaggccat tgccagccac cgcgctctcg tgaaagccag aggcacacgg   1560
cccttcgtga tcagcagaag cacctttgcc ggccacggca gatacgccgg acattggact   1620
ggcgacgtgt ggtcctcttg ggagcagctg gcctctagcg tgcccgagat cctgcagttc   1680
aatctgctgg gcgtgccact cgtgggcgcc gatgtgtgtg gcttcctggg caacacctcc   1740
gaggaactgt gtgtgcggtg gacacagctg ggcgccttct accctttcat gagaaaccac   1800
aacagcctgc tgagcctgcc ccaggaaccc tacagcttta gcgagcctgc acagcaggcc   1860
atgcggaagg ccctgacact gagatacgct ctgctgcccc acctgtacac cctgtttcac   1920
caggcccatg tggccggcga cagtggcc agacctctgt ttctggaatt ccccaaggac     1980
agcagcacct ggaccgtgga ccatcagctg ctgtggggag aggctctgct gattaccccca   2040
gtgctgcagg caggcaaggc cgaagtgacc ggctactttc ccctgggcac ttggtacgac   2100
ctgcagaccg tgcctgtgga agccctggga tctctgcctc cacctcctgc cgctcctaga   2160
gagcctgcca ttcactctga gggccagtgg gtcacactgc ctgcccccct ggataccatc   2220
aacgtgcacc tgagggccgg ctacatcata ccactgcagg gacctggcct gaccaccacc   2280
gagtctagac agcagccaat ggccctggcc gtggccctga ccaaaggcgg agaagctagg   2340
ggcgagctgt tctgggacga tggcgagagc ctggaagtgc tggaaagagg cgcctatacc   2400
caagtgatct tcctggcccg gaacaacacc atcgtgaacg agctggtgcg cgtgaccctct   2460
gaaggcgctg gactgcagct gcagaaagtg accgtgctgg gagtggccac agcccctcag   2520
caggtgctgt ctaatggcgt gcccgtgtcc aacttcacct acagccccga caccaaggtg   2580
ctggacatct gcgtgtcact gctgatggga gagcagtttc tggtgtcctg gtgctga       2637
```

<210> SEQ ID NO 53

<211> LENGTH: 2637
<212> TYPE: DNA
<213> ORGANISM: artificial
<220> FEATURE:
<223> OTHER INFORMATION: hGAAco2-delta-47

<400> SEQUENCE: 53

| | | | | | |
|---|---|---|---|---|---|
| ccaagagctg | tgcctaccca | atgcgacgtg | ccacccaact | cccgattcga | ctgcgcgcca | 60 |
| gataaggcta | ttacccaaga | gcagtgtgaa | gccagaggtt | gctgctacat | cccagcgaag | 120 |
| caaggattgc | aaggcgccca | atgggacaa | ccttggtgtt | tcttcccccc | ttcgtaccca | 180 |
| tcatataaac | tcgaaaacct | gtcctcttcg | gaaatgggtt | atactgccac | cctcaccaga | 240 |
| actactccta | ctttcttccc | gaaagacatc | ttgaccttga | ggctggacgt | gatgatggag | 300 |
| actgaaaacc | ggctgcattt | cactatcaaa | gatcctgcca | atcggcgata | cgaggtccct | 360 |
| ctggaaaccc | ctcacgtgca | ctcacgggct | ccttctccgc | tttactccgt | cgaattctct | 420 |
| gaggaaccct | tcggagtgat | cgttagacgc | cagctggatg | gtagagtgct | gttgaacact | 480 |
| actgtggccc | cactttctt | cgctgaccag | tttctgcaac | tgtccacttc | cctgccatcc | 540 |
| cagtacatta | ctggactcgc | cgaacacctg | tcgccactga | tgctctcgac | ctcttggact | 600 |
| agaatcactt | tgtggaacag | agacttggcc | cctactccgg | gagcaaatct | gtacggaagc | 660 |
| cacccttttt | acctggcgct | cgaagatggc | ggatccgctc | acggagtgtt | cctgctgaat | 720 |
| agcaacgcaa | tggacgtggt | gctgcaacct | tcccctgcac | tcagttggag | aagtaccggg | 780 |
| ggtattctgg | acgtgtacat | cttcctcgga | ccagaaccca | agagcgtggt | gcagcaatat | 840 |
| ctggacgtgg | tcggataccc | ttttatgcct | ccttactggg | gactgggatt | ccacctttgc | 900 |
| cgttggggct | actcatccac | cgccattacc | agacaggtgg | tggagaatat | gaccagagcc | 960 |
| cacttccctc | tcgacgtgca | gtggaacgat | ctggactata | tggactcccg | gagagatttc | 1020 |
| accttcaaca | aggacgggtt | ccgcgatttt | cccgcgatgg | ttcaagagct | ccaccagggt | 1080 |
| ggtcgaagat | atatgatgat | cgtcgaccca | gccatttcga | gcagcggacc | cgctggatct | 1140 |
| tatagacctt | acgacgaagg | ccttaggaga | ggagtgttca | tcacaaacga | gactggacag | 1200 |
| cctttgatcg | gtaaagtgtg | gcctggatca | accgcctttc | ctgactttac | caatcccact | 1260 |
| gccttggctt | ggtgggagga | catggtggcc | gaattccacg | accaagtccc | ctttgatgga | 1320 |
| atgtggatcg | atatgaacga | accaagcaat | tttatcagag | gttccgaaga | cggttgcccc | 1380 |
| aacaacgaac | tggaaaaccc | tccttatgtg | cccggagtcg | tgggcggaac | attacaggcc | 1440 |
| gcgactattt | gcgccagcag | ccaccaattc | ctgtccactc | actacaacct | ccacaacctt | 1500 |
| tatggattaa | ccgaagctat | tgcaagtcac | agggctctgg | tgaaggctag | agggactagg | 1560 |
| ccctttgtga | tctcccgatc | cacctttgcc | ggacacggga | gatacgccgg | tcactgact | 1620 |
| ggtgacgtgt | ggagctcatg | ggaacaactg | gcctcctccg | tgccggaaat | cttacagttc | 1680 |
| aaccttctgg | gtgtccctct | tgtcggagca | gacgtgtgtg | ggtttcttgg | taacacctcc | 1740 |
| gaggaactgt | gtgtgcgctg | gactcaactg | ggtgcattct | acccattcat | gagaaaccac | 1800 |
| aactccttgc | tgtccctgcc | acaagagccc | tactcgttca | gcgagcctgc | acaacaggct | 1860 |
| atgcggaagg | cactgaccct | gagatacgcc | ctgcttccac | acttatacac | tctcttccat | 1920 |
| caagcgcatg | tggcaggaga | aaccgttgca | aggcctcttt | tccttgaatt | ccccaaggat | 1980 |
| tcctcgactt | ggacggtgga | tcatcagctg | ctgtggggag | aagctctgct | gattactcca | 2040 |
| gtgttgcaag | ccggaaaagc | tgaggtgacc | ggatactttc | cgctgggaac | ctggtacgac | 2100 |
| ctccagactg | tccctgttga | agcccttgga | tcactgcctc | cgcctccggc | agctccacgc | 2160 |

```
gaaccagcta tacattccga gggacagtgg gttacattac cagctcctct ggacacaatc    2220
aacgtccact taagagctgg ctacattatc cctctgcaag gaccaggact gactacgacc    2280
gagagcagac agcagccaat ggcactggct gtggctctga ccaagggagg ggaagctaga    2340
ggagaactct tctgggatga tggggagtcc cttgaagtgc tggaaagagg cgcttacact    2400
caagtcattt tccttgcacg gaacaacacc attgtgaacg aattggtgcg agtgaccagc    2460
gaaggagctg gacttcaact gcagaaggtc actgtgctcg gagtggctac cgctcctcag    2520
caagtgctgt cgaatggagt ccccgtgtca aactttacct actcccctga cactaaggtg    2580
ctcgacattt gcgtgtccct cctgatggga gagcagttcc ttgtgtcctg gtgttga       2637
```

ACID-ALPHA GLUCOSIDASE VARIANTS AND USES THEREOF

CROSS-REFERENCE TO RELATED APPLICATION

This application is the U.S. national stage application of International Patent Application No. PCT/EP2017/072944, filed Sep. 12, 2017.

The Sequence Listing for this application is labeled "Seq-List.txt" which was created on Feb. 14, 2019 and is 211 KB. The entire content of the sequence listing is incorporated herein by reference in its entirety.

The present invention relates to variants of acid-alpha glucosidase and uses thereof.

Pompe disease, also known as glycogen storage disease (GSD) type II and acid maltase deficiency, is an autosomal recessive metabolic myopathy caused by a deficiency of the lysosomal enzyme acid alpha-glucosidase (GAA). GAA is an exo-1,4 and 1,6-α-glucosidase that hydrolyzes glycogen to glucose in the lysosome. Deficiency of GAA leads to glycogen accumulation in lysosomes and causes progressive damage to respiratory, cardiac, and skeletal muscle. The disease ranges from a rapidly progressive infantile course that is usually fatal by 1-2 years of age to a more slowly progressive and heterogeneous course that causes significant morbidity and early mortality in children and adults. Hirschhorn R R, The Metabolic and Molecular Bases of Inherited Disease, 3: 3389-3420 (2001, McGraw-Hill); Van der Ploeg and Reuser, Lancet 372: 1342-1351 (2008).

Current human therapy for treating Pompe disease involves administration of recombinant human GAA, otherwise termed enzyme-replacement therapy (ERT). ERT has demonstrated efficacy for severe, infantile GSD II. However the benefit of enzyme therapy is limited by the need for frequent infusions and the development of inhibitor antibodies against recombinant hGAA (Amalfitano, A., et al. (2001) Genet. In Med. 3:132-138). Furthermore, ERT does not correct efficiently the entire body, probably because of a combination of poor biodistribution of the protein following peripheral vein delivery, lack of uptake from several tissues, and high immunogenicity.

As an alternative or adjunct to ERT, the feasibility of gene therapy approaches to treat GSD-II have been investigated (Amalfitano, A., et al. (1999) Proc. Natl. Acad. Sci. USA 96:8861-8866, Ding, E., et al. (2002) Mol. Ther. 5:436-446, Fraites, T. J., et al. (2002) Mol. Ther. 5:571-578, Tsujino, S., et al. (1998) Hum. Gene Ther. 9:1609-1616). However, muscle-directed gene transfer to correct the genetic defect has to face the limitation of the systemic nature of the disease and the fact that muscle expression of a transgene tends to be more immunogenic compared with other tissues.

Doerfler et al., 2016 describe the combined administration of two constructs encoding a human codon-optimized GAA, one under the control of a liver specific promoter and the other one under the control of a muscle-specific promoter. Liver-specific promoter driven expression of GAA is employed to promote immune tolerance to GAA in a Gaa$^{-/-}$ mouse model, while muscle-specific promoter driven expression of GAA provides expression of the therapeutic protein in part of the tissues targeted for therapy. However, this strategy is not entirely satisfactory in that it requires the use of multiple constructs and it does not result in body wide expression of GAA.

Modified GAA proteins have been proposed in the past to improve lysosomal storage disease treatment. In particular, application WO2004064750 and Sun et al. 2006, disclose a chimeric GAA polypeptide comprising a signal peptide operably linked to GAA as a way to enhance targeting of the protein to the secretory pathway.

However, therapies available to the patient are not entirely satisfactory and improved GAA polypeptides and GAA production is still a need in the art. In particular, a need still exists of a long term efficacy of the treatment with GAA, of high level GAA production, of improved immunological tolerance to the produced GAA polypeptide, and of improved uptake of GAA by the cells and tissues in need thereof. In addition, in WO2004064750 and Sun et al., 2006, tissue distribution of the chimeric GAA polypeptide disclosed therein is not entirely satisfactory. Therefore, a need still exists for a GAA polypeptide that would be fully therapeutic, by allowing a correction of glycogen accumulation in most if not all tissues of interest.

SUMMARY OF THE INVENTION

The present invention relates to GAA variants that are expressed and secreted at higher levels compared to the wild type GAA protein and that elicit improved correction of the pathological accumulation of glycogen body-wide and results in the induction of immunological tolerance to GAA.

According to one aspect, the invention relates to a truncated GAA polypeptide, comprising a deletion of at least one amino acid from the N-terminal end of a parent GAA polypeptide, wherein the parent polypeptide corresponds to a precursor form of a GAA polypeptide devoid of its signal peptide. In a particular embodiment, said truncated GAA polypeptide has at least 2, in particular at least 2, in particular at least 3, in particular at least 4, in particular at least 5, in particular at least 6, in particular at least 7, in particular at least 8 consecutive amino acids deleted at its N-terminal end as compared to the parent GAA polypeptide. In another embodiment, said truncated GAA polypeptide has at most 75, in particular at most 70, in particular at most 60, in particular at most 55, in particular at most 50, in particular at most 47, in particular at most 46, in particular at most 45, in particular at most 44, in particular at most 43 consecutive amino acids deleted at its N-terminal end as compared to the parent GAA polypeptide. In a further particular embodiment, said truncated GAA polypeptide has at most 47, in particular at most 46, in particular at most 45, in particular at most 44, in particular at most 43 consecutive amino acids deleted at its N-terminal end as compared to the parent GAA polypeptide. In another particular embodiment, said truncated GAA polypeptide has 1 to 75, in particular 1 to 47, in particular 1 to 46, in particular 1 to 45, in particular 1 to 44, in particular 1 to 43 consecutive amino acids deleted at its N-terminal end as compared to the parent GAA polypeptide. In another embodiment, said truncated GAA polypeptide has 2 to 43, in particular 3 to 43, in particular 4 to 43, in particular 5 to 43, in particular 6 to 43, in particular 7 to 43, in particular 8 to 43 consecutive amino acids deleted at its N-terminal end as compared to the parent GAA polypeptide. In a more particular embodiment, said truncated GAA polypeptide has 6, 7, 8, 9, 10, 27, 28, 29, 30, 31, 40, 41, 42, 43, 44, 45, 46 or 47 consecutive amino acids deleted at its N-terminal end as compared to a parent GAA polypeptide, in particular 7, 8, 9, 28, 29, 30, 41, 42, 43 or 44, more particularly 8, 29, 42 or 43 consecutive amino acids truncated at its N-terminal end as compared to a parent GAA polypeptide. In a further particular embodiment, the parent polypeptide is a human GAA (hGAA), in particular a hGAA having the amino acid sequence shown in SEQ ID NO:1 or SEQ ID NO:33, in particular SEQ ID NO:1.

In a particular embodiment, the truncated GAA polypeptide of the invention has the sequence shown in SEQ ID NO:27, SEQ ID NO:28, SEQ ID NO:34 and SEQ ID NO:35.

Moreover, the truncated GAA polypeptide of the invention may further comprise a signal peptide fused to its N-terminal end, in particular a signal peptide selected in the group consisting of SEQ ID NO:3 to 7, in particular the signal peptide of SEQ ID NO:3.

In another aspect, the invention relates to a nucleic acid molecule encoding a truncated GAA polypeptide as described above, optionally fused to a signal peptide via its N-terminal end. In some embodiments, the nucleic acid molecule has a nucleotide sequence optimized to improve the expression of and/or improve immune tolerance to the truncated GAA polypeptide in vivo, in particular in a human subject.

In yet another aspect, the invention relates to a nucleic acid construct, comprising the nucleic acid molecule of the invention operably linked to one or more regulatory sequences such as a promoter, an intron, a polyadenylation signal and/or an enhancer (for example a cis-regulatory module, or CRM). In a particular embodiment, the promoter is a liver-specific promoter preferably selected in the group consisting of the alpha-1 antitrypsin promoter (hAAT), the transthyretin promoter, the albumin promoter and the thyroxine-binding globulin (TBG) promoter. In another particular embodiment, the promoter is a muscle-specific promoter, such as the Spc5-12, MCK and desmin promoters. In another embodiment, the promoter is an ubiquitous promoter such as the CMV, CAG and PGK promoters. The nucleic acid construct may further optionally comprises an intron, in particular an intron selected in the group consisting of a human beta globin b2 (or HBB2) intron, a FIX intron, a chicken beta-globin intron and a SV40 intron, wherein said intron is optionally a modified intron such as a modified HBB2 intron of SEQ ID NO:17, a modified FIX intron of SEQ ID NO:19, or a modified chicken beta-globin intron of SEQ ID NO:21. In a particular embodiment of the nucleic acid construct of the invention, said construct comprises, preferably in this order: an enhancer; an intron; a promoter, in particular a liver-specific promoter; the nucleic acid sequence encoding the GAA protein; and a polyadenylation signal, the construct comprising preferably, in this order: an ApoE control region; a HBB2 intron, in particular a modified HBB2 intron; a hAAT promoter; the nucleic acid sequence encoding the truncated GAA polypeptide; and a bovine growth hormone polyadenylation signal. In specific embodiments, said nucleic acid construct more particularly comprises the nucleotide sequence of any one of SEQ ID NO:22 to 26.

In another aspect, the invention relates to a vector comprising the nucleic acid molecule or the nucleic acid construct herein disclosed. The vector of the invention may be in particular a viral vector, preferably a retroviral vector, such as a lentiviral vector, or an AAV vector. Preferably, the vector is a single-stranded or double-stranded self-complementary AAV vector, preferably an AAV vector with an AAV-derived capsid, such as an AAV1, AAV2, variant AAV2, AAV3, variant AAV3, AAV3B, variant AAV3B, AAV4, AAV5, AAV6, variant AAV6, AAV7, AAV8, AAV9, AAV10 such as AAVcy10 and AAVrh10, AAVrh74, AAVdj, AAV-Anc80, AAV-LK03, AAV2i8, a porcine AAV capsid, such as AAVpo4 and AAVpo6 capsid, or with a chimeric capsid. In a specific embodiment, the vector is an AAV vector with an AAV8, AAV9, AAVrh74 or AAV2i8 capsid, in particular an AAV8, AAV9 or AAVrh74 capsid, more particularly an AAV8 capsid.

In yet another aspect, the invention provides a cell transformed with the nucleic acid molecule, the nucleic acid construct or the vector of the invention. More particularly, the cell is a liver cell or a muscle cell.

In a particular aspect, the invention provides a pharmaceutical composition, comprising, in a pharmaceutically acceptable carrier, the truncated GAA polypeptide, the nucleic acid molecule, the nucleic acid construct, the vector, or the cell of the invention.

The invention further relates to the truncated GAA polypeptide, the nucleic acid molecule, the nucleic acid construct, the vector, or the cell of the invention, for use as a medicament.

The invention further provides the truncated GAA polypeptide, the nucleic acid molecule, the nucleic acid construct, the vector, or the cell of the invention, for use in a method for treating a glycogen storage disease. In a particular embodiment, the glycogen storage disease is GSDI, GSDII, GSDIII, GSDIV, GSDV, GSDVI, GSDVII, GSD-VIII or lethal congenital glycogen storage disease of the heart. In a more particular embodiment, the glycogen storage disease is selected in the group consisting of GSDI, GSDII and GSDIII, more particularly in the group consisting of GSDII and GSDIII. In an even more particular embodiment, the glycogen storage disease is GSDII.

LEGENDS TO THE FIGURES

FIG. 1. Deletion of portions of hGAA increase its secretion in vitro. Panel A. Human hepatoma cells (Huh7) were transfected using Lipofectamine™ with a control plasmid expressing green fluorescent protein (GFP), or plasmids expressing wild-type hGAA (hGAA) or hGAA sequence optimized according to two distinct algorithms (hGAAco 1 and co2, respectively). The different hGAA constructs contained the wild-type or the human alpha-1-antitrypsin signal peptide (sp2). Truncated hGAA has been obtained by deletion of 8 amino acids after the signal peptide (Δ8). 48 hours after transfection the activity of hGAA in the culture media was measured by a fluorogenic enzymatic assay and GAA activity evaluated against a standard curve of the product of the reaction as indicated in Materials and Methods. The histogram plot shows the average±SE of the levels of secreted hGAA deriving from three different experiments. Statistical analysis has been performed by paired t-test, in the histogram are reported the p-values obtained (*=p<0.05 as indicated). Panel B. Human hepatoma cells (Huh7) were transfected using lipofectamine with a control plasmid expressing GFP, or plasmids expressing hGAAco1 with wild-type or chymotrypsinogen B1 signal peptide (sp7). hGAA protein has been truncated by removing 8 or 42 amino acids after the signal peptide (Δ8 and Δ42, respectively). 48 hours after transfection the activity of hGAA in the culture media was measured by a fluorogenic enzymatic assay as indicated above. The histogram plot shows the average±SE of the levels of secreted hGAA deriving from three different experiments. Statistical analysis has been performed by ANOVA (*=p<0.05 as indicated).

Figure 2:
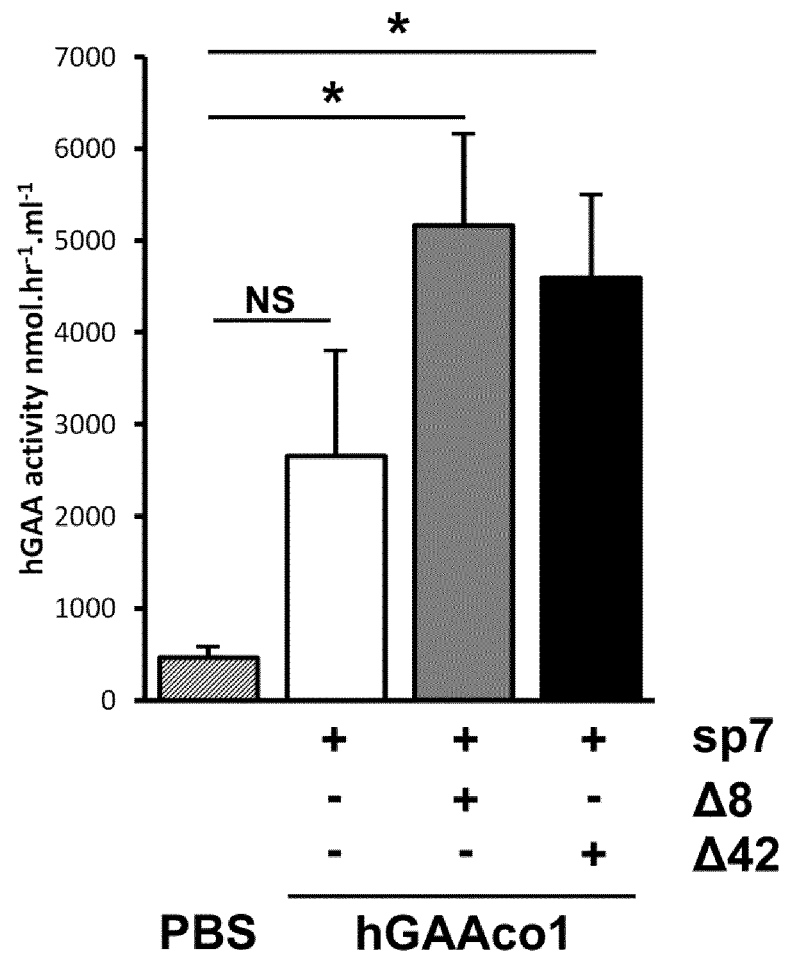

FIG. 2. Deletion of portions of hGAA increases its secretion in the bloodstream in a Pompe disease mouse model. 3 months-old GAA$^{-/-}$ mice (n=4-5 mice/group) were intravenously injected with PBS or with 2E12 vg/kg of AAV8 vectors expressing sequence optimized hGAA (hGAAco1) under the transcriptional control of a liver specific promoter. Wild-type signal peptide of hGAA has been substituted with chymotrypsinogen B1 signal peptide (sp7) and the sequence of hGAA has been either used as the full-length native sequence or truncated by removing 8 or 42 amino acids after the signal peptide (Δ8 and Δ42, respectively). One month after the injection, mice were bled and hGAA activity was measured using a fluorogenic assay in serum. Statistical analysis was performed by ANOVA (*=p<0.05 as indicated).

Figure 3:
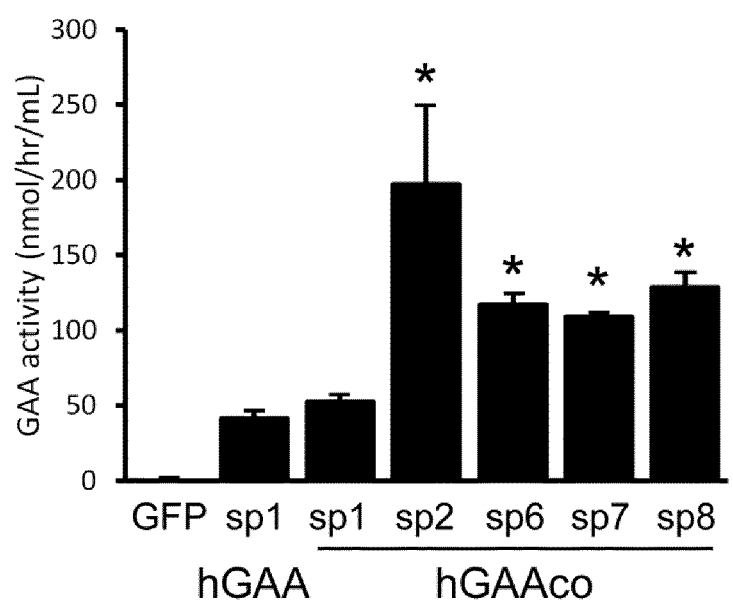

FIG. 3. Signal peptides enhance secretion of hGAA. Human hepatoma cells (Huh7) were transfected by Lipofectamine™ with a control plasmid (GFP), a plasmid expressing wild-type hGAA (noted as sp1), or plasmids expressing sequence optimized Δ8 hGAA (hGAAco) fused with signal peptides 6-8 (sp6-8). 48 hours after transfection the activity of hGAA in the culture media was measured by a fluorogenic enzymatic assay and GAA activity evaluated against a standard curve of 4-methylumbelliferone. The histogram plot shows the average±SE of the levels of secreted hGAA deriving from three different experiments. Statistical analysis has been performed by ANOVA (*=p<0.05 vs mock transfected cells).

Figure 4:
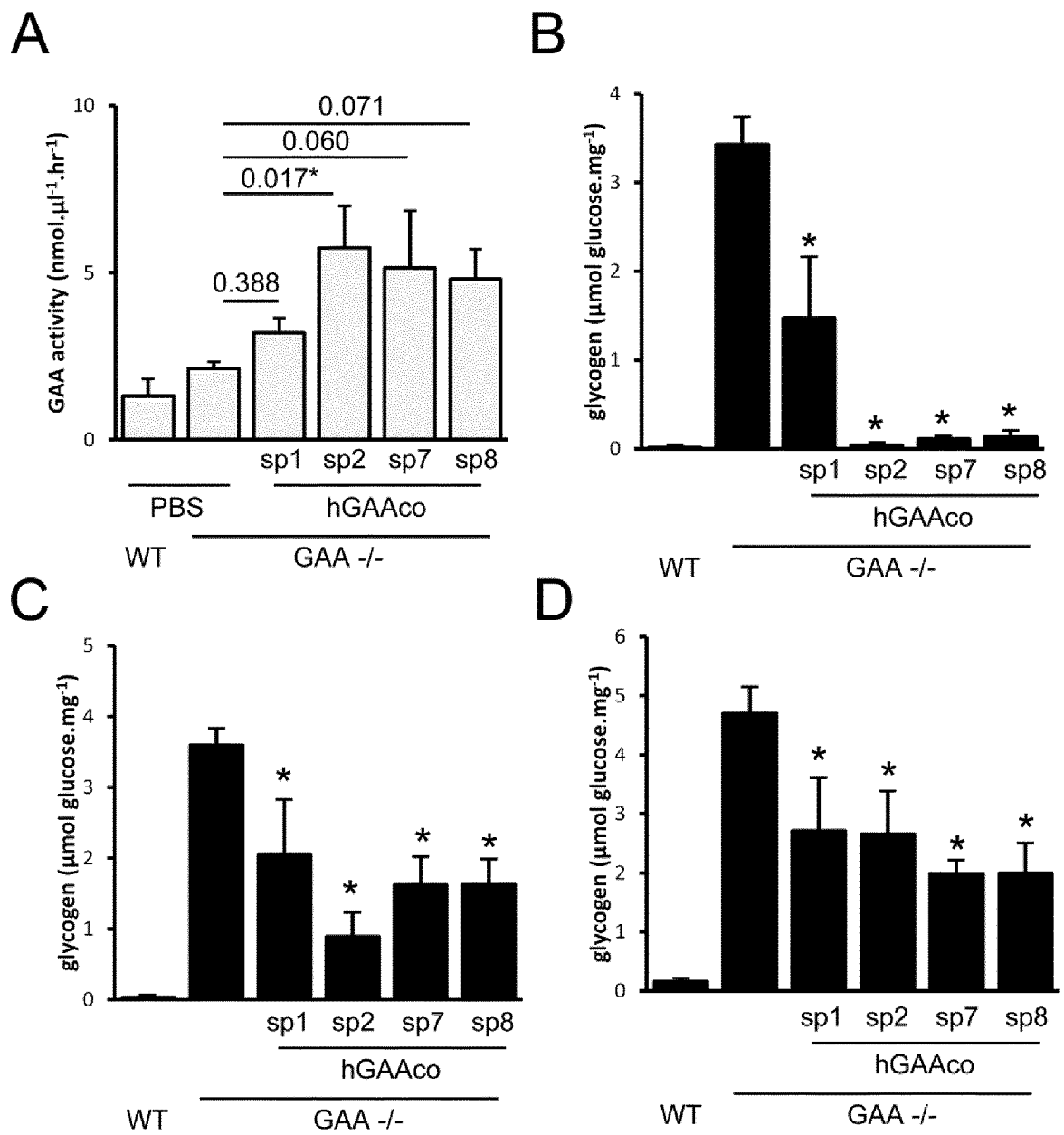

FIG. 4. Truncated Δ8 hGAA efficiently correct glycogen accumulation in a Pompe disease mouse model. 4 months-old wild type (WT) and $GAA^{-/-}$ mice (n=4-5 mice/group) were intravenously injected with PBS or 6E11 vg/kg of AAV8 vectors expressing sequence optimized Δ8 hGAA (hGAAco) under the transcriptional control of human alpha-1-antytripsin promoter and fused with signal peptide 1, 2, 7 and 8 (sp1,2,7,8). Panel A. The histogram shows the hGAA activity measured by fluorogenic assay in blood three months after vectors injection. Statistical analysis has been performed by ANOVA, in the histogram are reported the p-values obtained vs PBS treated GAA −/− animals (*=p<0.05). Panel B-D. Biochemical correction of glycogen content in heart, diaphragm and quadriceps. 4 months-old $GAA^{-/-}$ mice were treated as described above. Three months after the injections, mice were sacrificed and the glycogen content has been evaluated. Histograms show the glycogen content expressed as glucose released after enzymatic digestion of glycogen, measured in the heart (panel B), diaphragm (panel C) and quadriceps (panel D). Statistical analysis has been performed by ANOVA (*=p<0.05 vs PBS injected GAA −/− mice).

Figure 5:
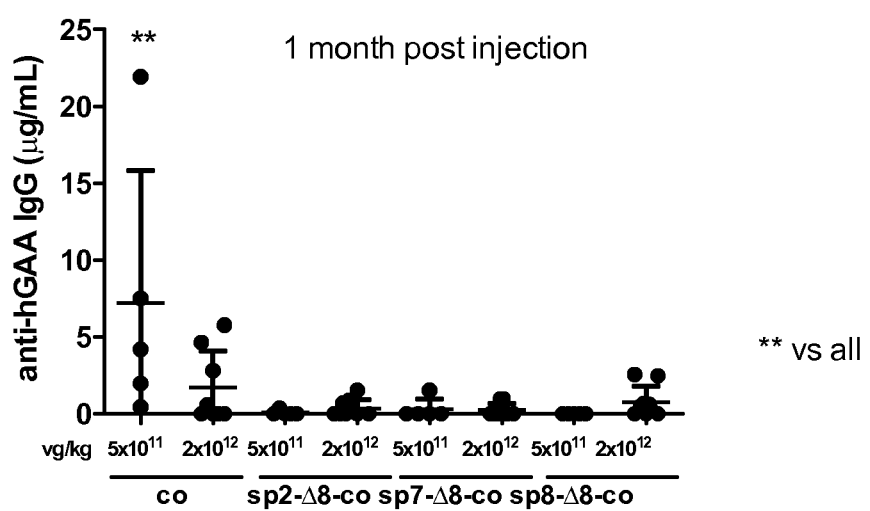

FIG. 5. Highly secreted hGAA reduces humoral response in a Pompe disease mouse model. 4 months-old GAA−/− mice were intravenously injected with PBS or with two different doses (5E11 or 2E12 vg/kg) of AAV8 vectors comprising an optimized sequence under the transcriptional control of human alpha-1-antytripsin promoter, encoding Δ8 hGAA, fused to signal peptide 1 (co), signal peptide 2 (sp2-Δ8-co), signal peptide 7 (sp7-Δ8-co) or signal peptide 8 (sp8-Δ8-co). 1 month after the injections, sera were analyzed for the presence of anti-hGAA antibodies by ELISA. The quantification has been performed using purified mouse IgG as standard. Statistical analysis has been performed by ANOVA with Dunnett's post-hoc test (*=p<0.01).

Figure 6:
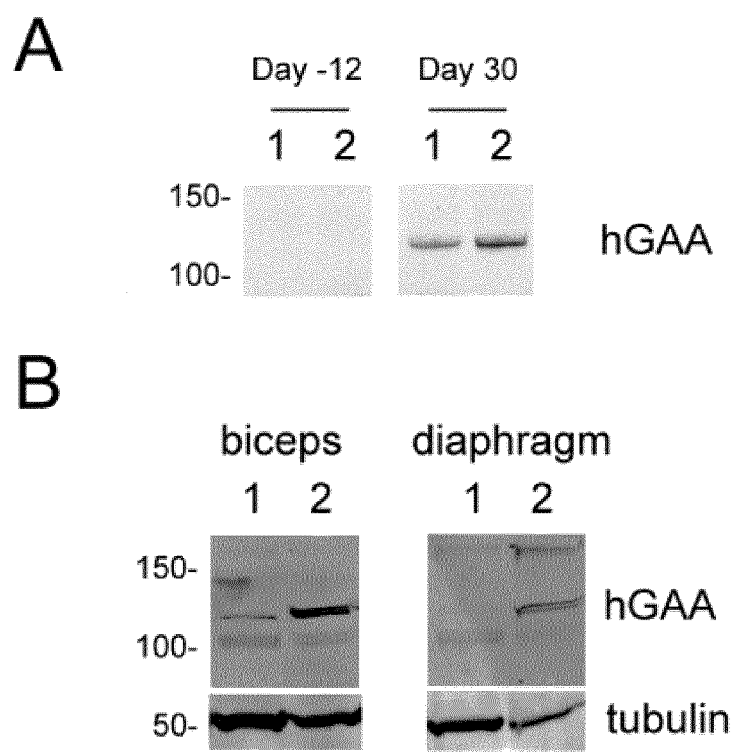

FIG. 6. AAV8-hAAT-sp7-Δ8-hGAAco1 injection leads to efficacious secretion of hGAA in the blood and uptake in muscle in NHP. Two Macaca Fascicularis monkeys were injected at day 0 with 2E12 vg/kg of AAV8-hAAT-sp7-Δ8-hGAAco1. Panel A hGAA western blot performed on serum from the two monkeys obtained twelve days before and 30 days after vector administration. On the left are indicated the positions of the bands of the molecular weight marker running in parallel with the samples. Panel B Three months after vector injection the monkeys were sacrificed and tissues harvested for biochemical evaluation of hGAA uptake. A hGAA Western blot was performed on tissue extracts obtained from biceps and diaphragm. An anti-tubulin antibody was used as loading control. On the left are indicated the positions of the bands of the molecular weight marker running in parallel with the samples.

Figure 7:
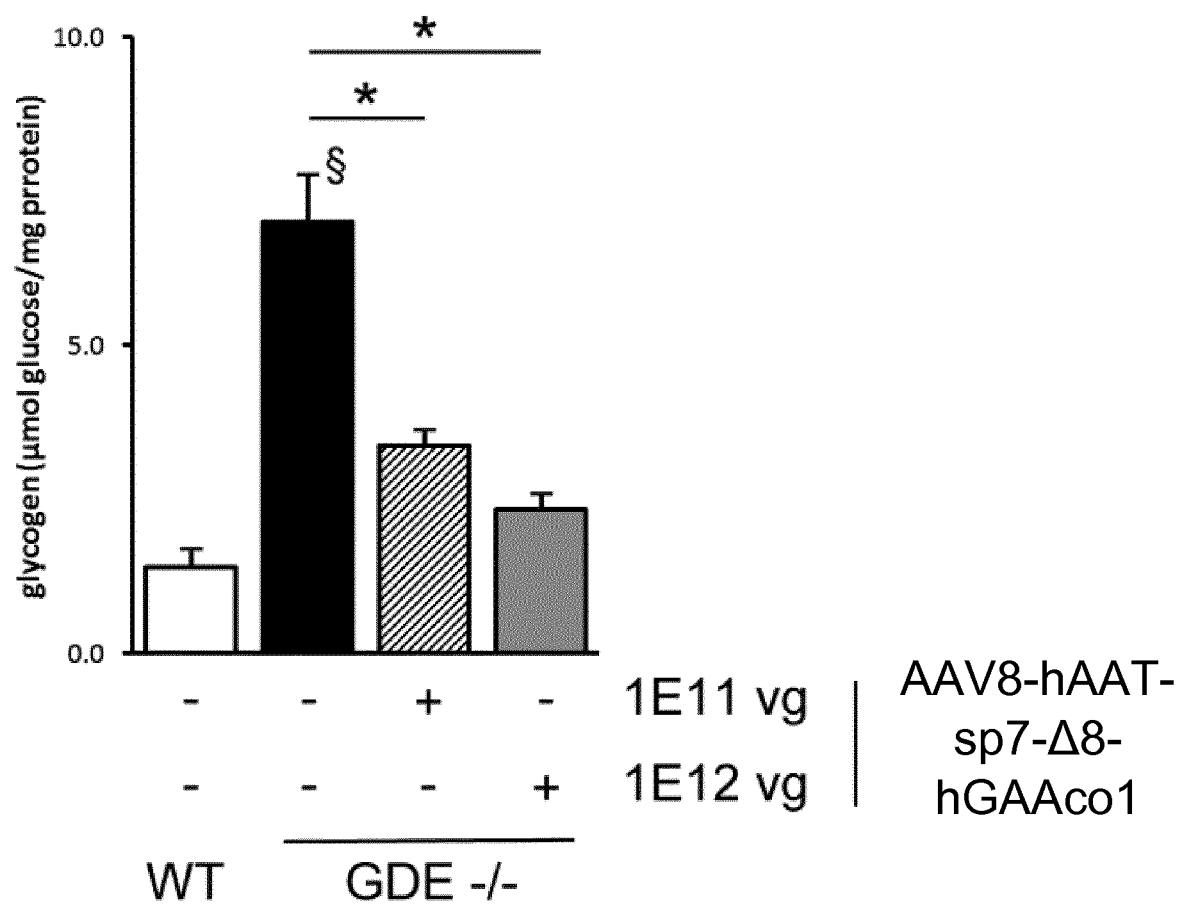

FIG. 7. Biochemical correction of glycogen content in the liver of GDE −/− animals injected with hGAA expressing vector. 3 months-old wild-type (WT) or GDE −/− mice were intravenously injected with PBS or AAV8 vectors expressing codon optimized hGAA under the transcriptional control of human alpha-1-antytripsin promoter and fused with signal peptide 7 (AAV8-hAAT-sp7-Δ8-hGAAco1) at the dose of 1E11 or 1E12 vg/mouse. The histogram plot shows the glycogen content expressed as glucose released after enzymatic digestion of glycogen, measured in the liver. Statistical analysis was performed by ANOVA (*=p<0.05 vs PBS injected GDE −/− mice, §=p<0.05 vs PBS injected WT animals).

Figure 8:
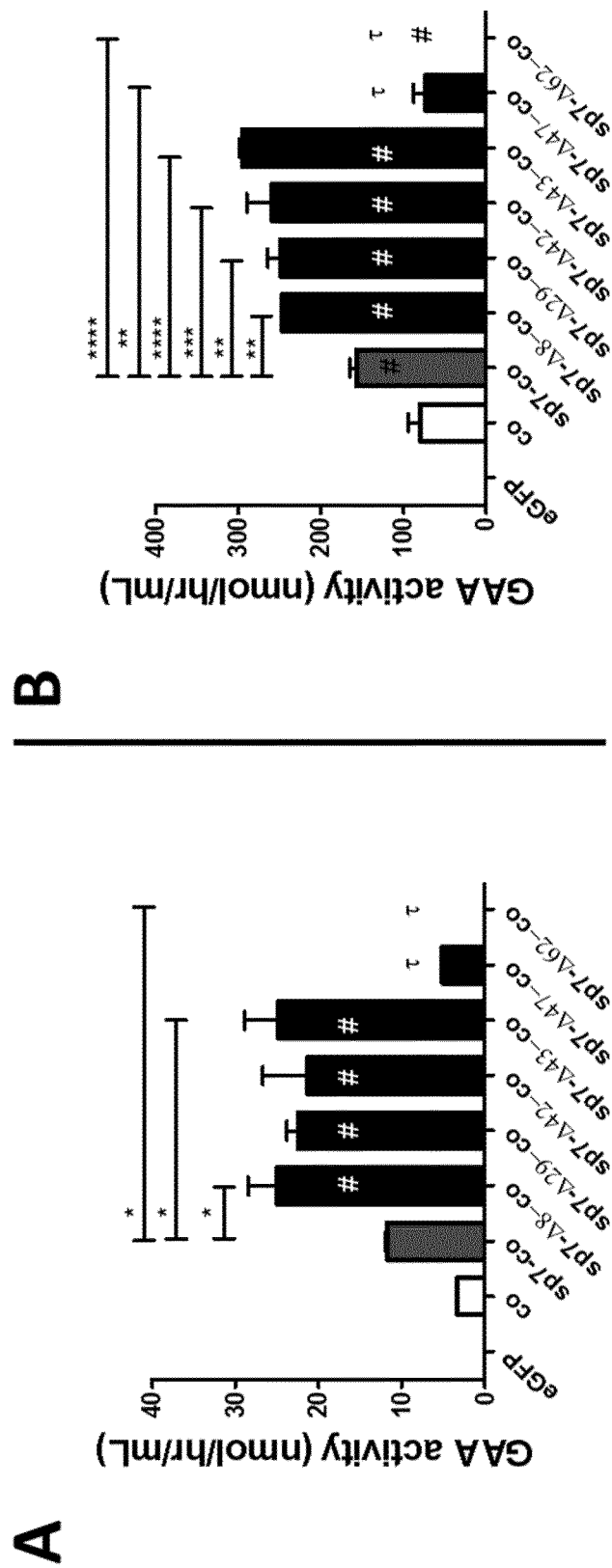

FIG. 8. GAA activity in media of cells transfected with plasmids encoding different GAA variants. GAA activity was measured in the media of HuH7 cells 24 (panel A) and 48 hours (panel B) following transfection of plasmids comprising optimized sequences encoding native GAA combined to the native GAA sp1 signal peptide (co) or encoding engineered GAA including native GAA combined to the heterologous sp7 signal peptide (sp7-co). The effect of different deletions in the GAA coding sequence after the sp7 signal peptide was evaluated (sp7-Δ8-co, sp7-Δ29-co, sp7-Δ42-co, sp7-Δ43-co, sp7-Δ47-co, sp7-Δ62-co). A plasmid encoding for eGFP was used as negative control. Statistical analysis was performed by One-way ANOVA with Tukey post-hoc. Hash marks (#) in the bars show statistically significant differences vs. co; tau symbols (τ) show statistically significant differences vs. sp7-Δ8-co, sp7-Δ29-co, sp7-Δ42-co, sp7-Δ43-co. Data are average±SD of two independent experiments. *p<0.05, p<0.01, *p<0.001, ****p<0.0001 except where different symbols are used.

Figure 9:
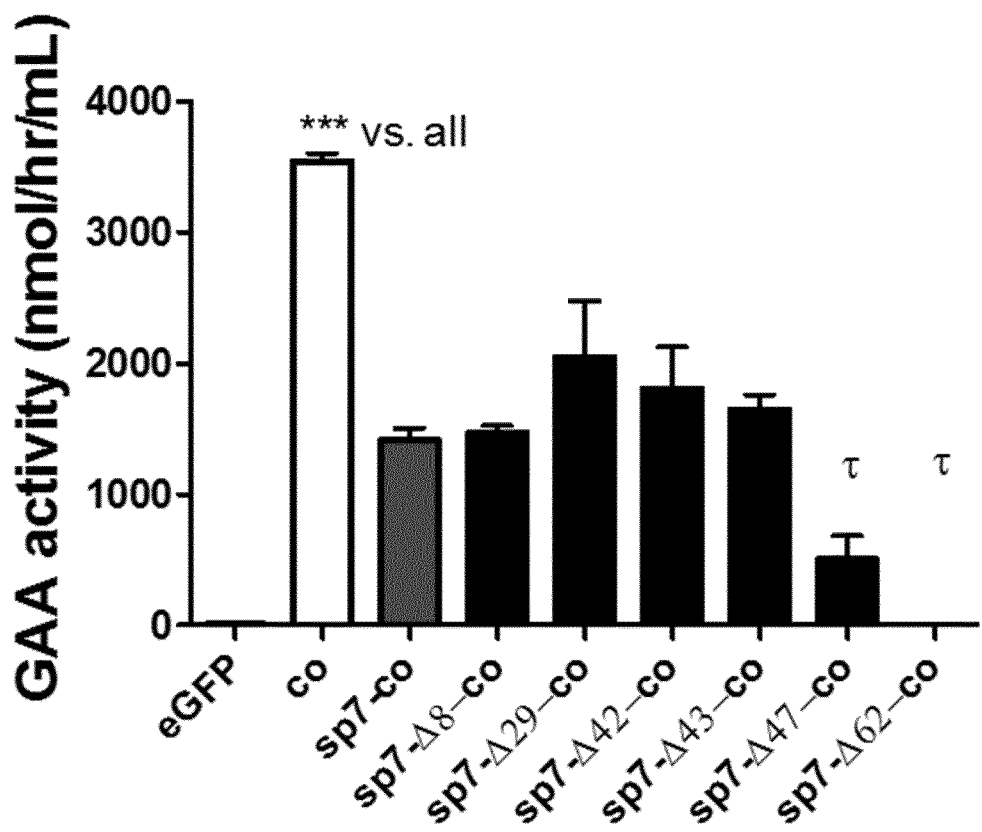

FIG. 9. Intracellular GAA activity of different GAA variants. GAA activity was measured in the lysates of HuH7 cells 48 hours following transfection of plasmids comprising optimized sequences encoding native GAA combined to the native GAA sp1 signal peptide (co) or encoding engineered GAA including native GAA combined to the heterologous sp7 signal peptide (sp7-co). The effect of different deletions in the GAA coding sequence after the signal peptide was evaluated (sp7-Δ8-co, sp7-Δ29-co, sp7-Δ42-co, sp7-Δ43-co, sp7-Δ47-co, sp7-Δ62-co). A plasmid encoding for eGFP was used as negative control. Statistical analysis was performed by One-way ANOVA with Tukey post-hoc. Tau symbols (τ) show statistically significant differences vs. sp7-co, sp7-Δ8-co, sp7-Δ29-co, sp7-Δ42-co, sp7-Δ43-co. Data are average±SD of two independent experiments. *p<0.05, p<0.01, *p<0.001, ****p<0.0001 except where different symbols are used.

Figure 10:
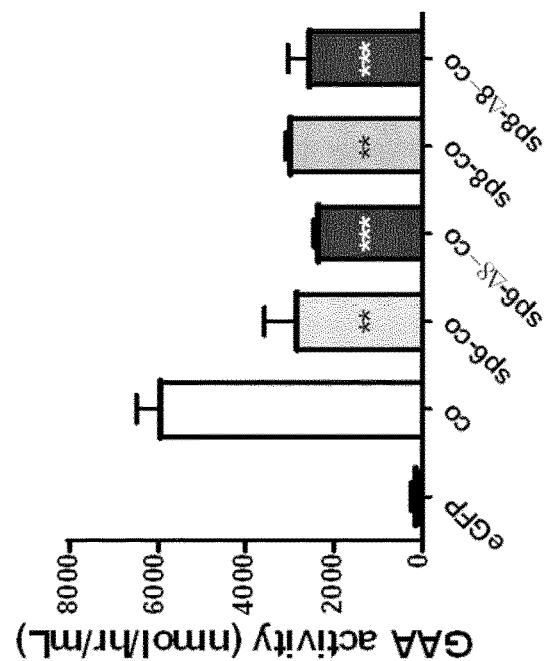
Figure 10:
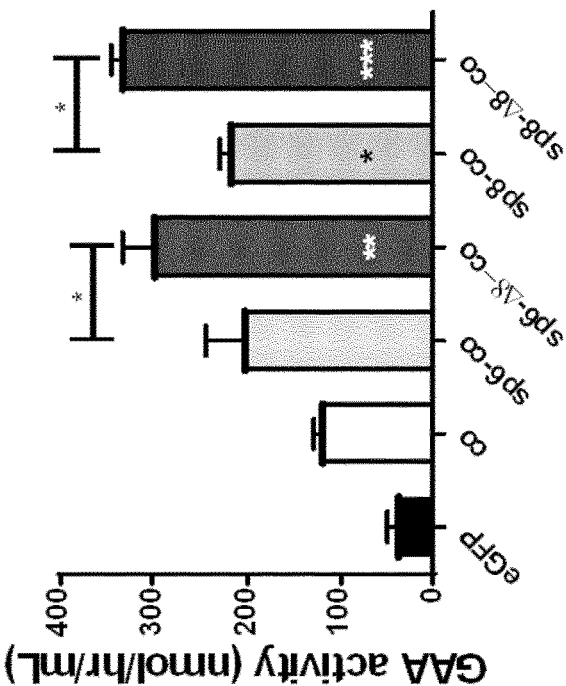

FIG. 10. Increased GAA activity in cell media using the Δ8 deletion combined with the sp6 or sp8 signal peptides. GAA activity was measured in the media (panel A) and lysates (panel B) of HuH7 cells 48 hours following transfection of plasmids comprising optimized sequences encoding native GAA combined to the native GAA sp1 signal peptide (co) or encoding engineered GAA including native GAA combined to the heterologous sp6 or sp8 signal peptide (sp6-co or sp8-co). The effect of the deletion of 8 amino-acids in the GAA coding sequence after the signal peptide is evaluated (sp6-Δ8-co, sp8-Δ8-co). A plasmid encoding eGFP was used as negative control. Statistical analysis was performed by One-way ANOVA with Tukey post-hoc. Asterics in the bars shows statistically significant differences vs.

co. Data are average±SD of two independent experiments. *p<0.05, p<0.01, *p<0.001, ****p<0.0001 except where different symbols are used.

DETAILED DESCRIPTION OF THE INVENTION

The present invention relates to a truncated GAA polypeptide, to a nucleic acid molecule encoding such a truncated GAA polypeptide, to a nucleic acid construct comprising said nucleic acid, to a vector comprising said nucleic acid construct, to a cell comprising said nucleic acid molecule or construct or vector, and to a pharmaceutical composition comprising a polypeptide, a nucleic acid molecule, a nucleic acid construct, a vector or a cell according to the invention. The inventors have surprisingly shown that a truncated form of GAA according to the invention greatly improves GAA secretion while reducing its immunogenicity.

Lysosomal acid α-glucosidase or "GAA" (E.C. 3.2. 1.20) (1,4-α-D-glucan glucohydrolase), is an exo-1,4-α-D-glucosidase that hydrolyses both α-1,4 and α-1,6 linkages of oligosaccharides to liberate glucose. A deficiency in GAA results in glycogen storage disease type II (GSDII), also referred to as Pompe disease (although this term formally refers to the infantile onset form of the disease). It catalyzes the complete degradation of glycogen with slowing at branching points. The 28 kb human acid α-glucosidase gene on chromosome 17 encodes a 3.6 kb mRNA which produces a 951 amino acid polypeptide (Hoefsloot et al., (1988) EMBO J. 7: 1697; Martiniuk et al., (1990) DNA and Cell Biology 9: 85). The enzyme receives co-translational N-linked glycosylation in the endoplasmic reticulum. It is synthesized as a 110-kDa precursor form, which matures by extensive glycosylation modification, phosphorylation and by proteolytic processing through an approximately 90-kDa endosomal intermediate into the final lysosomal 76 and 67 kDa forms (Hoefsloot, (1988) EMBO J. 7: 1697; Hoefsloot et al., (1990) Biochem. J. 272: 485; Wisselaar et al., (1993) J. Biol. Chem. 268: 2223; Hermans et al., (1993) Biochem. J. 289: 681).

In patients with GSD II, a deficiency of acid α-glucosidase causes massive accumulation of glycogen in lysosomes, disrupting cellular function (Hirschhorn, R. and Reuser, A. J. (2001), in The Metabolic and Molecular Basis for Inherited Disease, (eds, Scriver, C. R. et al.) pages 3389-3419 (McGraw-Hill, New York). In the most common infantile form, patients exhibit progressive muscle degeneration and cardiomyopathy and die before two years of age. Severe debilitation is present in the juvenile and adult onset forms.

Furthermore, patients having other GSDs may benefit from the administration of an optimized form of GAA. For example, it has been shown (Sun et al. (2013) Mol Genet Metab 108(2): 145; WO2010/005565) that administration of GAA reduces glycogen in primary myoblasts from glycogen storage disease type III (GSD III) patients.

In particular, in the context of the present invention, a "precursor form of GAA" is a form of the GAA polypeptide that comprises its natural signal peptide. For example, the sequence of SEQ ID NO:2 is the precursor form of human GAA (hGAA). Within SEQ ID NO:2, amino acid residues 1-27 correspond to the signal peptide of the hGAA polypeptide. This sequence of the signal peptide of hGAA is also represented in SEQ ID NO:4.

In the context of the present invention, the truncated GAA polypeptide of the invention is derived from a parent GAA polypeptide. According to the present invention a "parent GAA polypeptide" is a functional, precursor GAA sequence as defined above, but devoid of its signal peptide. For example, with reference to the typical wild-type human GAA polypeptide, a complete wild-type GAA polypeptide (i.e. a precursor form of GAA) is represented in SEQ ID NO:2 or in SEQ ID NO:30 and has a signal peptide (corresponding to amino acids 1-27 of SEQ ID NO:2 or SEQ ID NO:30), whereas the parent GAA polypeptide serving as basis for the truncated GAA forms of these wild-type human GAA polypeptides are represented in SEQ ID NO:1 and SEQ ID NO:33, respectively and have no signal peptide. In this example, the latter, corresponding to amino acids 28-952 of SEQ ID NO:2 and to amino acids 28-952 of SEQ ID NO:30, is referred to as a parent GAA polypeptide.

According to the invention, the truncated GAA polypeptide of the invention is a functional GAA polypeptide, i.e. it has the functionality of wild-type GAA polypeptide. As defined above, the functionality of wild-type GAA is to hydrolyse both α-1,4 and α-1,6 linkages of oligosaccharides and polysaccharides, more particularly of glycogen, to liberate glucose. The functional GAA protein encoded by the nucleic acid of the invention may have a hydrolysing activity on glycogen of at least 50%, 60%, 70%, 80%, 90%, 95%, 99%, or at least 100% as compared to the wild-type GAA polypeptide of SEQ ID NO:1 or SEQ ID NO:33. The activity of the GAA protein encoded by the nucleic acid of the invention may even be of more than 100%, such as of more than 110%, 120%, 130%, 140%, or even more than 150% of the activity of the wild-type GAA protein of SEQ ID NO:1 or of SEQ ID NO:33.

The amino acid sequence of the parent GAA polypeptide or its coding sequence can be derived from any source, including avian and mammalian species. The term "avian" as used herein includes, but is not limited to, chickens, ducks, geese, quail, turkeys and pheasants. The term "mammal" as used herein includes, but is not limited to, humans, simians and other non-human primates, bovines, ovines, caprines, equines, felines, canines, lagomorphs, etc. In embodiments of the invention, the parent GAA polypeptide is a human, mouse or quail, in particular a human, GAA polypeptide.

In addition, the parent GAA polypeptide may be a functional variant of a GAA polypeptide, comprising one or more amino acid modifications such as amino acid insertion, deletion and/or substitution as compared to a GAA polypeptide. For example, the parent polypeptide may be a functional derivative of a human GAA polypeptide, such as the polypeptide of SEQ ID NO:1 or SEQ ID NO:33, in particular SEQ ID NO:1, having at least 80, 85, 90, 95, 96, 97, 98 or at least 99 percent sequence identity to this human GAA polypeptide. For example, in addition to the truncation defined above, the functional variant of a GAA polypeptide may have between 0 and 50, between 0 and 30, between 0 and 20, between 0 and 15, between 0 and 10, or between 0 and 5 amino acid changes to the parent GAA polypeptide, such as the parent GAA polypeptide shown in SEQ ID NO: 1 or SEQ ID NO:33, in particular SEQ ID NO:1. In particular, the parent GAA polypeptide may consist of the human GAA polypeptide having the amino acid sequence shown in SEQ ID NO:1 or SEQ ID NO:33, in particular in SEQ ID NO:1.

The term "identical" and declinations thereof when referring to a polypeptide means that when a position in two compared polypeptide sequences is occupied by the same amino acid (e.g. if a position in each of two polypeptides is occupied by a leucine), then the polypeptides are identical at that position. The percent of identity between two polypeptides is a function of the number of matching positions shared by the two sequences divided by the number of positions compared×100. For example, if 6 of 10 of the positions in two polypeptides are matched then the two sequences are 60% identical. Generally, a comparison is made when two sequences are aligned to give maximum identity. Various bioinformatic tools known to the one skilled in the art might be used to align nucleic acid sequences such as BLAST or FASTA.

The parent GAA polypeptide may also be a GAA variant such as GAA II as described by Kunita et al., (1997) Biochemica et Biophysica Acta 1362: 269; GAA polymorphisms and SNPs are described by Hirschhorn, R. and Reuser, A. J. (2001) In The Metabolic and Molecular Basis for Inherited Disease (Scriver, C. R., Beaudet, A. L., Sly, W. S. & Valle, D. Eds.), pp. 3389-3419. McGraw-Hill, New York, see pages 3403-3405. Any variant GAA polypeptide known in the art may be used as a basis for defining a parent GAA polypeptide. Illustrative variant GAA polypeptides include SEQ ID NO:2 (NCBI reference sequence NP_000143.2); SEQ ID NO:29 (GenBank AAA52506.1); SEQ ID NO:30 (GenBank CAA68763.1); SEQ ID NO:31 (GenBank: EAW89583.1) and SEQ ID NO:32 (GenBank ABI53718.1). Other useful variants include those described in Hoefsloot et al., (1988) EMBO J. 7: 1697; and Van Hove et al., (1996) Proc. Natl. Acad. Sci. USA 93: 65 (human) and GenBank Accession number NM_008064 (mouse). Other variant GAA polypeptides include those described in WO2012/145644, WO00/34451 and U.S. Pat. No. 6,858,425. In a particular embodiment, the parent GAA polypeptide is derived from the amino acid sequence shown in SEQ ID NO:2 or SEQ ID NO:30.

The truncated form of GAA according to the invention is a N-terminally truncated form of a parent GAA polypeptide, wherein at least one amino acid is deleted from the N-terminal end of said parent GAA polypeptide.

By "truncated form", it is meant a GAA polypeptide that comprises one or several consecutive amino acids deleted from the N-terminal part of a parent GAA polypeptide. For example, the GAA moiety may have 1 to 75 consecutive amino acids or more than 75 consecutive amino acids truncated from its N-terminal end as compared to the parent GAA polypeptide. Specifically, the truncated GAA polypeptide may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 consecutive amino acids truncated from its N-terminal end as compared to the parent GAA protein (in particular a truncated form of the parent hGAA protein shown in SEQ ID NO: 1 or SEQ ID NO:33, in particular in SEQ ID NO:1). Using an alternative nomenclature, the GAA polypeptide resulting from the truncation of 1 amino acid in the parent GAA polypeptide is referred to as Δ1 GAA truncated form, the GAA polypeptide resulting from the truncation of 2 consecutive amino acids from the N-terminal end is referred to as Δ2 GAA truncated form, the GAA polypeptide resulting from the truncation of 3 consecutive amino acids in the parent GAA polypeptide is referred to as Δ3 GAA truncated form), etc. In a particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46, Δ47, Δ48, Δ49, Δ50, Δ51, Δ52, Δ53, Δ54, Δ55, Δ56, Δ57, Δ58, Δ59, Δ60, Δ61, Δ62, Δ63, Δ64, Δ65, Δ66, Δ67, Δ68, Δ69, Δ70, Δ71, Δ72, Δ73, Δ74 or Δ75 GAA truncated form (in particular a truncated form of the parent hGAA protein shown in SEQ ID NO: 1 or SEQ ID NO:33, in particular in SEQ ID NO:1).

In another particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46 or Δ47 GAA truncated form (in particular a truncated form of the parent hGAA protein shown in SEQ ID NO: 1 or SEQ ID NO:33, in particular in SEQ ID NO:1).

In another particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45 or Δ46 GAA truncated form (in particular a truncated form of the parent hGAA protein shown in SEQ ID NO: 1 or SEQ ID NO:33, in particular in SEQ ID NO:1).

In another particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44 or Δ45 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43 or Δ44 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a 41, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42 or Δ43 GAA truncated form (in particular a truncated form of the parent hGAA protein shown in SEQ ID NO: 1 or SEQ ID NO:33, in particular in SEQ ID NO:1).

In a further particular embodiment, the truncated GAA polypeptide of the invention is a 46, Δ7, Δ8, Δ9 or Δ10 truncated form of GAA (in particular of the hGAA protein shown in SEQ ID NO: 1 or SEQ ID NO:33, in particular in SEQ ID NO:1), in particular a Δ7, Δ8 or Δ9 truncated form of GAA (in particular of the hGAA protein shown in SEQ ID NO: 1 or SEQ ID NO:33, in particular in SEQ ID NO:1), more particularly a Δ8 truncated form of GAA (in particular of the hGAA protein shown in SEQ ID NO: 1 or SEQ ID NO:33, in particular in SEQ ID NO:1).

In a further particular embodiment, the truncated GAA polypeptide of the invention is a Δ27, Δ28, Δ29, Δ30 or Δ31 truncated form of GAA (in particular of the hGAA protein shown in SEQ ID NO: 1 or SEQ ID NO:33, particular in SEQ ID NO:1), in particular a Δ28, Δ29 or Δ30 truncated form of GAA (in particular of the hGAA protein shown in SEQ ID NO: 1 or SEQ ID NO:33, in particular in SEQ ID NO:1), more particularly a Δ29 truncated form of GAA (in particular of the hGAA protein shown in SEQ ID NO: 1 or SEQ ID NO:33, in particular in SEQ ID NO:1).

In another particular embodiment, the truncated GAA polypeptide of the invention is a Δ40, Δ41, Δ42, Δ43, or Δ44 truncated form of GAA (in particular of the hGAA protein shown in SEQ ID NO: 1 or SEQ ID NO:33, particular in SEQ ID NO:1), in particular a Δ41, Δ42 or Δ43 truncated form of GAA (in particular of the hGAA protein shown in SEQ ID NO: 1 or SEQ ID NO:33, in particular in SEQ ID NO:1), more particularly a Δ42 truncated form of GAA (in particular of the hGAA protein shown in SEQ ID NO: 1 or SEQ ID NO:33, particular in SEQ ID NO:1).

In a further particular embodiment, the truncated GAA polypeptide of the invention is a Δ41, Δ42, Δ43, Δ44 or Δ45 truncated form of GAA (in particular of the hGAA protein shown in SEQ ID NO: 1), in particular a Δ42, Δ43 or Δ44 truncated form of GAA (in particular of the hGAA protein shown in SEQ ID NO: 1 or SEQ ID NO:33, in particular in SEQ ID NO:1), more particularly a Δ43 truncated form of GAA (in particular of the hGAA protein shown in SEQ ID NO: 1).

In another embodiment, the truncated GAA polypeptide of the invention is a Δ6, Δ7, Δ8, Δ9, Δ10, Δ27, Δ28, Δ29, Δ30, Δ31, Δ40, Δ41, Δ42, Δ43, Δ44, Δ45, Δ46 or Δ47 truncated form of GAA (in particular of the hGAA protein shown in SEQ ID NO: 1 or SEQ ID NO:33, particular in SEQ ID NO:1).

In another embodiment, the truncated GAA polypeptide of the invention is a Δ7, Δ8, Δ9, Δ28, Δ29, Δ30, Δ41, Δ42, Δ43 or Δ44 truncated form of GAA (in particular of the hGAA protein shown in SEQ ID NO: 1 or SEQ ID NO:33, particular in SEQ ID NO:1).

In another embodiment, the truncated GAA polypeptide of the invention is a Δ6, Δ7, Δ8, Δ9, Δ10, Δ40, Δ41, Δ42, Δ43 or Δ44, truncated form of GAA (in particular of the hGAA protein shown in SEQ ID NO: 1 or SEQ ID NO:33, particular in SEQ ID NO:1).

In another embodiment, the truncated GAA polypeptide of the invention is a Δ8, Δ29, Δ42, Δ43 or Δ47 truncated form of GAA (in particular of the hGAA protein shown in SEQ ID NO: 1 or SEQ ID NO:33, particular in SEQ ID NO:1).

In another embodiment, the truncated GAA polypeptide of the invention is a Δ8, Δ29, Δ42 or Δ43 truncated form of GAA (in particular of the hGAA protein shown in SEQ ID NO: 1 or SEQ ID NO:33, in particular in SEQ ID NO:1).

In another embodiment, the truncated GAA polypeptide of the invention is a Δ8 or Δ42 truncated form of GAA (in particular of the hGAA protein shown in SEQ ID NO: 1 or SEQ ID NO:33, particular in SEQ ID NO:1).

In a particular embodiment, of the invention, the truncated GAA polypeptide of the invention is a truncated form of a functional human GAA polypeptide. In a further particular embodiment, the parent hGAA polypeptide is the hGAA polypeptide shown in SEQ ID NO:1 or SEQ ID NO:33, in particular in SEQ ID NO:1. In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46, Δ47, Δ48, Δ49, Δ50, Δ51, Δ52, Δ53, Δ54, Δ55, Δ56, Δ57, Δ58, Δ59, Δ60, Δ61, Δ62, Δ63, Δ64, Δ65, Δ66, Δ67, Δ68, Δ69, Δ70, Δ71, Δ72, Δ73, Δ74 or Δ75 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45, Δ46 or Δ47 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44, Δ45 or Δ46 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In a variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43, Δ44 or Δ45 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, Δ43 or Δ44 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ1, Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41 or Δ42 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ2, Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ3, Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ4, Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ5, Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ6, Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ7, Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ8, Δ9, Δ10, Δ11, Δ12, Δ13, Δ14, Δ15, Δ16, Δ17, Δ18, Δ19, Δ20, Δ21, Δ22, Δ23, Δ24, Δ25, Δ26, Δ27, Δ28, Δ29, Δ30, Δ31, Δ32, Δ33, Δ34, Δ35, Δ36, Δ37, Δ38, Δ39, Δ40, Δ41, Δ42, or Δ43 GAA truncated form of a hGAA polypeptide, and more particularly of the hGAA polypeptide shown in SEQ ID NO:1 or SEQ ID NO:33, even more particularly in SEQ ID NO:1, or of a functional variant thereof comprising amino acid substitutions in the sequence shown in SEQ ID NO:1 or SEQ ID NO:33, in particular SEQ ID NO:1, and having at least 75, 80, 85, 90, 91, 92, 93, 94, 95, 96, 97, 98 or 99 percent identity to SEQ ID NO:1 SEQ ID NO:33, in particular SEQ ID NO:1.

In another variant of this embodiment, the truncated GAA polypeptide of the invention is a Δ6, Δ7, Δ8, Δ9 or Δ10, in particular a Δ7, Δ8 or Δ9, more particularly a Δ8 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ27, Δ28, Δ29, Δ30 or Δ31, in particular a Δ28, Δ29 or Δ30, more particularly a Δ29 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ40, Δ41, Δ42, Δ43 or Δ44, in particular a Δ41, Δ42 or Δ43, more particularly a Δ42 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ41, Δ42, Δ43, Δ44 or Δ45, in particular a Δ42, Δ43 or Δ44, more particularly a Δ43 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ6, Δ7, Δ8, Δ9, Δ10, Δ27, Δ28, Δ29, Δ30, Δ31, Δ40, Δ41, Δ42, Δ43, Δ44 or Δ45, in particular a 47, Δ8, Δ9, Δ28, Δ29, Δ30, Δ41, Δ42, Δ43 or Δ44, in particular a Δ8, Δ29, Δ42 or Δ43 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ6, Δ7, Δ8, Δ9, Δ10, Δ40, Δ41, Δ42, Δ43 or Δ44, in particular a Δ8 or Δ42 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ8, Δ29, Δ42, Δ43 or Δ47 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ8, 429, Δ42 or Δ43 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In another variant of this embodiment, the truncated GAA polypeptide of the invention is a Δ8 or Δ42 truncated form of a hGAA polypeptide, and more particularly of the hGAA polypeptide shown in SEQ ID NO:1 or SEQ ID NO:33, in particular in SEQ ID NO:1, or of a functional variant thereof comprising amino acid substitutions in the sequence shown in SEQ ID NO:1 or SEQ ID NO:33, in particular in SEQ ID NO:1, and having at least 80, 85, 90, 95, 96, 97, 98 or 99 percent identity to SEQ ID NO:1 or SEQ ID NO:33, in particular in SEQ ID NO:1.

In a specific embodiment, the truncated hGAA polypeptide of the invention has an amino acid sequence consisting of the sequence shown in SEQ ID NO:27, SEQ ID NO:28, SEQ ID NO:34, SEQ ID NO:35 or SEQ ID NO:36, or a functional variant thereof comprising from 1 to 5 amino, in particular from 1 to 4, in particular from 1 to 3, more particularly from 1 to 2, in particular 1 amino acid substitution as compared to the sequence shown in SEQ ID NO:27, SEQ ID NO:28, SEQ ID NO:34, SEQ ID NO:35 or SEQ ID NO:36. In another specific embodiment, the truncated hGAA polypeptide of the invention has an amino acid sequence consisting of the sequence shown in SEQ ID NO:27, SEQ ID NO:28, SEQ ID NO:34 or SEQ ID NO:35, or a functional variant thereof comprising from 1 to 5 amino acid substitutions as compared to the sequence shown in SEQ ID NO:27, SEQ ID NO:28, SEQ ID NO:34 or SEQ ID NO:35. In a specific embodiment, the truncated hGAA polypeptide of the invention has an amino acid sequence consisting of the sequence shown in SEQ ID NO:27 or SEQ ID NO:28, or a functional variant thereof comprising from 1 to 5 amino, in particular from 1 to 4, in particular from 1 to 3, more particularly from 1 to 2, in particular 1 amino acid substitution as compared to the sequence shown in SEQ ID NO:27 or SEQ ID NO:28.

The truncated GAA polypeptide according to the invention may further comprise a signal peptide, such as the natural signal peptide of GAA, or an alternative signal peptide derived from another secreted protein. Non-limiting examples of such signal peptides include those shown in SEQ ID NO:3 to 7. The inventors have surprisingly shown that fusing the truncated GAA polypeptide of the invention to an alternative signal peptide even further enhances its secretion. The invention thereby provides a chimeric GAA polypeptide comprising a signal moiety and a truncated GAA polypeptide moiety, the truncated GAA polypeptide moiety being a truncated GAA polypeptide as defined above. In a particular embodiment, the signal peptide is the natural signal peptide of a GAA, such as the signal peptide of hGAA shown in SEQ ID NO:4. In another embodiment, the signal peptide is an exogenous (or alternative) signal peptide, derived from a protein different from GAA. In a particular embodiment, the alternative signal peptide is selected in the group consisting of SEQ ID NO:3, 5, 6 and 7, or a functional derivative thereof as defined below.

The inventors have shown that the exogenous signal peptide fused to the remainder of the GAA protein increases the secretion of the resulting chimeric GAA polypeptide as compared to the corresponding GAA polypeptide comprising its natural signal peptide. In addition, the truncated GAA polypeptide moiety also increases the secretion of the chimeric GAA polypeptide (including both a signal peptide and a truncated GAA polypeptide) as compared to a chimeric GAA polypeptide comprising the same signal peptide fused to the parent GAA polypeptide.

Particular exogenous signal peptides workable in the present invention include amino acids 1-20 from chymotrypsinogen B2 (SEQ ID NO:3), the signal peptide of human alpha-1-antitrypsin (SEQ ID NO:5), amino acids 1-25 from iduronate-2-sulphatase (SEQ ID NO:6), and amino acids 1-23 from protease C1 inhibitor (SEQ ID NO:7). The signal peptides of SEQ ID NO:3 and SEQ ID NO:5 to SEQ ID NO:7, allow higher secretion of the chimeric GAA protein both in vitro and in vivo when compared to the GAA comprising its natural signal peptide. In a particular embodiment, the signal peptide has the sequence shown in SEQ ID NO:3 to 7, or is a functional derivative thereof, i.e. a sequence comprising from 1 to 5, in particular from 1 to 4, in particular from 1 to 3, more particularly from 1 to 2, in particular 1 amino acid deletion (s), insertion(s) or substitution(s) as compared to the sequences shown in SEQ ID NO:3 to 7, as long as the resulting sequence corresponds to a functional signal peptide, i.e. a signal peptide that allows secretion of a GAA protein. In a particular embodiment, the signal peptide moiety sequence consists of a sequence selected in the group consisting of SEQ ID NO:3 to 7.

In particular embodiments, the GAA polypeptide of the invention is selected from:
the combination of SEQ ID NO:3 to a Δ8 truncated form of GAA, such as the Δ8 truncated form of hGAA represented in SEQ ID NO:27;
the combination of SEQ ID NO:4 to a Δ8 truncated form of GAA, such as the Δ8 truncated form of hGAA represented in SEQ ID NO:27;
the combination of SEQ ID NO:5 to a Δ48 truncated form of GAA, such as the Δ8 truncated form of hGAA represented in SEQ ID NO:27;
the combination of SEQ ID NO:6 to a Δ8 truncated form of GAA, such as the Δ8 truncated form of hGAA represented in SEQ ID NO:27;
the combination of SEQ ID NO:7 to a Δ8 truncated form of GAA, such as the Δ8 truncated form of hGAA represented in SEQ ID NO:27;
the combination of SEQ ID NO:3 to a Δ29 truncated form of GAA, such as the Δ29 truncated form of hGAA represented in SEQ ID NO:34;
the combination of SEQ ID NO:4 to a Δ29 truncated form of GAA, such as the Δ29 truncated form of hGAA represented in SEQ ID NO:34;
the combination of SEQ ID NO:5 to a Δ29 truncated form of GAA, such as the Δ29 truncated form of hGAA represented in SEQ ID NO:34;
the combination of SEQ ID NO:6 to a Δ29 truncated form of GAA, such as the Δ29 truncated form of hGAA represented in SEQ ID NO:34;
the combination of SEQ ID NO:7 to a Δ29 truncated form of GAA, such as the Δ29 truncated form of hGAA represented in SEQ ID NO:34;
the combination of SEQ ID NO:3 to a Δ42 truncated form of GAA, such as the Δ42 truncated form of hGAA represented in SEQ ID NO:28;
the combination of SEQ ID NO:4 to a Δ42 truncated form of GAA, such as the Δ42 truncated form of hGAA represented in SEQ ID NO:28;
the combination of SEQ ID NO:5 to a Δ42 truncated form of GAA, such as the Δ42 truncated form of hGAA represented in SEQ ID NO:28; the combination of SEQ ID NO:6 to a Δ42 truncated form of GAA, such as the Δ42 truncated form of hGAA represented in SEQ ID NO:28;
the combination of SEQ ID NO:7 to a Δ42 truncated form of GAA, such as the Δ42 truncated form of hGAA represented in SEQ ID NO:28;
the combination of SEQ ID NO:3 to a Δ43 truncated form of GAA, such as the Δ43 truncated form of hGAA represented in SEQ ID NO:35;
the combination of SEQ ID NO:4 to a Δ43 truncated form of GAA, such as the Δ43 truncated form of hGAA represented in SEQ ID NO:35;
the combination of SEQ ID NO:5 to a Δ43 truncated form of GAA, such as the Δ43 truncated form of hGAA represented in SEQ ID NO:35; the combination of SEQ ID NO:6 to a Δ43 truncated form of GAA, such as the Δ43 truncated form of hGAA represented in SEQ ID NO:35;
the combination of SEQ ID NO:7 to a Δ43 truncated form of GAA, such as the Δ43 truncated form of hGAA represented in SEQ ID NO:35;
the combination of SEQ ID NO:3 to a Δ47 truncated form of GAA, such as the Δ47 truncated form of hGAA represented in SEQ ID NO:36;
the combination of SEQ ID NO:4 to a Δ47 truncated form of GAA, such as the Δ47 truncated form of hGAA represented in SEQ ID NO:36;
the combination of SEQ ID NO:5 to a Δ47 truncated form of GAA, such as the Δ47 truncated form of hGAA represented in SEQ ID NO:36; the combination of SEQ ID NO:6 to a Δ47 truncated form of GAA, such as the Δ47 truncated form of hGAA represented in SEQ ID NO:36; and
the combination of SEQ ID NO:7 to a Δ47 truncated form of GAA, such as the Δ47 truncated form of hGAA represented in SEQ ID NO:36;
or is a functional derivative thereof having at least 90% identity, in particular at least 95%, at least 96%, at least 97%, at least 98%, or at least 99% identity to the resulting sequence combination. In these embodiments, as mentioned above, the signal peptide moiety may be a sequence comprising from 1 to 5, in particular from 1 to 4, in particular from 1 to 3, more particularly from 1 to 2, in particular 1 amino acid deletion(s), insertion(s) or substitution(s) as compared to the sequences shown in SEQ ID NO:3 to 7, as long as the resulting sequence corresponds to a functional signal peptide, i.e. a signal peptide that allows secretion of the resulting chimeric truncated GAA protein.

The relative proportion of newly-synthesized GAA that is secreted from the cell can be routinely determined by methods known in the art and as described in the examples. Secreted proteins can be detected by directly measuring the protein itself (e.g., by Western blot) or by protein activity assays (e.g., enzyme assays) in cell culture medium, serum, milk, etc.

Those skilled in the art will further understand that the truncated GAA polypeptide or the chimeric GAA polypeptide may contain additional amino acids, e.g., as a result of manipulations of the nucleic acid construct such as the addition of a restriction site, as long as these additional amino acids do not render the signal peptide or the GAA polypeptide non-functional. The additional amino acids can be cleaved or can be retained by the mature polypeptide as long as retention does not result in a non-functional polypeptide.

In another aspect, the invention relates to a nucleic acid molecule encoding the truncated GAA polypeptide of the invention or the chimeric GAA polypeptide of the invention.

The sequence of the nucleic acid molecule of the invention, encoding a truncated GAA, is optimized for expression of the GAA polypeptide in vivo. Sequence optimization may include a number of changes in a nucleic acid sequence, including codon optimization, increase of GC content, decrease of the number of CpG islands, decrease of the number of alternative open reading frames (ARFs) and decrease of the number of splice donor and splice acceptor sites. Because of the degeneracy of the genetic code, different nucleic acid molecules may encode the same protein. It is also well known that the genetic codes of different organisms are often biased towards using one of the several codons that encode the same amino acid over the others. Through codon optimization, changes are introduced in a nucleotide sequence that take advantage of the codon bias existing in a given cellular context so that the resulting codon optimized nucleotide sequence is more likely to be expressed in such given cellular context at a relatively high level compared to the non-codon optimised sequence. In a preferred embodiment of the invention, such sequence optimized nucleotide sequence encoding a truncated GAA is codon-optimized to improve its expression in human cells compared to non-codon optimized nucleotide sequences coding for the same truncated GAA protein, for example by taking advantage of the human specific codon usage bias.

In a particular embodiment, the optimized GAA coding sequence is codon optimized, and/or has an increased GC content and/or has a decreased number of alternative open reading frames, and/or has a decreased number of splice donor and/or splice acceptor sites, as compared to nucleotides 82-2859 of the wild-type hGAA coding sequence of SEQ ID NO:8. For example, nucleic acid sequence of the invention results in an at least 2, 3, 4, 5 or 10% increase of GC content in the GAA sequence as compared to the sequence of the wild-type GAA sequence. In a particular embodiment, the nucleic acid sequence of the invention results in a 2, 3, 4 or, more particularly, 5% or 10% (particularly 5%) increase of GC content in the GAA sequence as compared to the sequence of the wild-type GAA nucleotide sequence. In a particular embodiment, the nucleic acid sequence of the invention encoding a functional GAA polypeptide is "substantially identical", that is, about 70% identical, more preferably about 80% identical, even more preferably about 90% identical, even more preferably about 95% identical, even more preferably about 97%, 98% or even 99% identical to nucleotides 82-2859 of the sequence shown in SEQ ID NO: 8. As mentioned above, in addition to the GC content and/or number of ARFs, sequence optimization may also comprise a decrease in the number of CpG islands in the sequence and/or a decrease in the number of splice donor and acceptor sites. Of course, as is well known to those skilled in the art, sequence optimization is a balance between all these parameters, meaning that a sequence may be considered optimized if at least one of the above parameters is improved while one or more of the other parameters is not, as long as the optimized sequence leads to an improvement of the transgene, such as an improved expression and/or a decreased immune response to the transgene in vivo.

In addition, the adaptiveness of a nucleotide sequence encoding a functional GAA to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al, Gene. 1997, 199:293-301; zur Megede et al, Journal of Virology, 2000, 74: 2628-2635). Preferably, a nucleic acid molecule encoding a GAA has a CAI of at least 0.75 (in particular 0.77), 0.8, 0.85, 0.90, 0.92 or 0.94.

The term "nucleic acid sequence" (or nucleic acid molecule) refers to a DNA or RNA molecule in single or double stranded form, particularly a DNA encoding a GAA protein according to the invention.

The inventors have found that the above described truncated GAA polypeptide, when expressed from a nucleic acid molecule encoding the same, causes surprisingly high levels of expression of functional GAA protein both in vitro and in vivo compared to the wild-type GAA cDNA. Furthermore, as also shown by the inventors, the truncated GAA protein produced from liver and muscle cells expressing the nucleic acid molecule of the invention induces no immune response. This means that this nucleic acid molecule may be used to produce high levels of GAA protein, and provides therapeutic benefits such as avoiding to resort to immunosuppressive treatments, allowing low dose immunosuppressive treatment, and allowing repeated administration of the nucleic acid molecule of the invention to a subject in need thereof. Therefore, the truncated GAA polypeptide of the invention and the nucleic acid molecule of the invention are of special interest in contexts where GAA expression and/or activity is deficient or where high levels of expression of GAA can ameliorate a disease, such as for a glycogen storage disease. In a particular, the glycogen storage disease may be GSDI (von Gierke's disease), GSDII (Pompe disease), GSDIII (Cori disease), GSDIV, GSDV, GSDVI, GSDVII, GSDVIII or lethal congenital glycogen storage disease of the heart. More particularly, the glycogen storage disease is selected in the group consisting of GSDI, GSDII and GSDIII, even more particularly in the group consisting of GSDII and GSDIII. In an even more particular embodiment, the glycogen storage disease is GSDII. In particular, the nucleic acid molecules of the invention may be useful in gene therapy to treat GAA-deficient conditions or other conditions associated by accumulation of glycogen such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII. In an even more particular embodiment, the nucleic acid molecules of the invention may be useful in gene therapy to treat GSDII.

In another embodiment of the invention, the part of the nucleic acid molecule of the invention encoding the truncated GAA polypeptide moiety has at least 75 percent (such as 77.7%), or at least 80 percent or at least 82 percent (such as 83.1%) identity to the corresponding part of the nucleotide sequence encoding SEQ ID NO:1 or SEQ ID NO:33, in particular SEQ ID NO:1, which are sequences of wild-type hGAA polypeptides devoid of a signal peptide.

The truncated GAA moiety of the nucleic acid molecule of the invention preferably has at least 85 percent, more preferably at least 90 percent, and even more preferably at least 92 percent identity, in particular at least 95 percent identity, for example at least 98, 99 or 100 percent identity to the nucleotide sequence of SEQ ID NO: 10 or 11, which are sequence-optimized sequences.

The term "identical" and declinations thereof refers to the sequence identity between two nucleic acid molecules. When a position in both of the two compared sequences is occupied by the same base (e.g., if a position in each of two DNA molecules is occupied by adenine), then the molecules are identical at that position. The percent of identity between two sequences is a function of the number of matching positions shared by the two sequences divided by the number of positions compared×100. For example, if 6 of 10 of the positions in two sequences are matched then the two sequences are 60% identical. Generally, a comparison is made when two sequences are aligned to give maximum identity. Various bioinformatic tools known to the one skilled in the art might be used to align nucleic acid sequences such as BLAST or FASTA.

Furthermore, the nucleic acid molecule of the invention encodes a functional GAA protein, i.e. it encodes for a human GAA protein that, when expressed, has the functionality of wild-type GAA protein. As defined above, the functionality of wild-type GAA is to hydrolyse both α-1,4 and α-1,6 linkages of oligosaccharides and polysaccharides, more particularly of glycogen, to liberate glucose. The functional GAA protein encoded by the nucleic acid of the invention may have a hydrolysing activity on glycogen of at least 50%, 60%, 70%, 80%, 90%, 95%, 99%, or at least 100% as compared to the wild-type GAA protein of SEQ ID NO: 1, 2, 30 or 33. The activity of the GAA protein encoded by the nucleic acid of the invention may even be of more than 100%, such as of more than 110%, 120%, 130%, 140%, or even more than 150% of the activity of the wild-type GAA protein of SEQ ID NO:1, 2, 30 or 33.

A skilled person is readily able to determine whether a nucleic acid according to the invention expresses a functional GAA protein. Suitable methods would be apparent to those skilled in the art. For example, one suitable in vitro method involves inserting the nucleic acid into a vector, such as a plasmid or viral vector, transfecting or transducing host cells, such as 293T or HeLa cells, or other cells such as Huh7, with the vector, and assaying for GAA activity. Alternatively, a suitable in vivo method involves transducing a vector containing the nucleic acid into a mouse model of Pompe disease or another glycogen storage disorder and assaying for functional GAA in the plasma of the mouse and presence of GAA in tissues. Suitable methods are described in more details in the experimental part below.

In a particular embodiment, the nucleic acid molecule of the invention comprises the sequence shown in SEQ ID NO:12 or SEQ ID NO:13, encoding the polypeptide having the amino acid sequence shown in SEQ ID NO:27; the sequence shown in SEQ ID NO:48 or SEQ ID NO:49, encoding the polypeptide having the amino acid sequence shown in SEQ ID NO:28; the sequence shown in SEQ ID NO:50 or SEQ ID NO:51, encoding the polypeptide having the amino acid sequence shown in SEQ ID NO:35; or the sequence shown in SEQ ID NO:52 or SEQ ID NO:53, encoding the polypeptide having the amino acid sequence shown in SEQ ID NO:36. In a further embodiment, the nucleic acid molecule of the invention comprises the sequence shown in SEQ ID NO:12 or SEQ ID NO:13, encoding the polypeptide having the amino acid sequence shown in SEQ ID NO:27; the sequence shown in SEQ ID NO:48 or SEQ ID NO:49, encoding the polypeptide having the amino acid sequence shown in SEQ ID NO:28; or the sequence shown in SEQ ID NO:50 or SEQ ID NO:51, encoding the polypeptide having the amino acid sequence shown in SEQ ID NO:35. In a particular embodiment, the nucleic acid molecule of the invention comprises the sequence shown in SEQ ID NO:12 or SEQ ID NO:13, encoding the polypeptide having the amino acid sequence shown in SEQ ID NO:27.

The invention also relates to a nucleic acid construct comprising a nucleic acid molecule of the invention. The nucleic acid construct may correspond to an expression cassette comprising the nucleic acid sequence of the invention, operably linked to one or more expression control sequences and/or other sequences improving the expression of a transgene and/or sequences enhancing the secretion of the encoded protein and/or sequences enhancing the uptake of the encode protein. As used herein, the term "operably linked" refers to a linkage of polynucleotide elements in a functional relationship. A nucleic acid is "operably linked" when it is placed into a functional relationship with another nucleic acid sequence. For instance, a promoter, or another transcription regulatory sequence, is operably linked to a coding sequence if it affects the transcription of the coding sequence. Such expression control sequences are known in the art, such as promoters, enhancers (such as cis-regulatory modules (CRMs)), introns, polyA signals, etc.

In particular, the expression cassette may include a promoter. The promoter may be an ubiquitous or tissue-specific promoter, in particular a promoter able to promote expression in cells or tissues in which expression of GAA is desirable such as in cells or tissues in which GAA expression is desirable in GAA-deficient patients. In a particular embodiment, the promoter is a liver-specific promoter such as the alpha-1 antitrypsin promoter (hAAT) (SEQ ID NO:14), the transthyretin promoter, the albumin promoter, the thyroxine-binding globulin (TBG) promoter, the LSP promoter (comprising a thyroid hormone-binding globulin promoter sequence, two copies of an alpha1-microglobulin/ bikunin enhancer sequence, and a leader sequence—34.111, C. R., et al. (1997). Optimization of the human factor VIII complementary DNA expression plasmid for gene therapy of hemophilia A. Blood Coag. Fibrinol. 8: S23S30.), etc. Other useful liver-specific promoters are known in the art, for example those listed in the Liver Specific Gene Promoter Database compiled the Cold Spring Harbor Laboratory (see rulai.cshl.edu/LSPD/). A preferred promoter in the context of the invention is the hAAT promoter. In another embodiment, the promoter is a promoter directing expression in one tissue or cell of interest (such as in muscle cells), and in liver cells. For example, to some extent, promoters specific of muscle cells such as the desmin, Spc5-12 and MCK promoters may present some leakage of expression into liver cells, which can be advantageous to induce immune tolerance of the subject to the GAA polypeptide expressed from the nucleic acid of the invention.

Other tissue-specific or non-tissue-specific promoters may be useful in the practice of the invention. For example, the expression cassette may include a tissue-specific promoter which is a promoter different from a liver specific promoter. For example the promoter may be muscle-specific, such as the desmin promoter (and a desmin promoter variant such as a desmin promoter including natural or artificial enhancers), the SPc5-12 or the MCK promoter. In another embodiment, the promoter is a promoter specific of other cell lineage, such as the erythropoietin promoter, for the expression of the GAA polypeptide from cells of the erythroid lineage.

In another embodiment, the promoter is a ubiquitous promoter. Representative ubiquitous promoters include the cytomegalovirus enhancer/chicken beta actin (CAG) promoter, the cytomegalovirus enhancer/promoter (CMV), the PGK promoter, the SV40 early promoter, etc.

In addition, the promoter may also be an endogenous promoter such as the albumin promoter or the GAA promoter.

In a particular embodiment, the promoter is associated to an enhancer sequence, such as cis-regulatory modules (CRMs) or an artificial enhancer sequence. For example, the promoter may be associated to an enhancer sequence such as the human ApoE control region (or Human apolipoprotein E/C-I gene locus, hepatic control region HCR-1—Genbank accession No. U32510, shown in SEQ ID NO:15). In a particular embodiment, an enhancer sequence such as the ApoE sequence is associated to a liver-specific promoter such as those listed above, and in particular such as the hAAT promoter. Other CRMs useful in the practice of the present invention include those described in Rincon et al., Mol Ther. 2015 January; 23(1):43-52, Chuah et al., Mol Ther. 2014 September; 22(9):1605-13 or Nair et al., Blood. 2014 May 15; 123(20):3195-9.

In another particular embodiment, the nucleic acid construct comprises an intron, in particular an intron placed between the promoter and the GAA coding sequence. An intron may be introduced to increase mRNA stability and the production of the protein. In a further embodiment, the nucleic acid construct comprises a human beta globin b2 (or HBB2) intron, a coagulation factor IX (FIX) intron, a SV40 intron or a chicken beta-globin intron. In another further embodiment, the nucleic acid construct of the invention contains a modified intron (in particular a modified HBB2 or FIX intron) designed to decrease the number of, or even totally remove, alternative open reading frames (ARFs) found in said intron. Preferably, ARFs are removed whose length spans over 50 bp and have a stop codon in frame with a start codon. ARFs may be removed by modifying the sequence of the intron. For example, modification may be carried out by way of nucleotide substitution, insertion or deletion, preferably by nucleotide substitution. As an illustration, one or more nucleotides, in particular one nucleotide, in an ATG or GTG start codon present in the sequence of the intron of interest may be replaced resulting in a non-start codon. For example, an ATG or a GTG may be replaced by a CTG, which is not a start codon, within the sequence of the intron of interest.

The classical HBB2 intron used in nucleic acid constructs is shown in SEQ ID NO:16. For example, this HBB2 intron may be modified by eliminating start codons (ATG and GTG codons) within said intron. In a particular embodiment, the modified HBB2 intron comprised in the construct has the sequence shown in SEQ ID NO:17. The classical FIX intron used in nucleic acid constructs is derived from the first intron of human FIX and is shown in SEQ ID NO:18. FIX intron may be modified by eliminating start codons (ATG and GTG codons) within said intron. In a particular embodiment, the modified FIX intron comprised in the construct of the invention has the sequence shown in SEQ ID NO:19. The classical chicken-beta globin intron used in nucleic acid constructs is shown in SEQ ID NO:20. Chicken-beta globin intron may be modified by eliminating start codons (ATG and GTG codons) within said intron. In a particular embodiment, the modified chicken-beta globin intron comprised in the construct of the invention has the sequence shown in SEQ ID NO:21.

The inventors have previously shown in WO2015/162302 that such a modified intron, in particular a modified HBB2 or FIX intron, has advantageous properties and can significantly improve the expression of a transgene.

In a particular embodiment, the nucleic acid construct of the invention is an expression cassette comprising, in the 5' to 3' orientation, a promoter optionally preceded by an enhancer, the coding sequence of the invention (i.e. the optimized truncated GAA coding sequence of the invention, the chimeric GAA coding sequence of the invention, or the chimeric and sequence optimized GAA coding sequence of the invention), and a polyadenylation signal (such as the bovine growth hormone polyadenylation signal, the SV40 polyadenylation signal, or another naturally occurring or artificial polyadenylation signal). In a particular embodiment, the nucleic acid construct of the invention is an expression cassette comprising, in the 5' to 3' orientation, a promoter optionally preceded by an enhancer, (such as the ApoE control region), an intron (in particular an intron as defined above), the coding sequence of the invention, and a polyadenylation signal. In a further particular embodiment, the nucleic acid construct of the invention is an expression cassette comprising, in the 5' to 3' orientation, an enhancer such as the ApoE control region, a promoter, an intron (in particular an intron as defined above), the coding sequence of the invention, and a polyadenylation signal. In a further particular embodiment of the invention the expression cassette comprising, in the 5' to 3' orientation, an ApoE control region, the hAAT-liver specific promoter, a HBB2 intron (in particular a modified HBB2 intron as defined above), the coding sequence of the invention, and the bovine growth hormone polyadenylation signal, such as the construct shown in:

SEQ ID NO: 22, including a non-optimized nucleotide sequence encoding a Δ8 truncated form of GAA derived from the parent hGAA of SEQ ID NO:1 and encoding a signal peptide of SEQ ID NO:5;

SEQ ID NO:23, including an optimized sequence encoding a Δ8 truncated form of GAA derived from the parent hGAA of SEQ ID NO:1 (nucleotide sequence derived from the optimized sequence of SEQ ID NO:12) and encoding a signal peptide of SEQ ID NO:5;

SEQ ID NO: 24, including another optimized sequence encoding a Δ8 truncated form of GAA derived from the parent hGAA of SEQ ID NO:1 (nucleotide sequence derived from the optimized sequence of SEQ ID NO:13) and encoding a signal peptide of SEQ ID NO:5;

SEQ ID NO:25, including an optimized sequence encoding a Δ8 truncated form of GAA derived from the parent hGAA of SEQ ID NO:1 (nucleotide sequence derived from the optimized sequence of SEQ ID NO:12) and a signal peptide of SEQ ID NO:3;

SEQ ID NO:26, including an optimized sequence encoding a Δ42 truncated form of GAA derived from the parent hGAA of SEQ ID NO:1 (nucleotide sequence derived from the optimized sequence of SEQ ID NO:12) and a signal peptide of SEQ ID NO:3;

SEQ ID NO:37, including a non-optimized sequence encoding a Δ29 truncated form of GAA derived from the parent hGAA of SEQ ID NO:1 (nucleotide sequence derived from the non-optimized sequence of SEQ ID NO:9) and a signal peptide of SEQ ID NO:3;

SEQ ID NO:38, including an optimized sequence encoding a Δ29 truncated form of GAA derived from the parent hGAA of SEQ ID NO:1 (nucleotide sequence derived from the optimized sequence of SEQ ID NO:12) and a signal peptide of SEQ ID NO:3;

SEQ ID NO:39, including another optimized sequence encoding a Δ29 truncated form of GAA derived from the parent hGAA of SEQ ID NO:1 (nucleotide sequence derived from the optimized sequence of SEQ ID NO:13) and a signal peptide of SEQ ID NO:3;

SEQ ID NO:40: including a non-optimized sequence encoding a Δ42 truncated form of GAA derived from the parent hGAA of SEQ ID NO:1 (nucleotide sequence derived from the non-optimized sequence of SEQ ID NO:9) and a signal peptide of SEQ ID NO:3;

SEQ ID NO:41, including another optimized sequence encoding a Δ42 truncated form of GAA derived from the parent hGAA of SEQ ID NO:1 (nucleotide sequence derived from the optimized sequence of SEQ ID NO:13) and a signal peptide of SEQ ID NO:3;

SEQ ID NO:42, including a non-optimized sequence encoding a Δ43 truncated form of GAA derived from the parent hGAA of SEQ ID NO:1 (nucleotide sequence derived from the non-optimized sequence of SEQ ID NO:9) and a signal peptide of SEQ ID NO:3;

SEQ ID NO:43, including an optimized sequence encoding a Δ43 truncated form of GAA derived from the parent hGAA of SEQ ID NO:1 (nucleotide sequence derived from the optimized sequence of SEQ ID NO:12) and a signal peptide of SEQ ID NO:3;

SEQ ID NO:44, including another optimized sequence encoding a Δ43 truncated form of GAA derived from the parent hGAA of SEQ ID NO:1 (nucleotide sequence derived from the optimized sequence of SEQ ID NO:13) and a signal peptide of SEQ ID NO:3;

SEQ ID NO:45, including a non-optimized sequence encoding a Δ47 truncated form of GAA derived from the parent hGAA of SEQ ID NO:1 (nucleotide sequence derived from the non-optimized sequence of SEQ ID NO:9) and a signal peptide of SEQ ID NO:3;

SEQ ID NO:46, including an optimized sequence encoding a Δ47 truncated form of GAA derived from the parent hGAA of SEQ ID NO:1 (nucleotide sequence derived from the optimized sequence of SEQ ID NO:12) and a signal peptide of SEQ ID NO:3; and SEQ ID NO:47, including another optimized sequence encoding a Δ47 truncated form of GAA derived from the parent hGAA of SEQ ID NO:1 (nucleotide sequence derived from the optimized sequence of SEQ ID NO:13) and a signal peptide of SEQ ID NO:3.

Other expression cassettes of the invention may include the following nucleic acid sequences:

a non-optimized nucleotide sequence encoding a Δ8 truncated form of GAA derived from the parent hGAA of SEQ ID NO:1 and encoding a signal peptide of SEQ ID NO:4, 6 or 7;

a non-optimized nucleotide sequence encoding a Δ29 truncated form of GAA derived from the parent hGAA of SEQ ID NO:1 and encoding a signal peptide of SEQ ID NO:4, 6 or 7;

a non-optimized nucleotide sequence encoding a Δ42 truncated form of GAA derived from the parent hGAA of SEQ ID NO:1 and encoding a signal peptide of SEQ ID NO:4, 6 or 7;

a non-optimized nucleotide sequence encoding a Δ43 truncated form of GAA derived from the parent hGAA of SEQ ID NO:1 and encoding a signal peptide of SEQ ID NO:4, 6 or 7;

a non-optimized nucleotide sequence encoding a Δ47 truncated form of GAA derived from the parent hGAA of SEQ ID NO:1 and encoding a signal peptide of SEQ ID NO:4, 6 or 7;

an optimized nucleotide sequence encoding a Δ8 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ8 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ29 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ29 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ42 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ42 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ43 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ43 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ47 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ47 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7.

In alternative embodiments of these specific constructs, the sequence coding SEQ ID NO:1 is replaced by a sequence coding SEQ ID NO:33.

In a particular embodiment, the expression cassette comprises the ApoE control region, the hAAT-liver specific promoter, a codon-optimized HBB2 intron, the coding sequence of the invention and the bovine growth hormone polyadenylation signal.

In designing the nucleic acid construct of the invention, one skilled in the art will take care of respecting the size limit of the vector used for delivering said construct to a cell or organ. In particular, one skilled in the art knows that a major limitation of AAV vector is its cargo capacity which may vary from one AAV serotype to another but is thought to be limited to around the size of parental viral genome. For example, 5 kb, is the maximum size usually thought to be packaged into an AAV8 capsid (Wu Z. et aL, Mol Ther., 2010, 18(1): 80-86; Lai Y. et al., Mol Ther., 2010, 18(1): 75-79; Wang Y. et al., Hum Gene Ther Methods, 2012, 23(4): 225-33). Accordingly, those skilled in the art will take care in practicing the present invention to select the components of the nucleic acid construct of the invention so that the resulting nucleic acid sequence, including sequences coding AAV 5'- and 3'-ITRs to preferably not exceed 110% of the cargo capacity of the AAV vector implemented, in particular to preferably not exceed 5.5 kb.

The invention also relates to a vector comprising a nucleic acid molecule or construct as disclosed herein. In particular, the vector of the invention is a vector suitable for protein expression, preferably for use in gene therapy. In one embodiment, the vector is a plasmid vector. In another embodiment, the vector is a nanoparticle containing a nucleic acid molecule of the invention, in particular a messenger RNA encoding the GAA polypeptide of the invention. In another embodiment, the vector is a system based on transposons, allowing integration of the nucleic acid molecule or construct of the invention in the genome of the target cell, such as the hyperactive Sleeping Beauty (SB100X) transposon system (Mates et al. 2009). In another embodiment, the vector is a viral vector suitable for gene therapy, targeting any cell of interest such as liver tissue or cells, muscle cell, CNS cells (such as brain cells), or hematopoietic stem cells such as cells of the erythroid lineage (such as erythrocytes). In this case, the nucleic acid construct of the invention also contains sequences suitable for producing an efficient viral vector, as is well known in the art. In a particular embodiment, the viral vector is derived from an integrating virus. In particular, the viral vector may be derived from a retrovirus or a lentivirus. In a further particular embodiment, the viral vector is an AAV vector, such as an AAV vector suitable for transducing liver tissues or cells, more particularly an AAV-1, -2 and AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as -cy10 and -rh10, -rh74, -dj, Anc80, LK03, AAV2i8, porcine AAV serotypes such as AAVpo4 and AAVpo6, etc., vector or a retroviral vector such as a lentiviral vector and an alpha-retrovirus. As is known in the art, depending on the specific viral vector considered for use, additional suitable sequences will be introduced in the nucleic acid construct of the invention for obtaining a functional viral vector. Suitable sequences include AAV ITRs for an AAV vector, or LTRs for lentiviral vectors. As such, the invention also relates to an expression cassette as described above, flanked by an ITR or an LTR on each side.

Advantages of viral vectors are discussed in the following part of this disclosure. Viral vectors are preferred for delivering the nucleic acid molecule or construct of the invention, such as a retroviral vector, for example a lentiviral vector, or a non-pathogenic parvovirus, more preferably an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter).

Therefore, AAV vectors have arisen considerable interest as a potential vectors for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV-1, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as cy10 and -rh10, -rh74, -dj, Anc80, LK03, AAV2i8, porcine AAV serotypes such as AAVpo4 and AAVpo6, and tyrosine, lysine and serine capsid mutants of the AAV serotypes, etc. In addition, other non-natural engineered variants and chimeric AAV can also be useful.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells. Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

Accordingly, the present invention relates to an AAV vector comprising the nucleic acid molecule or construct of the invention. In the context of the present invention, the AAV vector comprises an AAV capsid able to transduce the target cells of interest, in particular hepatocytes. According to a particular embodiment, the AAV vector is of the AAV-1, -2, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as -cy10 and -rh10, -rh74, -dj, Anc80, LK03, AAV2i8, porcine AAV such as AAVpo4 and AAVpo6, and tyrosine, lysine and serine capsid mutants of a AAV serotypes, etc., serotype. In a particular embodiment, the AAV vector is of the AAV8, AAV9, AAVrh74 or AAV2i8 serotype (i.e. the AAV vector has a capsid of the AAV8, AAV9, AAVrh74 or AAV2i8 serotype). In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype. For example, the genome of the pseudotyped vector may have a capsid derived from the AAV8, AAV9, AAVrh74 or AAV2i8 serotype, and its genome may be derived from and different serotype. In a particular embodiment, the AAV vector has a capsid of the AAV8, AAV9 or AAVrh74 serotype, in particular of the AAV8 or AAV9 serotype, more particularly of the AAV8 serotype.

In a specific embodiment, wherein the vector is for use in delivering the transgene to muscle cells, the AAV vector may be selected, among others, in the group consisting of AAV8, AAV9 and AAVrh74. In another specific embodiment, wherein the vector is for use in delivering the transgene to liver cells, the AAV vector may be selected, among others, in the group consisting of AAV5, AAV8, AAV9, AAV-LK03, AAV-Anc80 and AAV3B.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example a chimeric AAV vector can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In addition, capsid variants may include single amino acid changes such as tyrosine mutants (e.g. as described in Zhong et al., 2008).

In addition, the genome of the AAV vector may either be a single stranded or self-complementary double-stranded genome (McCarty et al., Gene Therapy, 2003). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid.

In a particularly preferred embodiment, the invention relates to an AAV vector comprising, in a single-stranded or double-stranded, self-complementary genome (e.g. a single-stranded genome), the nucleic acid construct of the invention. In one embodiment, the AAV vector comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid. In a further particular embodiment, said nucleic acid is operably linked to a promoter, especially a ubiquitous or liver-specific promoter. According to a specific variant embodiment, the promoter is a ubiquitous promoter such as the cytomegalovirus enhancer/chicken beta actin (CAG) promoter, the cytomegalovirus enhancer/promoter (CMV), the PGK promoter and the SV40 early promoter. In a specific variant, the ubiquitous promoter is the CAG promoter. According to another variant, the promoter is a liver-specific promoter such as the alpha-1 antitrypsin promoter (hAAT), the transthyretin promoter, the albumin promoter and the thyroxine-binding globulin (TBG) promoter. In a specific variant, the liver-specific promoter is the hAAT liver-specific promoter of SEQ ID NO:14. In a further particular embodiment, the nucleic acid construct comprised into the genome of the AAV vector of the invention further comprises an intron as described above, such as an intron placed between the promoter and the nucleic acid sequence encoding the GAA coding sequence (i.e. the optimized GAA coding sequence of the invention, the chimeric GAA coding sequence of the invention, or the chimeric and optimized GAA coding sequence of the invention). Representative introns that may be included within the nucleic acid construct introduced within the AAV vector genome include, without limitation, the human beta globin b2 (or HBB2) intron, the FIX intron and the chicken beta-globin intron. Said intron within the genome of the AAV vector may be a classical (or unmodified) intron or a modified intron designed to decrease the number of, or even totally remove, alternative open reading frames (ARFs) within said intron. Modified and unmodified introns that may be used in the practice of this embodiment where the nucleic acid of the invention is introduced within an AAV vector are thoroughly described above. In a particular embodiment, the AAV vector, in particular an AAV vector comprising an AAV8, AAV9, AAVrh74 or AAV2i8 capsid, in particular an AAV8, AAV9 or AAVrh74 capsid, such as an AAV8 or AAV9 capsid, more particularly an AAV8 capsid, of the invention includes within its genome a modified (or optimized) intron such as the modified HBB2 intron of SEQ ID NO:17, the modified FIX intron of SEQ ID NO:19 and the modified chicken beta-globin intron of SEQ ID NO:21. In a further particular embodiment, the vector of the invention is an AAV vector comprising comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid, comprising a genome containing, in the 5' to 3' orientation: an AAV 5'-ITR (such as an AAV2 5'-ITR); an ApoE control region; the hAAT-liver specific promoter; a HBB2 intron (in particular a modified HBB2 intron as defined above); the GAA coding sequence of the invention; the bovine growth hormone polyadenylation signal; and an AAV 3'-ITR (such as an AAV2 3'-ITR), such as a genome comprising a the nucleic acid construct shown in SEQ ID NO:22 to 26 and SEQ ID NO:37 to 47 flanked by an AAV 5'-ITR (such as an AAV2 5'-ITR) and an AAV 3'-ITR (such as an AAV2 3'-ITR). Other nucleic acid constructs useful in the practice of the present invention comprise those described above, including:

a non-optimized nucleotide sequence encoding a Δ8 truncated form of GAA derived from the parent hGAA of SEQ ID NO:1 and encoding a signal peptide of SEQ ID NO:4, 6 or 7;

a non-optimized nucleotide sequence encoding a Δ29 truncated form of GAA derived from the parent hGAA of SEQ ID NO:1 and encoding a signal peptide of SEQ ID NO:4, 6 or 7;

a non-optimized nucleotide sequence encoding a Δ42 truncated form of GAA derived from the parent hGAA of SEQ ID NO:1 and encoding a signal peptide of SEQ ID NO:4, 6 or 7;

a non-optimized nucleotide sequence encoding a Δ43 truncated form of GAA derived from the parent hGAA of SEQ ID NO:1 and encoding a signal peptide of SEQ ID NO:4, 6 or 7;

a non-optimized nucleotide sequence encoding a Δ47 truncated form of GAA derived from the parent hGAA of SEQ ID NO:1 and encoding a signal peptide of SEQ ID NO:4, 6 or 7;

an optimized nucleotide sequence encoding a Δ8 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ8 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ29 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ29 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ42 truncated form of GAA derived from the parent hGAA of SEQ ID NO:1 (nucleotide sequence derived from the optimized sequence of SEQ ID NO:12) and encoding a signal peptide of SEQ ID NO:4 or 6;

an optimized nucleotide sequence encoding a Δ42 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ43 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ43 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7;

an optimized nucleotide sequence encoding a Δ47 truncated form of GAA derived from the parent hGAA of SEQ ID NO:1 (nucleotide sequence derived from the optimized sequence of SEQ ID NO:12) and encoding a signal peptide of SEQ ID NO:4, 6 or 7;

an optimized nucleotide sequence encoding a Δ47 truncated form of GAA derived from the parent hGAA of SEQ ID NO:1 (nucleotide sequence derived from the optimized sequence of SEQ ID NO:13) and encoding a signal peptide of SEQ ID NO:4, 6 or 7.

In alternative embodiments of these specific constructs, the sequence coding SEQ ID NO:1 is replaced by a sequence coding SEQ ID NO:33.

In a particular embodiment of the invention, the nucleic acid construct of the invention comprises a liver-specific promoter as described above, and the vector is a viral vector capable of transducing liver tissue or cells as described above. The inventors present below data showing that the protolerogenic and metabolic properties of the liver are advantageously implemented thanks to this embodiment to develop highly efficient and optimized vectors to express highly secretable forms of GAA in hepatocytes and to induce immune tolerance to the protein.

In addition, in a further particular embodiment, the invention provides the combination of two vectors, such as two viral vectors, in particular two AAV vectors, for improving gene delivery and treatment efficacy in the cells of interest. For example, the two vectors may carry the nucleic acid molecule of the invention coding for the GAA protein of the invention, under the control of one different promoter in each of these two vectors. In a particular embodiment, one vector comprises a promoter which is a liver-specific promoter (as one of those described above), and the other vector comprises a promoter which is specific of another tissue of interest for the treatment of a glycogen storage disorder, such as a muscle-specific promoter, for example the desmin promoter. In a particular variant of this embodiment, this combination of vectors corresponds to multiple co-packaged AAV vectors produced as described in WO2015196179.

The invention also relates to a cell, for example a liver cell, that is transformed with a nucleic acid molecule or construct of the invention as is the case for ex vivo gene therapy. Cells of the invention may be delivered to the subject in need thereof, such as GAA-deficient patient, by any appropriate administration route such as via injection in the liver or in the bloodstream of said subject. In a particular embodiment, the invention involves introducing the nucleic acid molecule, the nucleic acid construct or the vector, particularly a lentiviral vector, of the invention into liver cells, in particular into liver cells of the subject to be treated, and administering said transformed liver cells into which the nucleic acid has been introduced to the subject. Advantageously, this embodiment is useful for secreting GAA from said cells. In a particular embodiment, the liver cells are liver cells from the patient to be treated, or are liver stem cells that are further transformed, and differentiated in vitro into liver cells, for subsequent administration to the patient.

The present invention further relates to a transgenic, nonhuman animal comprising in its genome the nucleic acid molecule or construct encoding a GAA polypeptide according to the invention. In a particular embodiment, the animal is a mouse.

Apart from the specific delivery systems embodied below in the examples, various delivery systems are known and can be used to administer the nucleic acid molecule or construct of the invention, e.g., encapsulation in liposomes, microparticles, microcapsules, recombinant cells capable of expressing the coding sequence of the invention, receptor-mediated endocytosis, construction of a therapeutic nucleic acid as part of a retroviral or other vector, etc.

According to an embodiment, it may be desirable to introduce the GAA polypeptide, nucleic acid molecule, nucleic acid construct or cell of the invention into the liver of the subject by any suitable route. In addition naked DNA such as minicircles and transposons can be used for delivery or lentiviral vectors. Additionally, gene editing technologies such as zinc finger nucleases, meganucleases, TALENs, and CRISPR can also be used to deliver the coding sequence of the invention.

The present invention also provides pharmaceutical compositions comprising the nucleic acid molecule, the nucleic acid construct, the vector, the GAA polypeptide, or the cell of the invention. Such compositions comprise a therapeutically effective amount of the therapeutic (the nucleic acid molecule, the nucleic acid construct, the vector, the GAA polypeptide or the cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid, vector or cell of the invention is formulated in a composition comprising phosphate-buffered saline and supplemented with 0.25% human serum albumin. In another particular embodiment, the nucleic acid, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

In an embodiment, the nucleic acid molecule, the nucleic acid construct, the vector, the GAA polypeptide or the cell of the invention can be delivered in a vesicle, in particular a liposome. In yet another embodiment, the nucleic acid molecule, the nucleic acid construct, the vector, the GAA polypeptide or the cell of the invention can be delivered in a controlled release system.

Methods of administration of the nucleic acid molecule, the nucleic acid construct, the vector, the GAA polypeptide or the cell of the invention include but are not limited to intradermal, intramuscular, intraperitoneal, intravenous, subcutaneous, intranasal, epidural, and oral routes. In a particular embodiment, the administration is via the intravenous or intramuscular route. The nucleic acid molecule, the nucleic acid construct, the vector, the GAA polypeptide or the cell of the invention, whether vectorized or not, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment, e.g. the liver. This may be achieved, for example, by means of an implant, said implant being of a porous, nonporous, or gelatinous material, including membranes, such as sialastic membranes, or fibers.

The amount of the therapeutic (i.e. the nucleic acid molecule, the nucleic acid construct, the vector, the GAA polypeptide or the cell of the invention) of the invention which will be effective in the treatment of a glycogen storage disease can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the nucleic acid molecule, the nucleic acid construct, the vector, the GAA polypeptide or the cell of the invention administered to the subject in need thereof will vary based on several factors including, without limitation, the route of administration, the specific disease treated, the subject's age or the level of expression necessary to achieve the therapeutic effect. One skilled in the art can readily determine, based on its knowledge in this field, the dosage range required based on these factors and others. In case of a treatment comprising administering a viral vector, such as an AAV vector, to the subject, typical doses of the vector are of at least $1\times10^8$ vector genomes per kilogram body weight (vg/kg), such as at least $1\times10^9$ vg/kg, at least $1\times10^{10}$ vg/kg, at least $1\times10^{11}$ vg/kg, at least $1\times10^{12}$ vg/kg at least $1\times10^{13}$ vg/kg, or at least $1\times10^{14}$ vg/kg.

The invention also relates to a method for treating a glycogen storage disease, which comprises a step of delivering a therapeutic effective amount of the nucleic acid, the vector, the GAA polypeptide, the pharmaceutical composition or the cell of the invention to a subject in need thereof.

The invention also relates to a method for treating a glycogen storage disease, said method inducing no immune response to the transgene (i.e. to the GAA polypeptide of the invention), or inducing a reduced immune response to the transgene, comprising a step of delivering a therapeutic effective amount of the nucleic acid molecule, nucleic acid construct, vector, pharmaceutical composition or cell of the invention to a subject in need thereof. The invention also relates to a method for treating a glycogen storage disease, said method comprising repeated administration of a therapeutic effective amount of the nucleic acid molecule, nucleic acid construct, vector, pharmaceutical composition or cell of the invention to a subject in need thereof. In this aspect, the nucleic acid molecule or the nucleic acid construct of the invention comprises a promoter which is functional in liver cells, thereby allowing immune tolerance to the expressed GAA polypeptide produced therefrom. As well, in this aspect, the pharmaceutical composition used in this aspect comprises a nucleic acid molecule or nucleic acid construct comprising a promoter which is functional in liver cells. In case of delivery of liver cells, said cells may be cells previously collected from the subject in need of the treatment and that were engineered by introducing therein the nucleic acid molecule or the nucleic acid construct of the invention to thereby make them able to produce the GAA polypeptide of the invention. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a viral vector of the invention is done using a different virus for each successive administration, thereby avoiding a reduction of efficacy because of a possible immune response against a previously administered viral vector. For example, a first administration of a viral vector comprising an AAV8 capsid may be done, followed by the administration of a vector comprising an AAV9 capsid, or even by the administration of a virus unrelated to AAVs, such as a retroviral or lentiviral vector.

According to the present invention, a treatment may include curative, alleviation or prophylactic effects. Accordingly, therapeutic and prophylactic treatment includes amelioration of the symptoms of a particular glycogen storage disease or preventing or otherwise reducing the risk of developing a particular glycogen storage disease. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition. The term 'treatment' is used herein to refer to any regimen that can benefit an animal, in particular a mammal, more particularly a human subject.

The invention also relates to an ex vivo gene therapy method for the treatment of a glycogen storage disease comprising introducing the nucleic acid molecule or the nucleic acid construct of the invention into an isolated cell of a patient in need thereof, for example an isolated hematopoietic stem cell, and introducing said cell into said patient in need thereof. In a particular embodiment of this aspect, the nucleic acid molecule or construct is introduced into the cell with a vector as defined above. In a particular embodiment, the vector is an integrative viral vector. In a further particular embodiment, the viral vector is a retroviral vector, such as a lenviral vector. For example, a lentiviral vector as disclosed in van Til et al., 2010, Blood, 115(26), p. 5329, may be used in the practice in the method of the present invention.

The invention also relates to the nucleic acid molecule, the nucleic acid construct, the vector, the GAA polypeptide or the cell of the invention for use as a medicament.

The invention also relates to the nucleic acid molecule, the nucleic acid construct, the vector, the GAA polypeptide or the cell of the invention, for use in a method for treating a disease caused by a mutation in the GAA gene, in particular in a method for treating Pompe disease. The invention further relates to the nucleic acid molecule, the nucleic acid construct, the vector, the GAA polypeptide or the cell of the invention, for use in a method for treating a glycogen storage disease such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII. The truncated GAA polypeptide of the invention may be administered to a patient in need thereof, for use in enzyme replacement therapy (ERT), such as for use in enzyme replacement therapy a glycogen storage disease, such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII.

The invention further relates to the use of the nucleic acid molecule, the nucleic acid construct, the vector, the GAA polypeptide or the cell of the invention, in the manufacture of a medicament useful for treating a glycogen storage disease, such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII.

EXAMPLES

The invention is further described in detail by reference to the following experimental examples and the attached figures. These examples are provided for purposes of illustration only, and are not intended to be limiting.

Material and Methods

GAA Activity

GAA activity was measured following homogenization of frozen tissue samples in distilled water. 50-100 mg of tissue were weighed and homogenized, then centrifuged for 20 minutes at 10000×g. The reaction was set up with 10 µl of supernatant and 20 µl of substrate—4MUα-D-glucoside, in a 96 wells plate. The reaction mixture was incubated at 37° C. for one hour, and then stopped by adding 150 µl of Sodium Carbonate buffer pH 10.5. A standard curve (0-2500 pmol/µl of 4MU) was used to measure released fluorescent 4MU from individual reaction mixture, using the EnSpire alpha plate reader (Perkin-Elmer) at 449 nm (Emission) and 360 nm (Excitation). The protein concentration of the clarified supernatant was quantified by BCA (Thermo Fisher Scientific). To calculate the GAA activity, released 4MU concentration was divided by the sample protein concentration and activity was reported as nmol/hour/mg protein.

Mouse Studies

Gaa −/− mouse was generated by targeted disruption of exon 6 and is maintained on the C57BL/6J/129X1/SvJ background (Raben N. et al 1998). Vectors were delivered via the tail vein in a volume of 0.2 ml. Serum samples were collected monthly to monitor levels of secreted hGAA. PBS-injected affected animals and wild type littermates were used as controls.

NHP Study

Male Cynomolgus macaques were housed in stainless steel cages and maintained on a 12-hour light/dark cycle. All macaques had neutralizing antibody titers of <1:5 before the start of the study. A dose of 2E12 vg/kg of AAV8-hAAT-sp7-Δ8-hGAAco1 was infused via the saphenous vein. Blood samples were taken 12 days before and 30 days after the injection via the femoral vein. Whole blood was collected in EDTA containing tubes and centrifuged to separate serum. Three months after vector administration all macaques were euthanized. The animals were first anesthetized with a mixture of ketamine/dexmedetomidine and then euthanized using sodium pentobarbital injected IV. Tissues were immediately collected and frozen in liquid nitrogen.

Western Blot Analysis

Total homogenates were obtained from frozen muscles. Protein concentration was determined in the extracts by Pierce BCA Protein Assay (Thermo Fisher Scientific), following manufacturer's instructions. Western blot was performed with an anti hGAA antibody (Abcam). Anti-tubulin antibody (Sigma Aldrich) was used as loading controls.

Results

With the aim of designing new forms of GAA with improved secretion and reduced immunogenicity, we decided to produce truncated forms of GAA, optionally combining them with alternative signal peptides.

The human GAA shown in SEQ ID NO:2 served has the basis for designing these new forms. SEQ ID NO:1 corresponds to the sequence of SEQ ID NO:2, devoid of the corresponding natural signal peptide of GAA (amino acids 1-27 of SEQ ID NO:2). Nucleic acid constructs were designed to encode GAA polypeptides derived from SEQ ID NO:1 truncated at its N-terminal end. We started by designing a nucleic acid sequence based on the wild-type hGAA coding sequence (SEQ ID NO:9, corresponding to nucleotides 82-2859 of SEQ ID NO:8 that is the wild-type hGAA coding sequence including the signal peptide coding sequence) deleted for the codons corresponding to the first 8 amino acids of SEQ ID NO:1 (66 8). In addition to the wild-type hGAA coding sequence, we designed optimized nucleic acid sequence encoding the Δ8 truncated hGAA polypeptide (SEQ ID NO:10 and SEQ ID NO:11 corresponds to the hGAAco1 and hGAAco2 optimized coding sequence, respectively), to exclude a possible sequence-specific effect.

TABLE 1

Description of the optimized sequences. Table illustrating the characteristics of the two hGAA optimized sequences compared to the wild-type one.

| sequence | WT | co1 | co2 |
|---|---|---|---|
| CAI[a] | 0.84 | 0.94 | 0.77 |
| GC content[b] | 64.7 | 61.9 | 54.4 |
| aORF 5'→3'[c] | 2 | 3 | 0 |
| aORF 3'→5'[d] | 5 | 4 | 0 |
| SA[e] | 3 | 0 | 1 |
| SD[f] | 3 | 0 | 0 |
| % identity vs wt[g] | | 83.1 | 77.7 |
| % identity vs co1[h] | | | 80.8 |
| CpG islands[i] | 4 | 5 | 1 |

[a]codon adaptation index and
[b]GC content calculated using a rare codon analysis tool (see Worldwide Website: genscript.com).
[c]and [d]are respectively the alternative open reading frames calculated on the 5' to 3' (aORF 5'→3') and 3' to 5' (aORF 3'→5') strands.
[e]and [f]are respectively the acceptor (SA) and donor (SD) splicing sites calculated using a splicing site online prediction tool (see Worldwide Website: fruitfly.org/seq_tools/splice.html).
[g]and [h]are respectively the percentual identity calculated versus wild-type (wt) and optimized co1 sequence.
[i]CpG islands calculated using MethDB online tool (see Worldwide Website: methdb.de/links.html). CpG islands are sequences longer than 100 bp, with GC content > 60% and an observed/expected ratio > 0.6.

Amino acids 1-27 of the hGAAs sequences (corresponding to the natural signal peptide of hGAA, here defined as sp1; whose sequence is shown in SEQ ID NO:4) have been replaced by amino acids 1-24 of the sequence of the human alpha-1-antitrypsin (NP_000286.3) here defined as sp2 (sequence shown in SEQ ID NO:5). We transfected truncated hGAA coding constructs in parallel with their full-size versions in human hepatoma cells (Huh-7) and we measured the quantity of hGAA released in the medium 48 hours after (FIG. 1A). The Δ8 deletion of hGAAs sequences led to a significant, 50% increase in the secretion level both for wild-type (hGAA) and codon optimized (hGAAco2) sequences. The same truncation performed on a different codon optimized sequence (hGAAco1) also improved the secretion of hGAA to the same extent.

To confirm that a change in the sequence following signal peptide may improve the secretion of hGAA, we further truncated the hGAA polypeptide. We eliminated the codons corresponding to the first 42 amino acids of hGAA from the hGAAco1 construct (Δ42) and we replaced them with a signal peptide derived from chymotrypsinogen B1 (sp7; sequence shown in SEQ ID NO:3). We then compared the efficacy of secretion obtained with this new deleted construct with its Δ8 version fused with sp7 signal peptide and the full size hGAAco1 with sp1 or with sp7. We transfected those constructs in Huh-7 cells and we measured the activity of hGAA in the medium 48 hours after. As expected, we could measure hGAA activity after the transfection of a full size hGAAco1 (p=0.055 vs GFP) and its secretion is twofold increased by substituting the wild-type signal peptide with the sp7 (p=0.006 vs hGAAco1). Surprisingly, both the 66 8 and the Δ42 hGAA sequences fused with the sp7 signal peptide shown a two-fold increase in the secreted hGAA compared to the full-size sequence (p=0.0002 and 0.0003 respectively vs sp7-hGAAco1, FIG. 1B).

Taken together, these data demonstrate that the truncation of hGAA sequence coupled with an efficient signal peptide is able to increase the secretion of the protein in vitro. Additionally, the truncation has one important advantage compared to the mutagenesis of the native sequence as it does not create major neo-antigens, which is an advantage in the engineering of a therapeutic product.

We then verified those findings in vivo, in a Pompe disease mouse model. We injected GAA −/− mice (Raben et al J. Bio. Chem. 1998) with AAV8 vectors expressing hGAAco1 full size, Δ8, or Δ42 fused with sp7 signal peptide under the transcriptional control of a highly potent liver specific promoter derived from the fusion of the apolipoprotein B enhancer and the human alpha-1-antitrypsin promoter (hAAT). One month after the injection of 2E12 vg/kg of the vectors described above, mice were bled and the activity of hGAA was measured in serum. The treatment of mice with vectors expressing the full-length hGAAco1 fused with sp7 shown an increased level of hGAA in the bloodstream (p=0.115 vs PBS). Surprisingly, both the truncated hGAA, Δ8 and Δ42, led to a significant increase in the level of hGAA in serum (p=0.014 and 0.013 respectively).

These data indicate that the deletion of the first amino acids of the hGAA lead to a significant improvement in the level of hGAA secreted in the bloodstream.

Furthermore, another signal peptide was fused to the Δ8 truncated form of hGAA, corresponding to amino acids 1-25 from iduronate-2-sulphatase (sp6; SEQ ID NO:6). We transfected hepatoma cells (Huh-7) with plasmids expressing GFP or wild-type hGAA (hGAA; parent polypeptide corresponding to amino acid residues 28-952 of SEQ ID NO:30) in parallel with plasmids expressing optimized hGAA (hGAAco1) fused with sp1, sp2, sp6, sp7 or sp8. 48 hours after transfection the growth medium has been analyzed for the presence of hGAA. Notably these constructs led to the secretion of hGAA levels significantly higher than what observed in the negative control represented by GFP-transfected cells (FIG. 3).

We then evaluated glycogen content in heart, diaphragm and quadriceps of GAA −/− mice treated as described above with a Δ8-hGAA. Notably, we observed high levels of hGAA in the tissues after treatment with Δ8-hGAAco expressing vectors (data not shown) that correlated with a significant reduction in glycogen content in all the tissues considered (FIG. 4B-D). In particular, in the heart (FIG. 4B) the level of glycogen measured after treatment with vectors bearing the high efficient signal peptides sp7 and 8 were undistinguishable from those observed in non-affected animals (p=0.983 and 0.996 vs WT respectively). Importantly the level observed after treatment with both the sp7 and sp8 vectors were significantly reduced compared to GAA −/− animals PBS-injected or treated with hGAAco expressing vector fused with sp1 signal peptide.

We also tested if the liver transduction with our vectors induced a humoral response against the transgene. Mice were injected intravenously with AAV8 vectors expressing hGAAco1 with native sp1 signal peptide (co) or Δ8-hGAAco1 fused with sp2, sp7, or sp8 under the transcriptional control of a liver specific promoter. The results are presented in FIG. 5. Gaa−/− injected intramuscularly with an AAV expressing Δ8-hGAAco1 under the transcriptional control of a constitutive promoter showed very high level of total IgG (~150 µg/mL), whereas in general vector expressing the same protein in the liver showed lower level of humoral response. Interestingly, mice injected with sp1 hGAAco1 (co) expressing vector showed detectable level of antibodies at both doses, whereas mice injected with the engineered high secreted vectors had undetectable IgG levels. These data indicate that the expression of a transgene in the liver is fundamental for the induction of peripheral tolerance, also they provide indications that high circulating levels of a hGAA, achieved by the fusion with an efficient signal peptide induce a reduction in the humoral response against the protein itself.

The best performing vector selected in the mouse study was injected in two non-human primates (NHP, *Macaca Fascicularis* sp.) to verify the efficacy of secretion of our vector and the uptake in muscles. We injected two monkeys with 2E12 vg/kg of AAV8-hAAT-sp7-Δ8-hGAAco1. One month after the injection we measured the levels of hGAA in the serum of the two animals by western blot using a specific anti-hGAA antibody. We observed a clear band with a size compatible with that of hGAA in the two monkeys. This band was not present in serum samples obtained 12 days before vector injection, thus confirming the specificity of our detection method (FIG. 6A). Three months after the injection we sacrificed the animals and we obtained tissues to verify if hGAA secreted from the liver in the bloodstream were efficiently taken up by muscle. We performed a western blot using an antibody specific for hGAA on total lysates obtained from biceps and diaphragm of the two monkeys. Interestingly we were able to observe a clear band in animal number 2 which also showed the highest levels of hGAA in the bloodstream (FIG. 6B). Also, in animal number 1 we could observe a fainter band with a molecular weight consistent with that of hGAA in both muscles analyzed. These data indicate that the AAV8-hAAT-sp7-Δ8-hGAAco1 vector efficiently transduces liver in NHP. They also demonstrate that the protein secreted in the bloodstream is efficiently taken up in muscle and that this uptake is correlated with the level of hGAA measured in blood.

We also determined the effect of the best performing vector selected in the mouse study (AAV8-hAAT-sp7-Δ8-hGAAco1) in a mouse model of GSDIII. We developed a knock-out mouse model for the glycogen debranching enzyme (GDE). This model recapitulates the phenotype of the disease observed in humans affected by type III glycogen storage disease (GSDIII). In particular GDE −/− mice, that completely lacks the GDE activity, have an impairment in muscle strength and accumulate glycogen in different tissues. Interestingly they also accumulate glycogen in the liver, which also is seen in humans. Here we tested if the overexpression of sp7-Δ8-hGAA in the liver rescue the glycogen accumulation observed in GDE −/− mice. We injected GDE−/− mice with 1E11 or 1E12 vg/mouse of AAV8-hAAT-sp7-Δ8-hGAAco1. As controls, we injected in parallel wild-type (WT) and GDE −/− mice with PBS. Three months after the vector administration, mice were sacrificed and the level of glycogen in the liver has been quantified. The results are reported in FIG. 7. As already reported (Pagliarani et al. and our model), GDE −/− mice shown a significant increase in glycogen accumulation in the liver (p=1.3E−7) with 5 times more glycogen when compared to wild-type animals. Surprisingly, the treatment with 1E11 and 1E12 vg/mouse of the AAV8-hAAT-sp7-Δ8-hGAAco1 vector induced a statistically significant decrease in the glycogen content (p=4.5E−5 and 1.4E−6 respectively).

Importantly, the levels of glycogen measured in the liver of mice injected with AAV8-hAAT-sp7-Δ8-hGAAco1 vector were undistinguishable from those measured in wild-type animals in particular at the highest dose (p=0.053 for the 1E11 dose cohort and 0.244 for the 1E12 dose cohort).

We performed the analysis of GAA activity in media and lysates of HuH7 cells transfected with different GAA versions (all codon-optimized): 1. native GAA including the native sp1 GAA signal peptide (co), 2. engineered GAA containing the heterologous sp7 signal peptide (sp7-co), and 3. engineered GAA containing the heterologous sp7 signal peptide followed by the deletion of a variable number of amino-acids (sp7-Δ8-co, sp7-Δ29-co, sp7-Δ42-co, sp7-Δ43-co, sp7-Δ47-co and sp7-Δ62-co, wherein the 8, 29, 42, 47 and 62 first N-terminal amino acids of SEQ ID NO:1 are deleted, respectively). The analysis showed (FIG. 8) significantly higher GAA activity in media of cells transfected with Δ8, Δ29, Δ42 and Δ43 GAA versions compared to both engineered non-deleted GAA (sp7-co) and native GAA (co). Significantly lower GAA activity was instead observed in media of cells transfected with Δ47 and Δ62 GAA versions compared to the other engineered GAA versions [deleted (sp7-Δ8-co, sp7-Δ29-co, sp7-Δ42-co, sp7-Δ43-co) and non-deleted (sp7-co)]. Interestingly, (FIG. 9) intracellular GAA activity was not different among the productive deletions (sp7-Δ8-co, sp7-Δ29-co, sp7-Δ42-co, sp7-Δ43-co) and the non-deleted version (sp7-co) indicating that they are all efficiently produced and processed within the cell. Intracellular GAA activity was instead very low for sp7-Δ47-co and sp7-Δ62-co versions and significantly lower when compared to all the other engineered versions [deleted (sp7-Δ8-co, sp7-Δ29-co, sp7-Δ42-co, sp7-Δ43-co) and non-deleted (sp7-co)].

We also performed the analysis of GAA activity in media and lysates of HuH7 cells transfected with different GAA versions (all codon optimized): 1. native GAA including the native sp1 GAA signal peptide (co), 2. engineered GAA containing the heterologous sp6 or sp8 signal peptide (sp6-co, sp8-co), and 3. engineered GAA containing the heterologous sp6 or sp8 signal peptide followed by the deletion of 8 amino acids (sp6-Δ8-co, sp8-Δ8-co). The analysis showed (FIG. 10) significantly higher GAA activity in media of cells transfected with Δ8 versions compared to: i. their respective engineered non-deleted GAA versions (sp6-co or sp8-co); and ii. native GAA (co). Interestingly, intracellular GAA activity was not different among all the engineered GAA versions (both deleted and non-deleted) indicating that they are all efficiently produced and processed within the cell (cell lysates panel). Intracellular GAA activity was instead significantly higher when using native GAA (co) compared to the engineered versions, indicating that the native GAA is mainly retained in the cell.

The invention claimed is:

1. A recombinant adeno-associated virus (AAV) vector comprising an expression cassette, said expression cassette comprising a nucleic acid molecule encoding a truncated human acid alpha-glucosidase (hGAA) polypeptide, said truncated hGAA polypeptide comprising a deletion of 1 to 75 consecutive amino acids from its N-terminal end as compared to a parent GAA polypeptide,
wherein said parent GAA polypeptide corresponds to a precursor form of a GAA polypeptide devoid of its signal peptide, and
wherein said truncated hGAA polypeptide further comprises a signal peptide fused to its N-terminal end.

2. The recombinant AAV vector of claim 1, wherein said truncated hGAA polypeptide has 6, 7, 8, 9, 10, 40, 41, 42, 43, 44, 45 or 46 consecutive amino acids deleted at its N-terminal end as compared to said parent GAA polypeptide.

3. The recombinant AAV vector of claim 1, wherein said truncated hGAA polypeptide has 8, 42 or 43 consecutive amino acids deleted at its N-terminal end as compared to said parent GAA polypeptide.

4. The recombinant AAV vector of claim 1, wherein said truncated hGAA polypeptide has 8 consecutive amino acids deleted at its N-terminal end as compared to said parent GAA polypeptide.

5. The recombinant AAV vector of claim 1, wherein said parent GAA polypeptide has the amino acid sequence of SEQ ID NO:1 or SEQ ID NO:33.

6. The recombinant AAV vector of claim 1, wherein said truncated hGAA polypeptide has the amino acid sequence of SEQ ID NO:27, SEQ ID NO:28, SEQ ID NO:34 or SEQ ID NO:35.

7. The recombinant AAV vector of claim 1, wherein said fused signal peptide (a) has an amino acid sequence selected from the group consisting of SEQ ID NO:3, SEQ ID NO:4, SEQ ID NO:5, SEQ ID NO:6 and SEQ ID NO:7.

8. The recombinant AAV vector of claim 1, wherein said fused signal peptide has the amino acid sequence of SEQ ID NO:3.

9. The recombinant AAV vector of claim 1, wherein said nucleic acid molecule is operably linked to a promoter.

10. The recombinant AAV vector of claim 9, wherein said promoter is a liver-specific promoter.

11. The recombinant AAV vector of claim 10 wherein said liver-specific promoter is selected from the group consisting of the alpha-1 antitrypsin promoter (hAAT), the transthyretin promoter, the albumin promoter and the thyroxine-binding globulin (TBG) promoter.

12. The recombinant AAV vector of claim 1, wherein said expression cassette optionally comprises an intron.

13. The recombinant AAV vector of claim 1, wherein said expression cassette comprises, in this order: an enhancer; an intron; a liver-specific promoter; said nucleic acid molecule encoding said truncated GAA polypeptide; and a polyadenylation signal.

14. The recombinant AAV vector of claim 1, wherein said expression cassette comprises in this order: an ApoE control region; a HBB2 intron; a hAAT promoter; said nucleic acid molecule encoding said truncated GAA polypeptide; and a bovine growth hormone polyadenylation signal.

15. The recombinant AAV vector of claim 14, wherein said expression cassette comprises the nucleotide sequence of any one of SEQ ID NOs:22 to 26.

16. The recombinant AAV vector of claim 1, wherein said recombinant AAV vector is a single-stranded or double-stranded self-complementary AAV vector.

17. A cell transformed with the recombinant AAV vector of claim 1.

18. The cell of claim 17, wherein said cell is a liver cell or a muscle cell.

19. A pharmaceutical composition comprising a therapeutically effective amount of the recombinant AAV vector of claim 1 and a pharmaceutically acceptable carrier.

20. The recombinant AAV vector of claim 1, wherein said recombinant AAV vector further comprises a capsid.

* * * * *

UNITED STATES PATENT AND TRADEMARK OFFICE
CERTIFICATE OF CORRECTION

PATENT NO. : 11,339,406 B2
APPLICATION NO. : 16/332379
DATED : May 24, 2022
INVENTOR(S) : Federico Mingozzi and Giuseppe Ronzitti It is certified that error appears in the above-identified patent and that said Letters Patent is hereby corrected as shown below:

In the Specification

Column 11,
Line 46, "is a 46," should read --is a $\Delta 6$,--.

Column 18,
Line 27, "$\Delta 8$, 429," should read --$\Delta 8$, $\Delta 29$,--.

Column 19,
Line 65, "to a $\Delta 48$" should read --to a $\Delta 8$--.

Column 24,
Line 66, "S23S30.)," should read --S23-S30.),--.

Column 40,
Line 8, "(66 8)" should read --($\Delta 8$)--.

Column 41,
Line 4, "66 8 and" should read --$\Delta 8$ and--.

Signed and Sealed this
Fourteenth Day of March, 2023

Katherine Kelly Vidal
*Director of the United States Patent and Trademark Office*